(12) United States Patent
Lieb et al.

(10) Patent No.: US 6,255,342 B1
(45) Date of Patent: Jul. 3, 2001

(54) 2-AND 2,5-SUBSTITUTED PHENYLKETOENOLS

(75) Inventors: Folker Lieb, Leverkusen; Reiner Fischer, Monheim; Thomas Bretschneider, Lohmar; Michael Ruther, Monheim; Alan Graff, Köln; Udo Schneider, Leverkusen; Christoph Erdelen, Leichlingen; Ulrike Wachendorff-Neumann, Neuwied; Wolfram Andersch, Bergisch Gladbach; Andreas Turberg, Erkrath, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/548,129

(22) Filed: Apr. 12, 2000

Related U.S. Application Data

(62) Division of application No. 09/230,653, filed as application No. PCT/EP97/03973 on Jul. 23, 1997, now Pat. No. 6,114,374.

(30) Foreign Application Priority Data

Aug. 5, 1996 (DE) .............................................. 196 31 586
Apr. 21, 1997 (DE) .............................................. 197 16 591

(51) Int. Cl.[7] .............................. A01N 37/10; C07C 69/76
(52) U.S. Cl. .............................................. 514/533; 560/61
(58) Field of Search ................................ 560/61; 514/533

(56) References Cited

U.S. PATENT DOCUMENTS

| 3,542,809 | 11/1970 | Nakanishi . |
| 5,094,681 | 3/1992 | Krämer et al. . |
| 5,207,817 | 5/1993 | Krämer . |
| 5,258,527 | 11/1993 | Krauskopf et al. . |
| 5,262,383 | 11/1993 | Fischer et al. . |
| 5,393,729 | 2/1995 | Fischer et al. . |

(List continued on next page.)

FOREIGN PATENT DOCUMENTS

| 2025983 | 3/1991 | (CA) . |
| 2182094 | 8/1995 | (CA) . |
| 2187015 | 10/1995 | (CA) . |
| 3314249 | 10/1984 | (DE) . |
| 94/29268 | 12/1994 | (WO) . |
| 95/01358 | 1/1995 | (WO) . |
| 96/25395 | 8/1996 | (WO) . |
| 96/35664 | 11/1996 | (WO) . |
| 97/01535 | 1/1997 | (WO) . |
| 97/02243 | 1/1997 | (WO) . |

OTHER PUBLICATIONS

J. Chem. Soc. Perkin Trans. 1, (month unavailable) 1985, pp. 1567–76, Campbell et al, Synthesis of (E)–and (Z)–Pulvinones.
Arch. Pharm. A.M. Chirzai et al, 309/76, (month unavailable) 1976, pp. 588–564, Synthesen von Heterocyclen, 184.
Chem. Ber. 91, (month unavailable) 1958, p. 2849, K–H Boltze & K. Heidenbluth, Zur Synthese 3–subtituierter 4–Hydroxy–pyrone–(2), I.

(List continued on next page.)

Primary Examiner—Deborah C. Lambkin
(74) Attorney, Agent, or Firm—Joseph C. Gil

(57) ABSTRACT

The invention relates to novel phenyl-substituted cyclic ketoenols of the formula (I)

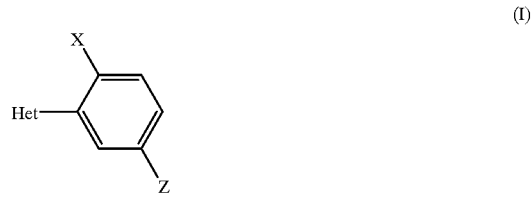

in which
Het represents one of the groups

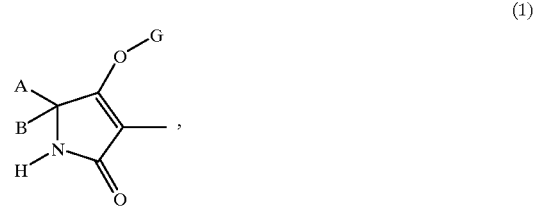

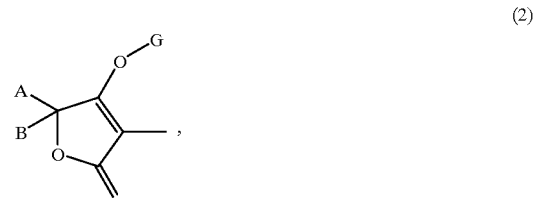

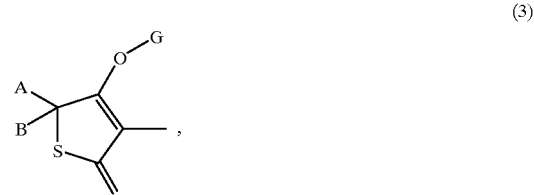

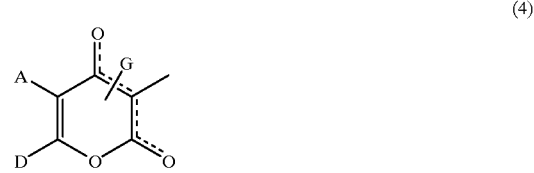

in which A, B, D, G, X and Z are each as defined in the description, to a plurality of processes and intermediates for their preparation, and to their use as pesticides.

2 Claims, No Drawings

U.S. PATENT DOCUMENTS

| | | |
|---|---|---|
| 5,462,913 | 10/1995 | Fischer et al. . |
| 5,504,057 | 4/1996 | Fischer et al. . |
| 5,508,436 | 4/1996 | Fischer et al. . |
| 5,567,671 | 10/1996 | Fischer et al. . |
| 5,589,469 | 12/1996 | Fischer et al. . |
| 5,602,078 | 2/1997 | Fischer et al. . |
| 5,610,122 | 3/1997 | Fischer et al. . |
| 5,616,563 | 4/1997 | Creighton et al. . |
| 5,622,917 | 4/1997 | Fischer et al. . |
| 5,672,718 | 9/1997 | Fischer et al. . |
| 5,677,449 | 10/1997 | Fischer et al. . |
| 5,719,310 | 2/1998 | Fischer et al. . |
| 5,830,825 | 11/1998 | Fischer et al. . |
| 5,945,379 * | 8/1999 | Dollinger et al. ............ 504/130 |
| 6,028,032 * | 2/2000 | Cramp et al. ............ 504/223 |
| 6,114,374 * | 8/1999 | Lieb et al. ............ 514/424 |

OTHER PUBLICATIONS

Chem. Reviews 52, (month unavailable) 1953, pp. 237–416, N. O.V. Sonntag, The Reactions of Aliphatic Chlorides.

Indian J. Chem. 6, B. Bhattacharya, (month unavailable) 1968, pp. 341–345, Isoquinoline.

Derivatives: Part XVIII–Formation of I–alkyl–(or alkaryl of aryl)–3–methyl–7–chloro–(or 5–chloro)–isoquinolines.

Chem. & Industry (London) Nov. 9, 1968, p. 1568, Harrison et al, Use of molecular sieves in the methyl esterification of carboxylic acids.

Schotten–Baumann (Organikum, VEB Deutscher Verlag der Wissenschaften, Berlin, (month unavailable) 1977, p. 505, Reaktionen von Carbonsauren und Carbonsaurederivaten mit Basen.

Organikum, 15th edition, p. 533, VEB Deutscher Verlag der Wissenschaften, Berlin (month unavailable) 1977, Addition von Basen an Nitrilen.

Compagnon, Miocuque, Ann. Chim. (month unavailable) 1970, (Paris) [14]5, p. 11–22, 23–27, Attion Des Reactifs Uucleophiles Sur La Triple Liaison Nitrile.

L. Munday, J. Chem. Soc., (month unavailable) 1961, Amino–acids of the Cyclohexane Series Part I.

J.T. Edward, C. Jitrangeri, Can. J. Chem. 53, May 16, 1975, p. 3339–3350J.T. Edward, C. J Jitrangeri, Can. J. Chem. 53, May 16, 1975, pp. 3339–3350.

M.S. Chambers, E.J. Thomas & D.J. Williams, J. Chem., Soc., Chem. Commun. (month unavailable ) 1987, pp. 1228–1230, An Asymmetric synthesis of Thiotetronic Acids using Chirality Transfer via an Allyl Xanthate–to–Dithio–carbonate Rearrangement. X–Ray Crystal Structure of (5R)–2, 5–Dihydro–r–hydroxy–5–methyl–3–phenyl–5–prop–1'enyl–2–oxothiophene.

Journal of Antibiotics, (month unavailable) 1983, pp. 1589–1593, Syntheses and Biological Activities of Thiotetromycin Analogs.

Organic Preparations and Procedures Int. 7(4), pp. 155–158 (month unavailable) 1975, Synthesis of Chlorocarbonyl Ketenes, Susumu Nakanishi and Kenneth Butler.

Tetrahedron Letters, vol. 27, No. 24 pp. 2763–2766, (month unavailable) 1986, Dimethyl Arylmalonates from Cerium (IV) ammonium Nitrate Promoted Reactions of Dimethyl Malonate with Aromatic Compounds in Methanol.

Organikum VEB Deutscher Verlag der Wissenschaften, Berlin (month unavailable) 1977, pp. 584–588 (see p. 587) Allgemeine Arbeitsvorschrift für die Esterkondensation und die Glycidestersynthese nach Darzens (Tab. 7.157).

Organikum, VEB Deutscher Verlag der Wissenschaften, Berlin,(month unavailable) 1977, p. 517ff Reakitionen von Caronsauren und Carbonsaurederivaten mit Basen.

Reg. No. 5398–79–8, CA Index name: Benzeneacetic acid, 2,5–dichloro–(9CI).

* cited by examiner

2-AND 2,5-SUBSTITUTED PHENYLKETOENOLS

This is a Divisional Application of Ser. No. 09/230,653 filed Jan. 28, 1999, U.S. Pat. No. 6,114,374 which is a 371 of PCT/EP97/03973 Jul. 23, 1997.

The invention relates to novel phenyl-substituted cyclic ketoenols, to a plurality of processes and intermediates for their preparation and to their use as pesticides.

It has already been disclosed that certain phenyl-substituted cyclic ketoenols are active as insecticides, acaricides and/or herbicides.

Also known are 1H-arylpyrrolidine-dione derivatives (EP-A-456 063, EP-A-521 334, EP-A-596 298, EP-A-613 884, EP-A-613 885, DE 44 40 594, WO 94/01 997, WO 95/01 358, WO 95/26 954, WO 95/20 572, EP-A-0 668 267, WO 96/25 395, WO 96/35 664, WO 97/01 535 and WO 97/02 243).

It is known that certain substituted $\Delta^3$-dihydrofuran-2-one derivatives have herbicidal properties (cf. DE-A-4 014 420). The synthesis of the tetronic acid derivatives used as starting materials (such as, for example, 3-(2-methylphenyl)-4-hydroxy-5-(4-fluorophenyl)-$\Delta^3$-dihydrofuran-2-one) is likewise described in DE-A-4 014 420. Compounds of similar structure without details of an insecticidal and/or acaricidal activity are known from the publication Campbell et al., J. Chem. Soc., Perkin Trans. 1, 1985, (8) 1567–76. Furthermore, 3-aryl-$\Delta^3$-dihydrofuranone derivatives having herbicidal, acaricidal and insecticial properties are disclosed in EP-A-528 156, EP-A 0 647 637, WO 95/26345, WO 96/20 196, WO 96/25 395, WO 96/35 664, WO 97/01 535 and WO 97/02 243.

Certain phenyl-pyrone derivatives unsubstitued in the phenyl ring have already been disclosed (cf. A. M. Chirazi, T. Kappe and E. Ziegler, Arch. Pharm. 309, 558 (1976) and K.-H. Boltze and K. Heidenbluth, Chem. Ber. 91, 2849), a possible utility for these compounds as pesticides not being indicated. Phenyl-pyrone derivatives substituted in the phenyl ring and having herbicidal, acaricidal and insecticidal properties are described in EP-A-588 137, WO 96/25 395, WO 96/35 664, WO 97/01 535 and WO 97/02 243.

However, the acaricidal and insecticidal activity and/or spectrum of action, and/or the toleration of the known compounds by plants, in particular by crops, is not always satisfactory.

The invention, accordingly, provides compounds of the formula (I)

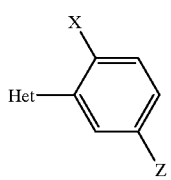

(I)

in which
X represents halogen, alkyl, alkenyl, alkynyl, alkoxy, benzyloxy, halogenoalkyl, halogenoalkoxy, cyano or nitro, Z represents hydrogen, amino, halogen, alkyl, alkoxy, halogenoalkyl, halogenoalkoxy, hydroxyl, cyano, nitro or respectively optionally substituted phenoxy, phenylthio, 5- or 6-membered hetaryloxy, 5- or 6-membered hetarylthio, phenylalkyloxy or phenylalkylthio and Het represents one of the groups

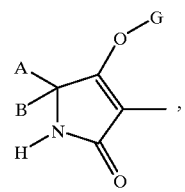

(1)

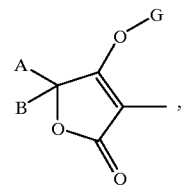

(2)

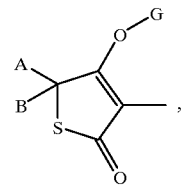

(3)

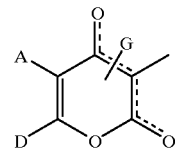

(4)

in which

A represents a respectively optionally substituted radical from the group consisting of alkyl, alkenyl, alkoxyalkyl, polyalkoxyalkyl and alkylthioalkyl, represents respectively saturated or unsaturated and optionally substituted cycloalkyl or heterocyclyl or represents respectively optionally halogen-, alkyl-, halogenoalkyl-, alkoxy-, halogenoalkoxy-, cyano- or nitro-substituted aryl, arylalkyl or hetaryl, B represents alkyl or alkoxyalkyl or A and B together with the carbon atom that they are attached to represent a saturated or unsaturated, optionally substituted carbocycle or heterocycle, D represents hydrogen or represents an optionally substituted radical from the group consisting of alkyl, alkenyl, alkynyl, alkoxyalkyl, polyalkoxyalkyl, alkylthioalkyl, saturated or unsaturated cycloalkyl, saturated or unsaturated heterocyclyl, arylalkyl, aryl, hetarylalkyl or hetaryl or A and D together with the atoms that they are attached to represent a respectively optionally substituted carbocycle or heterocycle, G represents hydrogen (a) or represents one of the groups

(b)

(c)

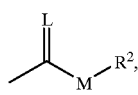

(d)

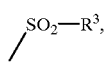

(e)

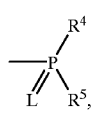

(f) E or (g)

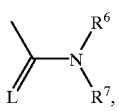

in which

E represents a metal ion equivalent or an ammonium ion,

L represents oxygen or sulphur,

M represents oxygen or sulphur, $R^1$ represents respectively optionally halogen-substituted alkyl, alkenyl, alkoxyalkyl, alkylthioalkyl or polyalkoxyalkyl or represents respectively optionally halogen-, alkyl- or alkoxy-substituted cycloalkyl or heterocyclyl or represents respectively optionally substituted phenyl, phenylalkyl, hetaryl, phenoxyalkyl or hetaryloxyalkyl, $R^2$ represents respectively optionally halogen-substituted alkyl, alkenyl, alkoxyalkyl or polyalkoxyalkyl or represents respectively optionally substituted cycloalkyl, phenyl or benzyl, $R^3$, $R^4$ and $R^5$ independently of one another each represent respectively optionally halogen-substituted alkyl, alkoxy, alkylamino, dialkylamino, alkylthio, alkenylthio or cycloalkylthio or represent respectively optionally substituted phenyl, benzyl, phenoxy or phenylthio, $R^6$ and $R^7$ independently of one another each represent hydrogen, represent respectively optionally halogen-substituted alkyl, cycloalkyl, alkenyl, alkoxy, alkoxyalkyl, represent respectively optionally substituted phenyl or benzyl, or form together with the nitrogen atom that they are attached to an optionally oxygen- or sulphur-containing, optionally substituted cycle.

The compounds of the formula (I) can also be present, depending on the nature of the substituents, as geometric and/or optical isomers and isomer mixtures of differing composition which, if appropriate, can be separated in a customary manner. Both the pure isomers and the isomer mixtures, their preparation and use, and compositions comprising them are part of the subject matter of the present invention. In the following, for simplicity, however, compounds of the formula (I) are always referred to, although both pure compounds and, if appropriate, mixtures having different proportions of isomer compounds are intended.

Including the meanings (1) to (4) of the group Het, the following principal structures (I-1) to (I-4) result:

(I-1)

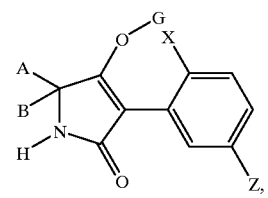

(I-2)

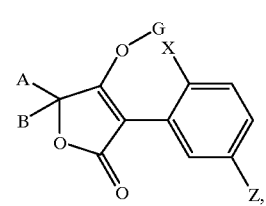

(I-3)

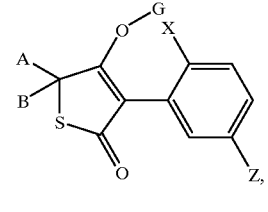

(I-4)

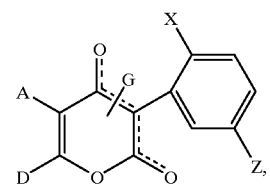

in which

A, B, D, G, X and Z are each as defined above.

Including the various meanings (a), (b), (c), (d), (e), (f) and (g) of the group G, the following principal structures (I-1-a) to (I-1-g) result if Het represents the group (1)

(I-1-a):

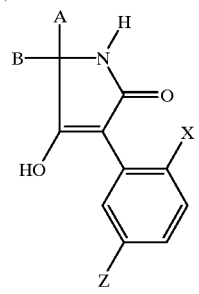

(I-1-b):

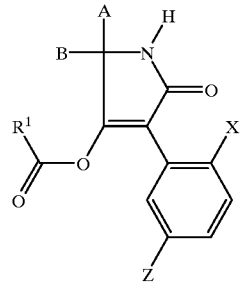

-continued
(I-1-c):
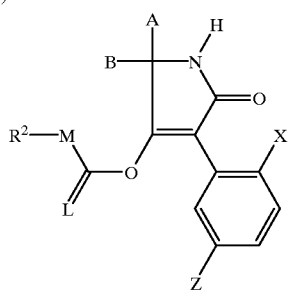
(I-1-d):
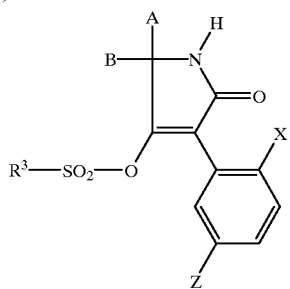
(I-1-e):
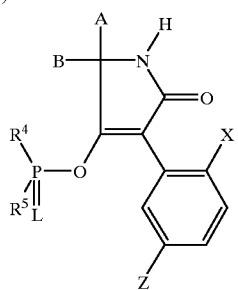
(I-1-f):
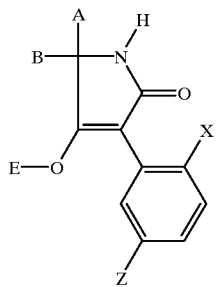
(I-1-g):
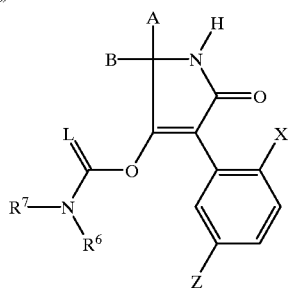
in which
A, B, E, L, M, X, Z, $R^1$, $R^2$, $R^3$, $R^4$, $R^5$, $R^6$ and $R^7$ are each as defined above.
Including the various meanings (a), (b), (c), (d), (e), (f) and (g) of the group G, the following principal structures (I-2-a) to (I-2-g) result if Het represents the group (2)
(I-2-a):
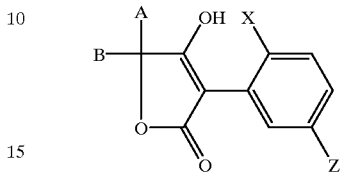
(I-2-b):
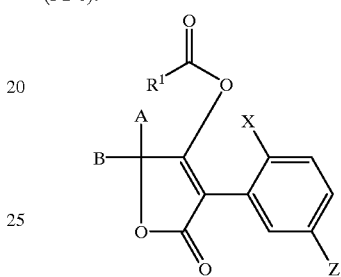
(I-2-c):
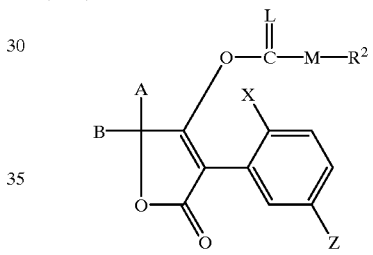
(I-2-d):
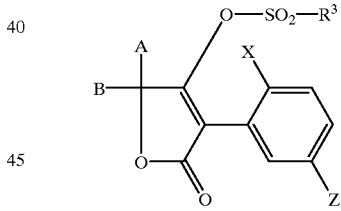
(I-2-e):
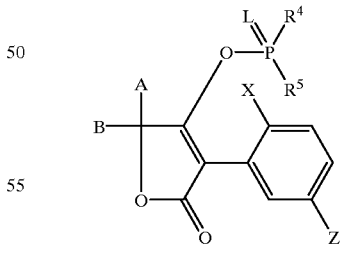
(I-2-f):
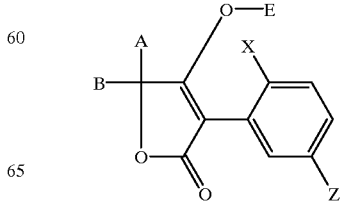

-continued (I-2-g):
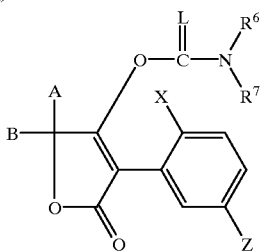

in which

A, B, E, L, M, X, Z, $R^1$, $R^2$, $R^3$, $R^4$, $R^5$, $R^6$ and $R^7$ are each as defined above.

Including the various meanings (a), (b), (c), (d), (e), (f) and (g) of the group G, the following principal structures (I-3-a) to (I-3-g) result if Het represents the group (3)

(I-3-a):
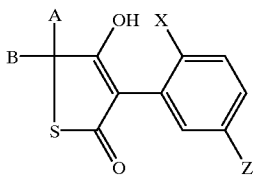

(I-3-b):
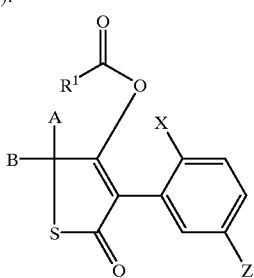

(I-3-c):
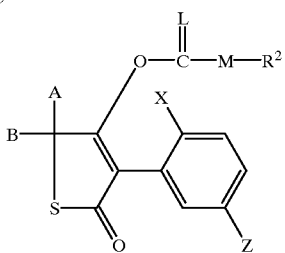

(I-3-d):
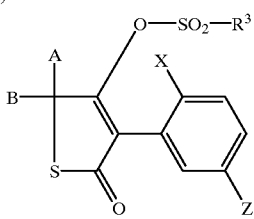

-continued (I-3-e):
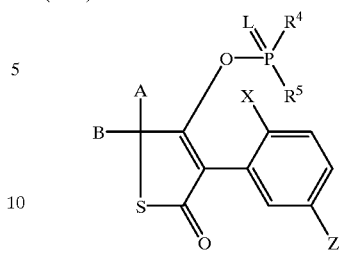

(I-3-f):
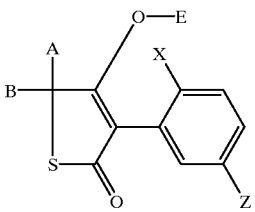

(I-3-g):
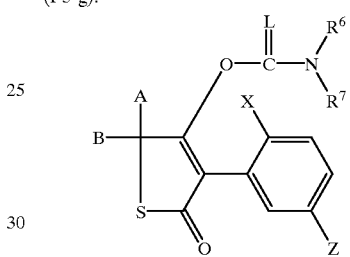

in which

A, B, E, L, M, X, Z, $R^1$, $R^2$, $R^3$, $R^4$, $R^5$, $R^6$ and $R^7$ are each as defined above.

Depending on the position of the substituent G, the compounds of the formula (I-4) can be present in the two isomeric forms of formulae (I-4)$_a$ and (I-4)$_b$ (I-4)$_a$
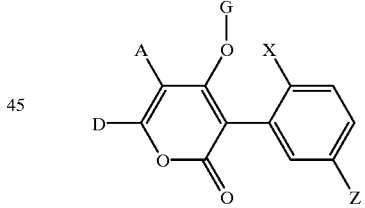

(I-4)$_b$
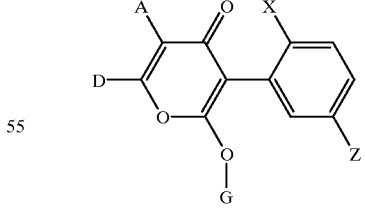

which is intended to be expressed by the dashed line in the formula (I-4).

The compounds of the formulae (I-4)$_a$ and (I-4)$_b$ can be present both as mixtures and in the form of their pure isomers. Mixtures of the compounds of the formulae (I-4)$_a$ and (I-4)$_b$ can, if desired, be separated by physical methods in a manner known per se, for example by chromatographic methods.

For better clarity, in the following in each case only one of the possible isomers is shown. This does not exclude the possibility that the compounds can optionally be present in the form of the isomer mixtures or in the other respective isomer form.

Including the various meanings (a), (b), (c), (d), (e), (f) and (g) of the group G, the following principal structures (I-4-a) to (I-4-g) result if Het represents the group (4)

(I-4-a):

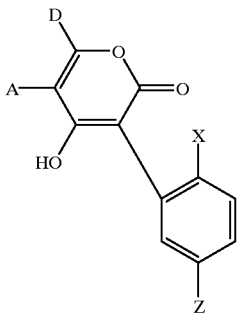

(I-4-b):

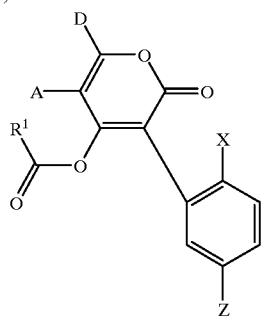

(I-4-c):

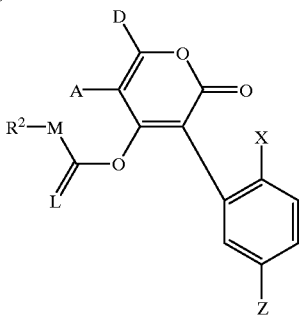

(I-4-d):

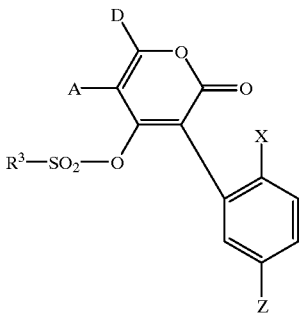

(I-4-e):

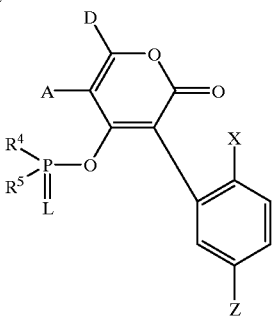

(I-4-f):

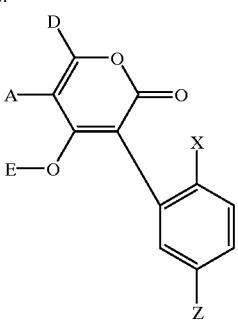

(I-4-g):

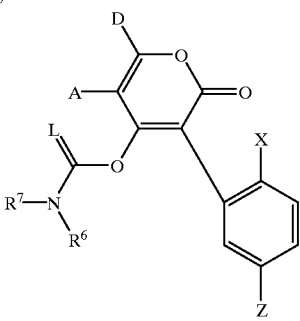

in which
A, D, E, L, M, X, Z, $R^1$, $R^2$, $R^3$, $R^4$, $R^5$, $R^6$ and $R^7$ are each as defined above.

Furthermore, it has been found that the novel compounds of the formula (I) are obtained by one of the processes described below:

(A) Compounds of the formula (I-1-a)

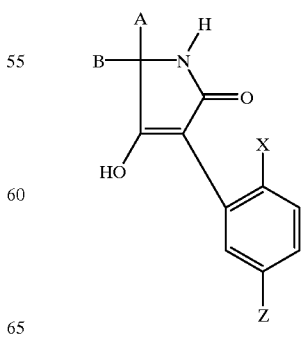

(I-1-a)

in which

A, B, X and Z are each as defined above, are obtained by the intramolecular condensation of compounds of the formula (II)

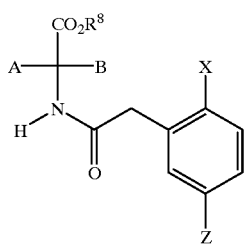
(II)

in which

A, B, X and Z are each as defined above, and
$R^8$ represents alkyl (preferably $C_1$–$C_6$-alkyl),
in the presence of a diluent and in the presence of a base.

(B) Furthermore, it was found that compounds of the formula (I-2-a)

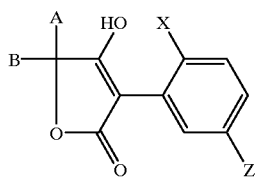
(I-2-a)

in which

A, B, X and Z are each as defined above, are obtained by the intramolecular condensation of compounds of the formula (III)

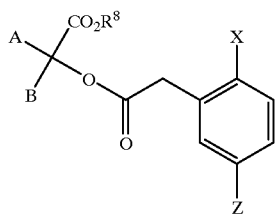
(III)

in which

A, B, X, Z and $R^8$ are each as defined above, in the presence of a diluent and in the presence of a base.

(C) Furthermore, it was found that compounds of the formula (I-3-a)

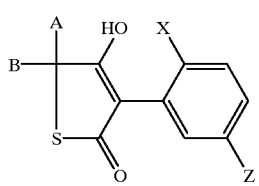
(I-3-a)

in which

A, B, X and Z are each as defined above, are obtained by the intramolecular cyclization of compounds of the formula (IV)

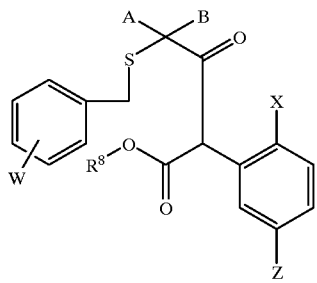
(IV)

in which

A, B, X, Z and $R^8$ are each as defined above and

W represents hydrogen, halogen, alkyl (preferably $C_1$–$C_6$-alkyl) or alkoxy (preferably $C_1$–$C_8$-alkoxy), if appropriate in the presence of a diluent and in the presence of an acid.

(D) Furthermore, it was found that compounds of the formula (I-4-a)

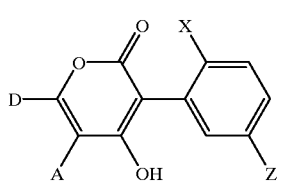
(I-4-a)

in which

A, D, X and Z are each as defined above, are obtained by reacting compounds of the formula (V)

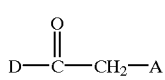
(V)

in which

A and D are each as defined above, or their silyl enol ethers of the formula (Va)

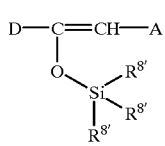
(Va)

in which

A and D are each as defined above and $R^8$ represents alkyl (preferably methyl), with compounds of the formula (VI)

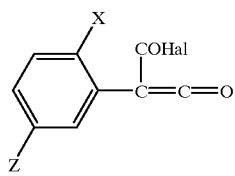

(VI)

in which

X and Z are each as defined above and

Hal represents halogen (preferably chlorine or bromine), if appropriate in the presence of a diluent and if appropriate in the presence of an acid acceptor.

Furthermore, it was found (E) that the compounds of the formulae (I-1-b) to (I-4-b) shown above in which A, B, D, $R^1$, X and Z are each as defined above are obtained by reacting compounds of the formulae (I-1-a) to (I-4-a) shown above in which A, B, D, X and Z are each as defined above α) with acid halides of the formula (VII)

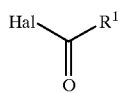

(VII)

in which $R^1$ is as defined above and

Hal represents halogen (in particular chlorine or bromine), or

β) with carboxylic anhydrides of the formula (VIII)

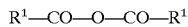

(VIII)

in which $R^1$ is as defined above, if appropriate in the presence of a diluent and if appropriate in the presence of an acid-binding agent;

(F) that the compounds of the formulae (I-1-c) to (I-4-c) shown above in which A, B, D, $R^2$, M, X and Z are each as defined above and L represents oxygen are obtained by reacting compounds of the formulae (I-1-a) to (I-4-a) shown above in which A, B, D, X and Z are each as defined above, in each case with chloroformic esters or chloroformic thioesters of the formula (IX)

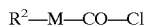

(IX)

in which $R^2$ and M are each as defined above, if appropriate in the presence of a diluent and if appropriate in the presence of an acid-binding agent;

(G) that compounds of the formulae (I-1-c) to (I-4-c) shown above in which A, B, D, $R^2$, M, X and Z are each as defined above and L represents sulphur are obtained by reacting compounds of the formulae (I-1-a) to (I-4-a) shown above in which A, B, D, X and Z are each as defined above, in each case with chloromonothioformic esters or chlorodithioformic esters of the formula (X)

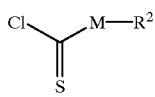

(X)

in which

M and $R^2$ are each as defined above, if appropriate in the presence of a diluent and if appropriate in the presence of an acid-binding agent, (H) that compounds of the formulae (I-1-d) to (I-4-d) shown above in which A, B, D, $R^3$, X and Z are each as defined above are obtained by reacting compounds of the formulae (I-1-a) to (I-4-a) shown above in which A, B, D, X and Z are each as defined above, in each case with sulphonyl chlorides of the formula (XII)

(XII)

in which $R^3$ is as defined above, if appropriate in the presence of a diluent and if appropriate in the presence of an acid-binding agent, (I) that compounds of the formulae (I-1-e) to (I-4-e) shown above in which A, B, D, L, $R^4$, $R^5$, X and Z are each as defined above are obtained by reacting compounds of the formulae (I-1-a) to (I-4-a) shown above in which A, B, D, X and Z are each as defined above, in each case with phosphorus compounds of the formula (XIII)

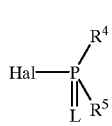

(XIII)

in which

L, $R^4$ and $R^5$ are each as defined above and

Hal represents halogen (in particular chlorine or bromine), if appropriate in the presence of a diluent and if appropriate in the presence of an acid-binding agent, (J) that compounds of the formulae (I-1-f) to (I-4-f) shown above in which A, B, D, E, X and Z are each as defined above are obtained by reacting compounds of the formulae (I-1-a) to (I-4-a) in which A, B, D, X and Z are each as defined above, in each case with metal compounds or amines of the formulae (XIV) or (XV)

(XIV)

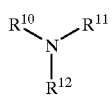

(XV)

in which

Me represents a mono- or divalent metal (preferably an alkali metal or alkaline earth metal, such as lithium, sodium, potassium, magnesium or calcium), t represents the number 1 or 2 and $R^{10}$, $R^{11}$, $R^{12}$ independently of one another each represent hydrogen or alkyl (preferably $C_1$–$C_8$-alkyl), if appropriate in the presence of a diluent;

(K) that compounds of the formulae (I-1-g) to (I-4-g) shown above in which A, B, D, L, $R^6$, $R^7$, X and Z are each as defined above are obtained by reacting compounds of the formulae (I-1-a) to (I-4-a) shown above in which A, B, D, X and Z are each as defined above, in each case α) with isocyanates or isothiocyanates of the formula (XVI)

$R^6$—N=C=L  (XVI)

in which $R^6$ and L are each as defined above, if appropriate in the presence of a diluent and if appropriate in the presence of a catalyst, or β) with carbamoyl chlorides or thiocarbamoyl chlorides of the formula (XVII)

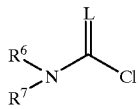

(XVII)

in which

L, $R^6$ and $R^7$ are each as defined above, if appropriate in the presence of a diluent and if appropriate in the presence of an acid-binding agent.

Furthermore, it has been found that the novel compounds of the formula (I) have a very good activity as pesticides, preferably as insecticides and acaricides, and that they additionally are very well tolerated by plants, in particular by crops.

Formula (I) provides a general definition of the compounds according to the invention. Preferred substituents or ranges of the radicals shown in the formulae mentioned hereinabove and hereinbelow are illustrated below:

X preferably represents halogen, $C_1$–$C_6$-alkyl, $C_2$–$C_6$-alkenyl, $C_2$–$C_6$-alkynyl, $C_1$–$C_6$-alkoxy, benzyloxy, $C_1$–$C_4$-halogenoalkyl, $C_1$–$C_4$-halogenoalkoxy, cyano or nitro.

Z preferably represents hydrogen, amino, halogen, $C_1$–$C_6$-alkyl, $C_1$–$C_6$-alkoxy, $C_1$–$C_4$-halogenoalkyl, $C_1$–$C_4$-halogenoalkoxy, hydroxyl, cyano, nitro or respectively optionally halogen-, $C_1$–$C_4$-alkyl-, $C_1$–$C_4$-alkoxy-, $C_1$–$C_4$-halogenoalkyl-, $C_1$–$C_4$-halogenoalkoxy-, nitro- or cyano-substituted phenoxy phenylthio, thiazolyloxy, pyridinyloxy, pyrimidinyloxy, pyrazolyloxy, phenyl-$C_1$–$C_4$-alkyloxy or phenyl-$C_1$–$C_7$-alkylthio.

Het preferably represents one of the groups

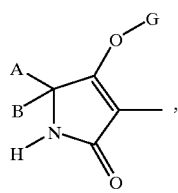

(1)

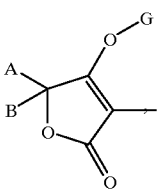

(2)

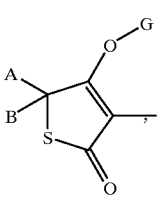

(3)

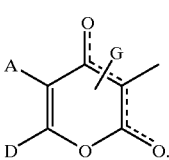

(4)

A preferably represents respectively optionally halogen-substituted $C_1$–$C_{12}$-alkyl, $C_2$–$C_8$-alkenyl, $C_1$–$C_{10}$-alkoxy-$C_1$–$C_8$-aklyl, poly-$C_1$–$C_8$-alkoxy-$C_1$–$C_8$-alkyl or $C_1$–$C_{10}$-alkylthio-$C_1$–$C_6$-alkyl, preferably represents optionally halogen-, $C_1$–$C_6$-alkyl- or $C_1$–$C_6$-alkoxy-substituted $C_3$–$C_8$-cycloalkyl in which optionally one or two not directly adjacent methylene groups are replaced by oxygen and/or sulphur, or preferably represents respectively optionally halogen-, $C_1$–$C_6$-alkyl-, $C_1$–$C_6$-halogenoalkyl-, $C_1$–$C_6$-alkoxy-, $C_1$–$C_6$-halogenoalkoxy-, cyano- or nitro-substituted phenyl, naphthyl, phenyl-$C_1$–$C_6$-alkyl, naphthyl-$C_1$–$C_6$-alkyl or hetaryl having 5 or 6 ring atoms and one to three hetero atoms from the group consisting of oxygen, sulphur and nitrogen (in particular from the group consisting of furanyl, pyridyl, imidazolyl, triazolyl, pyrazolyl, indolyl, thiazolyl and thienyl).

B preferably represents $C_1$–$C_{12}$-alkyl or $C_1$–$C_8$-alkoxy-$C_1$–$C_6$-alkyl or A, B and the carbon atom that they are attached to preferably represent $C_3$–$C_{10}$-cycloalkyl or $C_5$–$C_{10}$-cycloalkenyl where in each case one methylene group is optionally replaced by oxygen or sulphur and which are optionally substituted by $C_1$–$C_8$-alkyl, $C_3$–$C_{10}$-cycloalkyl, $C_1$–$C_8$-halogenoalkyl, $C_1$–$C_8$-alkoxy, $C_1$–$C_8$-alkylthio, halogen or phenyl or A, B and the carbon atom that they are attached to preferably represent $C_5$–$C_6$-cycloalkyl which is substituted by an alkylenediyl group optionally containing one or two not directly adjacent oxygen and/or sulphur atoms, or by an alkylenedioxy group or an alkylenedithioyl group forming a further five- to eight-membered ring with the carbon atom that it is attached to, or A, B and the carbon atom that they are attached to preferably represent $C_3$–$C_8$-cycloalkyl or $C_5$–$C_8$-cycloalkenyl in which two carbon atoms are linked to each other by respectively optionally $C_1$–$C_6$-alkyl-, $C_1$–$C_6$-alkoxy- or halogen-substituted $C_3$–$C_6$-alkanediyl, $C_3$–$C_6$-alkenediyl or $C_4$–$C_6$-alkanedienediyl, one methylene group in each case being optionally replaced by oxygen or sulphur.

D preferably represents hydrogen, preferably represents respectively optionally halogen-substituted $C_1$–$C_{12}$-alkyl, $C_3$–$C_8$-alkenyl, $C_3$–$C_8$-alkynyl, $C_1$–$C_{10}$-alkoxy-$C_2$–$C_8$-alkyl, poly-$C_1$–$C_8$-alkoxy-$C_2$–$C_8$-alkyl or $C_1$–$C_{10}$-alkylthio-$C_2$–$C_8$-alkyl, preferably represents optionally halogen-, $C_1$–$C_4$-alkyl-, $C_1$–$C_4$-alkoxy- or $C_1$–$C_4$-halogenoalkyl-substituted $C_3$–$C_8$-cycloalkyl in which optionally one or two not directly adjacent methylene groups are replaced by oxygen and/or sulphur, or preferably represents respectively optionally halogen-, $C_1$–$C_6$ alkyl-, $C_1$–$C_6$-halogenoalkyl-, $C_1$–$C_6$-alkoxy-, $C_1$–$C_6$-halogenoalkoxy-, cyano- or nitro-substituted phenyl, hetaryl having 5 or 6 ring atoms and one or two hetero atoms from the group consisting of oxygen, sulphur and nitrogen (in particular from the group consisting of furanyl, imidazolyl, pyridyl, thiazolyl, pyrazolyl, pyrimidyl, pyrrolyl, thienyl and triazolyl), phenyl-$C_1$–$C_6$-alkyl or hetaryl-$C_1$–$C_6$-alkyl having 5 or 6 ring atoms and one or two hetero atoms from the group consisting of oxygen, sulphur and nitrogen (in particular from the group consisting of furanyl-, imidazolyl-, pyridyl-, thiazolyl-, pyrazolyl-, pyrimidyl-, pyrrolyl-, thienyl- and triazolyl-$C_1$–$C_6$-alkyl) or A and D together preferably represent a $C_3$–$C_6$-alkanediyl, $C_3$–$C_6$-alkenediyl or $C_4$–$C_6$-alkadienediyl group in which respectively optionally one methylene group is replaced by oxygen or sulphur and which are respectively optionally substituted by halogen or respectively optionally halogen-substituted $C_1$–$C_{10}$-alkyl, $C_1$–$C_6$-alkoxy, $C_1$–$C_6$-alkylthio, $C_3$–$C_7$-cycloalkyl, phenyl or benzyloxy or by a further $C_3$–$C_6$-alkanediyl, $C_3$–$C_6$-alkenediyl or $C_4$–$C_6$-alkadienediyl group forming a fused ring, in which optionally respectively one methylene group is replaced by oxygen or sulphur and which are optionally substituted by $C_1$–$C_6$-alkyl, or A and D together represent a $C_3$–$C_6$-alkanediyl or $C_3$–$C_6$-alkenediyl group containing in each case optionally one of the following groups

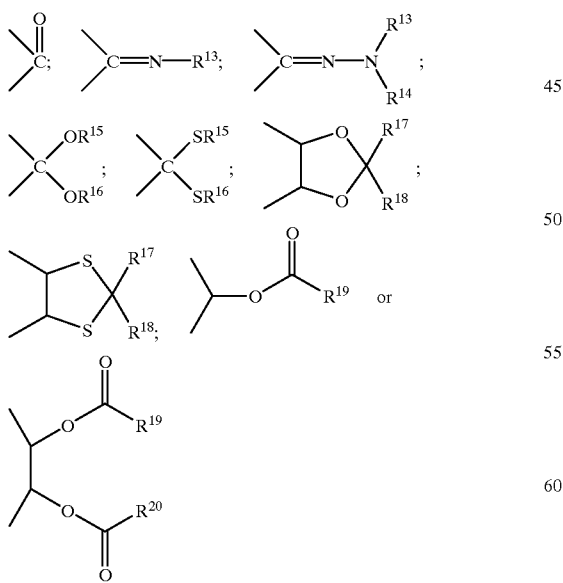

G preferably represents hydrogen (a) or represents one of the groups

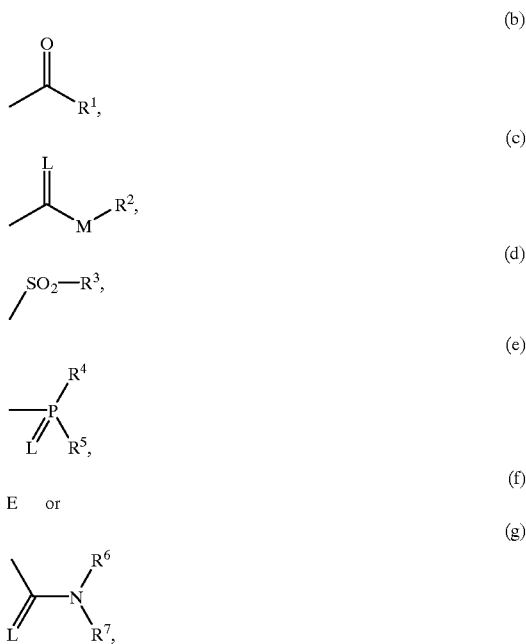

in which
E represents a metal ion equivalent or an ammonium ion,
L represents oxygen or sulphur and
M represents oxygen or sulphur.

$R^1$ preferably represents respectively optionally halogen-substituted $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl or poly-$C_1$–$C_8$-alkoxy-$C_1$–$C_8$-alkyl or preferably represents optionally halogen-, $C_1$–$C_6$-alkyl- or $C_1$–$C_6$-alkoxy-substituted $C_3$–$C_8$-cycloalkyl in which optionally one or two not directly adjacent methylene groups are replaced by oxygen and/or sulphur, preferably represents optionally halogen-, cyano-, nitro-, $C_1$–$C_6$-alkyl-, $C_1$–$C_6$-alkoxy-, $C_1$–$C_6$-halogenoalkyl-, $C_1$–$C_6$-halogenoalkoxy-, $C_1$–$C_6$-alkylthio- or $C_1$–$C_6$-alkylsulphonyl-substituted phenyl, preferably represents optionally halogen-, nitro-, cyano-, $C_1$–$C_6$-alkyl, $C_1$–$C_6$-alkoxy-, $C_1$–$C_6$-halogenoalkyl- or $C_1$–$C_6$-halogenoalkoxy-substituted phenyl-$C_1$–$C_6$-alkyl, preferably represents optionally halogen- or $C_1$–$C_6$-alkyl-substituted 5- or 6-membered hetaryl having one or two hetero atoms from the group consisting of oxygen, sulphur and nitrogen (in particular from the group consisting of pyrazolyl, thiazolyl, pyridyl, pyrimidyl, furanyl and thienyl), preferably represents optionally halogen- or $C_1$–$C_6$-alkyl-substituted phenoxy-$C_1$–$C_6$-alkyl or preferably represents optionally halogen-, amino- or $C_1$–$C_6$-alkyl-substituted 5- or 6-membered hetaryloxy-$C_1$–$C_6$-alkyl having one or two hetero atoms from the group consisting of oxygen, sulphur and nitrogen (in particular from the group consisting of pyridyloxy-$C_1$–$C_6$-alkyl, pyrimidyloxy-$C_1$–$C_6$-alkyl and thiazolyloxy-$C_1$–$C_6$-alkyl).

$R^2$ preferably represents respectively optionally halogen-substituted $C_1$–$C_{20}$-alkyl, $C_2$–$C_{20}$-alkenyl, $C_1$–$C_8$-alkoxy-$C_2$–$C_8$-alkyl or poly-$C_1$–$C_8$-alkoxy-$C_2$–$C_8$-alkyl, preferably represents optionally halogen-, $C_1$–$C_6$-alkyl- or $C_1$–$C_6$-alkoxy-substituted $C_3$–$C_8$-cycloalkyl or preferably represents respectively optionally halogen-, cyano-, nitro-, $C_1$–$C_6$alkyl-, $C_1$–$C_6$-alkoxy-, $C_1$–$C_6$-halogenoalkyl- or $C_1$–$C_6$-halogenoalkoxy-substituted phenyl or benzyl.

$R^3$ preferably represents optionally halogen-substituted $C_1$–$C_8$-alkyl or respectively optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, cyano- or nitro-substituted phenyl or benzyl.

$R^4$ and $R^5$ independently of one another each preferably represent respectively optionally halogen-substituted $C_1$–$C_8$-alkyl, $C_1$–$C_8$-alkoxy, $C_1$–$C_8$-alkylamino, di-($C_1$–$C_8$-alkyl)-amino, $C_1$–$C_8$-alkylthio or $C_3$–$C_8$-alkenylthio or preferably represent respectively optionally halogen-, nitro-, cyano-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkyl- or $C_1$–$C_4$-halogenoalkyl-substituted phenyl, phenoxy or phenylthio.

$R^6$ and $R^7$ independently of one another each preferably represent hydrogen, preferably represent respectively optionally halogen-substituted $C_1$–$C_8$-alkyl, $C_3$–$C_8$-cycloalkyl, $C_1$–$C_8$-alkoxy, $C_3$–$C_8$-alkenyl or $C_1$–$C_8$-alkoxy-$C_2$–$C_8$-alkyl, preferably represent respectively optionally halogen-, $C_1$–$C_8$-alkyl-, $C_1$–$C_8$-halogenoalkyl- or $C_1$–$C_8$-alkoxy-substituted phenyl or benzyl or together preferably represent an optionally $C_1$–$C_6$-alkyl-substituted $C_3$–$C_6$-alkylene radical in which optionally one methylene group is replaced by oxygen or sulphur.

$R^{13}$ preferably represents hydrogen or respectively optionally halogen-substituted $C_1$–$C_8$-alkyl or $C_1$–$C_8$-alkoxy, preferably represents optionally halogen-, $C_1$–$C_4$-alkyl- or $C_1$–$C_4$-alkoxy-substituted $C_3$–$C_8$-cycloalkyl in which optionally one methylene group is replaced by oxygen or sulphur, or preferably represents respectively optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro- or cyano-substituted phenyl, phenyl-$C_1$–$C_4$-alkyl or phenyl-$C_1$–$C_4$-alkoxy.

$R^{14}$ preferably represents hydrogen or $C_1$–$C_8$-alkyl or $R^{13}$ and $R^{14}$ together preferably represent $C_4$–$C_6$-alkanediyl.

$R^{15}$ and $R^{16}$ are identical or different and each preferably represent $C_1$–$C_6$-alkyl or $R^{15}$ and $R^{16}$ together preferably represent a $C_2$–$C_4$-alkanediyl radical which is optionally substituted by $C_1$–$C_6$-alkyl or by optionally halogen-, $C_1$–$C_4$-alkyl-, $C_1C_4$-halogenoalkyl-, $C_1$–$C_4$-alkoxy-, $C_1$–$C_4$-halogenoalkoxy-, nitro-or cyano-substituted phenyl.

$R^{17}$ and $R^{18}$ independently of one another each preferably represent hydrogen, preferably represent optionally halogen-substituted $C_1$–$C_8$-alkyl or preferably represent optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro- or cyano-substituted phenyl or $R^{17}$ and $R^{18}$ together with the carbon atom that they are attached to preferably represent optionally $C_1$–$C_4$-alkyl-substituted $C_5$–$C_7$-cycloalkyl in which optionally one methylene group is replaced by oxygen or sulphur.

$R^{19}$ and $R^{20}$ independently of one another each preferably represent $C_1$–$C_{10}$-alkyl, $C_2$–$C_{10}$-alkenyl, $C_1$–$C_{10}$-alkoxy, $C_1$–$C_{10}$-alkylamino, $C_3$–$C_{10}$-alkenylamino, di-($C_1$–$C_{10}$-alkyl)-amino or di-($C_3$–$C_{10}$-alkenyl)-amino.

X particularly preferably represents fluorine, chlorine, bromine, $C_1$–$C_4$-alkyl, $C_1$–$C_4$-alkoxy, benzyloxy, $C_1$–$C_2$-halogenoalkyl, $C_1$–$C_2$-halogenoalkoxy, cyano or nitro.

Z particularly preferably represents hydrogen, amino, fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, hydroxyl, cyano, nitro or respectively optionally fluorine-, chlorine-, bromine-, $C_1$–$C_4$-alkyl-, $C_1$–$C_4$-alkoxy-, $C_1$–$C_2$-halogenoalkyl-, $C_1$–$C_2$-halogenoalkoxy-, nitro- or cyano-substituted phenoxy or benzyloxy.

Het particularly preferably represents one of the groups

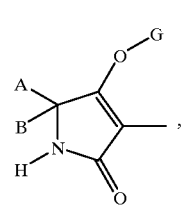

(1)

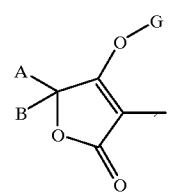

(2)

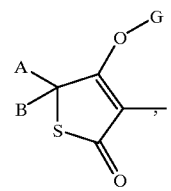

(3)

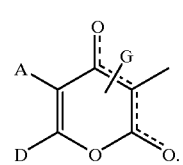

(4)

A particularly preferably represents respectively optionally fluorine- or chlorine-substituted $C_1$–$C_{10}$-alkyl, $C_2$–$C_6$-alkenyl, $C_1$–$C_8$-alkoxy-$C_1$–$C_6$-alkyl, poly-$C_1$–$C_6$-alkoxy-$C_1$–$C_6$-alkyl or $C_1$–$C_8$-alkylthio-$C_1$–$C_6$-alkyl or particularly preferably represents optionally fluorine-, chlorine-, $C_1$–$C_4$-alkyl- or $C_1$–$C_4$-alkoxy-substituted $C_3$–$C_7$-cycloalkyl in which optionally one or two not directly adjacent methylene groups are replaced by oxygen and/or sulphur, or particularly preferably represents respectively optionally fluorine-, chlorine-, bromine-, $C_1$–$C_4$-alkyl-, $C_1$–$C_4$-halogenoalkyl-, $C_1$–$C_4$-alkoxy-, $C_1$–$C_4$-halogenoalkoxy-, cyano, or nitro-substituted phenyl, furanyl, pyridyl, imidazolyl, triazolyl, pyrazolyl, indolyl, thiazolyl, thienyl or phenyl-$C_1$–$C_4$-alkyl.

B particularly preferably represents $C_1$–$C_{10}$-alkyl or $C_1$–$C_6$-alkoxy-$C_1$–$C_4$-alkyl or A, B and the carbon atom that they are attached to particularly preferably represent $C_3$–$C_8$-cycloalkyl or $C_5$–$C_8$-cycloalkenyl where one methylene group in each case is optionally replaced by oxygen or sulphur and which are optionally substituted by $C_1$–$C_6$-alkyl, $C_3$–$C_8$-cycloalkyl, $C_1$–$C_3$-halogenoalkyl, $C_1$–$C_6$-alkoxy, $C_1$–$C_6$-alkylthio, fluorine, chlorine or phenyl or A, B and the carbon atom that they are attached to particularly preferably represent $C_5$–$C_6$-cycloalkyl which is substituted by an alkylenediyl group optionally containing one or two not directly adjacent oxygen or sulphur atoms or by an alkylenedioxy group or by an alkylenedithiol group which forms together with the carbon atom that it is attached to a further five- to seven-membered ring or A, B and the carbon atom that they are attached to particularly preferably represent $C_3$–$C_6$-cycloalkyl or $C_5$–$C_6$-cycloaikenyl in which two carbon atoms are linked to each other by respectively optionally $C_1$–$C_4$-alkyl-, $C_1$–$C_4$-alkoxy-, fluorine-, chlorine- or bromine-substituted $C_3$–$C_5$-alkanediyl or $C_3$–$C_5$-alkenediyl, one methylene group in each case being optionally replaced by oxygen or sulphur, or are linked to each other by butadienediyl.

D particularly preferably represents hydrogen, particularly preferably represents respectively optionally fluorine- or chlorine-substituted $C_1$–$C_6$-alkyl or $C_1$–$C_6$-alkoxy, particularly preferably represents optionally fluorine-, chlorine-, $C_1$–$C_4$-alkyl-, $C_1$–$C_4$-alkoxy- or $C_1$–$C_2$-halogenoalkyl-substituted $C_3$–$C_7$-cycloalkyl in which optionally one or two not directly adjacent methylene groups are replaced by oxygen and/or sulphur, or particularly preferably represents respectively optionally fluorine-, chlorine-, bromine-, $C_1$–$C_2$-alkyl-, $C_1$–$C_2$-halogenoalkyl, $C_1$–$C_2$-alkoxy-, $C_1$–$C_2$-halogenoalkoxy-, cyano- or nitro-substituted phenyl, furanyl, imidazolyl, pyridyl, thiazolyl, pyrazolyl, pyrimidyl, pyrrolyl, thienyl, triazolyl or phenyl-$C_1$–$C_2$-alkyl or A and D together particularly preferably represent a $C_3$–$C_8$-alkanediyl or $C_3$–$C_5$-alkenediyl group in which in each case one methylene group is optionally replaced by oxygen or sulphur and which are optionally substituted by fluorine, chlorine or by respectively optionally fluorine- or chlorine-substituted $C_1$–$C_6$-alkyl, $C_1$–$C_4$-alkoxy, $C_1$–$C_4$-alkylthio. $C_3$–$C_6$-cycloalkyl, phenyl or benzyloxy or in which in each case optionally one of the following groups is contained:

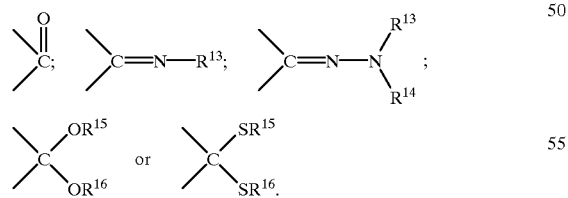

G particularly preferably represents hydrogen (a) or represents one of the groups

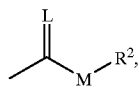

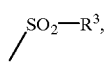

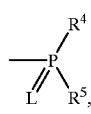

(f)

E or (g)

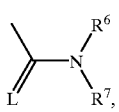

in which
E represents a metal ion equivalent or an ammonium ion,
L represents oxygen or sulphur and
M represents oxygen or sulphur.

$R^1$ particularly preferably represents respectively optionally fluorine- or chlorine-substituted $C_1$–$C_{16}$-alkyl, $C_2$–$C_{16}$-alkenyl, $C_1$–$C_6$-alkoxy-$C_1$–$C_6$-alkyl, $C_1$–$C_6$-alkylthio-$C_1$–$C_6$-alkyl or poly-$C_1$–$C_6$-alkoxy-$C_1$–$C_6$-alkyl or particularly preferably represents optionally fluorine-, chlorine-, $C_1$–$C_5$-alkyl- or $C_1$–$C_5$-alkoxy-substituted $C_3$–$C_7$-cycloalkyl in which optionally one or two not directly adjacent methylene groups are replaced by oxygen and/or sulphur, particularly preferably represents optionally fluorine-, chlorine-, bromine-, cyano-, nitro-, $C_1$–$C_4$-alkyl-, $C_1$–$C_4$-alkoxy-, $C_1$–$C_3$-halogenoalkyl-, $C_1$–$C_3$-halogenoalkoxy-, $C_1$–$C_4$-alkylthio- or $C_1$–$C_4$-alkylsulphonyl-substituted phenyl, particularly preferably represents optionally fluorine-, chlorine-, bromine-, $C_1$–$C_4$-alkyl-, $C_1$–$C_4$-alkoxy-, $C_1$–$C_3$-halogenoalkyl- or $C_1$–$C_3$-halogenoalkoxy-substituted phenyl-$C_1$–$C_4$-alkyl, particularly preferably represents respectively optionally fluorine-, chlorine-, bromine- or $C_1$–$C_4$-alkyl-substituted pyrazolyl, thiazolyl, pyridyl, pyrimidyl, furanyl or thienyl, particularly preferably represents optionally fluorine-, chlorine-, bromine- or $C_1$–$C_4$-alkyl-substituted phenoxy-$C_1$–$C_5$-alkyl or particularly preferably represents respectively optionally fluorine-, chlorine-, bromine-, amino- or $C_1$–$C_4$-alkyl-substituted pyridyloxy-$C_1$–$C_5$-alkyl, pyrimidyloxy-$C_1$–$C_5$-alkyl or thiazolyloxy-$C_1$–$C_5$-alkyl.

$R^2$ particularly preferably represents respectively optionally fluorine- or chlorine-substituted $C_1$–$C_{16}$-alkyl, $C_2$–$C_{16}$-alkenyl, $C_1$–$C_6$-alkoxy-$C_2$–$C_6$-alkyl or poly-$C_1$–$C_6$-alkoxy-$C_2$–$C_6$-alkyl, particularly preferably represents optionally fluorine-, chlorine-, $C_1$–$C_4$-alkyl- or $C_1$–$C_4$-alkoxy-substituted $C_3$–$C_7$-cycloalkyl or particularly preferably represents respectively optionally fluorine-, chlorine-, bromine-, cyano-, nitro-, $C_1$–$C_4$-alkyl-, $C_1$–$C_3$-alkoxy-, $C_1$–$C_3$-halogenoalkyl- or $C_1$–$C_3$-halogenoalkoxy-substituted phenyl or benzyl.

$R^3$ particularly preferably represents optionally fluorine- or chlorine-substituted $C_1$–$C_6$-alkyl or respectively optionally fluorine-, chlorine-, bromine-, $C_1$–$C_4$-alkyl-, $C_1$–$C_4$-alkoxy-, $C_1$–$C_2$-halogenoalkoxy-, $C_1$–$C_2$-halogenoalkyl-, cyano-, or nitro-substituted phenyl or benzyl.

$R^4$ and $R^5$ independently of one another each particularly preferably represent respectively optionally fluorine- or chlorine-substituted $C_1$–$C_6$-alkyl, $C_1$–$C_6$-alkoxy, $C_1$–$C_6$-alkylamino, di-($C_1$–$C_6$-alkyl)-amino, $C_1$–$C_6$-alkylthio or $C_3$–$C_4$-alkenylthio or particularly preferably represent respectively optionally fluorine-, chlorine-, bromine-, nitro-, cyano-, $C_1$–$C_3$-alkoxy-, $C_1$–$C_3$-haloge-noalkoxy-, $C_1$–$C_3$-alkylthio-, $C_1$–$C_3$-halogenoalkylthio-, $C_1$–$C_3$alkyl- or $C_1$–$C_3$-halogenoalkyl-substituted phenyl, phenoxy or phenylthio.

$R^6$ and $R^7$ independently of one another each particularly preferably represent hydrogen, particularly preferably represent respectively optionally fluorine -or chlorine-substituted $C_1$–$C_6$-alkyl, $C_3$–$C_6$-cycloalkyl, $C_1$–$C_6$-alkoxy, $C_3$–$C_6$-alkenyl or $C_1$–$C_6$-alkoxy-$C_2$–$C_6$-alkyl, particularly preferably represent respectively optionally fluorine-, chlorine-, bromine-, $C_1$–$C_5$-halogenoalkyl-, $C_1$–$C_5$-alkyl- or $C_1$–$C_5$-alkoxy-substituted phenyl or benzyl, or together particularly preferably represent an optionally $C_1$–$C_4$-alkyl-substituted $C_3$–$C_6$-alkylene radical in which optionally one methylene group is replaced by oxygen or sulphur.

$R^{13}$ particularly preferably represents hydrogen or respectively optionally fluorine- or chlorine-substituted $C_1$–$C_6$-alkyl or $C_1$–$C_6$-alkoxy, particularly preferably represents optionally fluorine-, $C_1$–$C_2$-alkyl- or $C_1$–$C_2$-alkoxy-substituted $C_3$–$C_7$-cycloalkyl in which optionally one methylene group is replaced by oxygen or sulphur, or particularly preferably represents respectively optionally fluorine-, chlorine-, bromine-, $C_1$–$C_5$-alkyl-, $C_1$–$C_5$-alkoxy-, $C_1$–$C_2$-halogenoalkyl-, $C_1$–$C_2$-halogenoalkoxy-, nitro- or cyano-substituted phenyl, phenyl-$C_1$–$C_3$-alkyl or phenyl-$C_1$–$C_2$-alkyloxy.

$R^{14}$ particularly preferably represents hydrogen or $C_1$–$C_6$-alkyl or $R^{13}$ and $R^{14}$ together particularly preferably represent $C_4$–$C_6$-alkanediyl.

$R^{15}$ and $R^{16}$ are identical or different and each particularly preferably represent $C_1$–$C_4$-alkyl or $R^{15}$ and $R^{16}$ together particularly preferably represent a $C_2$–$C_3$-alkanediyl radical which is optionally substituted by $C_1$–$C_4$-alkyl or by optionally fluorine-, chlorine-, bromine-, $C_1$–$C_2$-alkyl-, $C_1$–$C_2$-halogenoalkyl-, $C_1$–$C_2$-alkoxy-, $C_1$–$C_2$-halogenoalkoxy-, nitro- or cyano-substituted phenyl.

X very particularly preferably represents fluorine, chlorine, bromine, methyl, ethyl, n-propyl, iso-propyl, n-butyl, iso-butyl, tert-butyl, methoxy, ethoxy, n-propoxy, iso-propoxy, trifluoromethyl, trifluoromethoxy, difluoromethoxy, cyano or nitro, Z very particularly preferably represents hydrogen, amino, fluorine, chlorine, bromine, methyl, ethyl, n-propyl, iso-propyl, n-butyl, iso-butyl, tert-butyl, methoxy, ethoxy, n-propoxy, iso-propoxy, trifluoromethyl, trifluoro-methoxy, difluoromethoxy, cyano or nitro.

Het very particularly preferably represents one of the groups

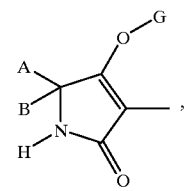

(1)

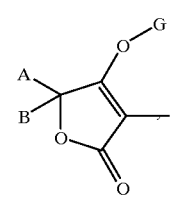

(2)

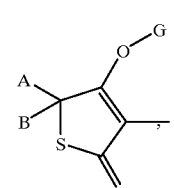

(3)

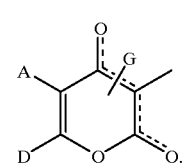

(4)

A very particularly preferably represents respectively optionally fluorine- or chlorine-substituted $C_1$–$C_8$-alkyl, $C_2$–$C_4$-alkenyl, $C_1$–$C_6$-alkoxy-$C_1$–$C_4$-alkyl, poly-$C_1$–$C_4$-alkoxy-$C_1$–$C_4$-alkyl or $C_1$–$C_6$-alkylthio-$C_1$–$C_4$-alkyl, or very particularly preferably represents optionally fluorine-, chlorine-, methyl- or methoxy-substituted $C_3$–$C_6$-cycloalkyl in which optionally one or two not directly adjacent methylene groups are replaced by oxygen and/or sulphur, or very particularly preferably represents respectively optionally fluorine-, chlorine-, bromine-, methyl-, ethyl-, n-propyl-, iso-propyl-, methoxy-, ethoxy-, trifluoromethyl-, trifluoromethoxy-, cyano- or nitro-substituted phenyl, pyridyl or benzyl.

B very particularly preferably represents $C_1$–$C_8$-alkyl or $C_1$–$C_4$-alkoxy-$C_1$–$C_2$-alkyl or A, B and the carbon atom that they are attached to very particularly preferably represent $C_3$–$C_8$-cycloalkyl or $C_5$–$C_8$-cycloalkenyl in which in each case optionally one methylene group is replaced by oxygen or sulphur and which are optionally substituted by methyl, ethyl, n-propyl, iso-propyl, butyl, iso-butyl, sec-butyl, tert-butyl, cyclohexyl, trifluoromethyl, methoxy, ethoxy, n-propoxy, iso-propoxy, butoxy, iso-butoxy, sec-butoxy, tert-butoxy, methylthio, ethylthio, fluorine, chlorine or phenyl or A, B and the carbon atom that they are attached to very particularly preferably represent $C_3$–$C_6$-cycloalkyl or $C_5$–$C_6$-cycloalkenyl in which two carbon atoms are linked together by $C_3$–$C_4$-alkanediyl or $C_3$–$C_4$-alkenediyl in which in each case optionally one methylene group is replaced by oxygen or sulphur, or are linked together by butadienediyl.

D very particularly preferably represents hydrogen, very particularly preferably represents respectively optionally fluorine-substituted $C_1$–$C_4$-alkyl or $C_1$–$C_4$-alkoxy or $C_3$–$C_6$-cycloalkyl in which optionally one or two not directly adjacent methylene groups are replaced by oxygen and/or sulphur, or very particularly preferably represents respectively optionally fluorine-, chlorine-, bromine-, methyl-, ethyl-, n-propyl-, iso-propyl-, methoxy-, ethoxy-, trifluoromethyl-, trifluoromethoxy-, cyano- or nitro-substituted phenyl, furanyl, pyridyl, thienyl or benzyl, or A and D together very particularly preferably represent a $C_3$–$C_5$-alkanediyl or $C_3$–$C_5$-alkenediyl group in which in each case optionally one methylene group is replaced by oxygen or sulphur and which are optionally substituted by fluorine, chlorine or by respectively optionally fluorine- or chlorine-substituted $C_1$–$C_6$-alkyl, $C_1$–$C_4$-alkoxy, $C_1$–$C_4$-alkylthio, $C_3$–$C_6$-cycloalkyl, phenyl or benzyloxy.

G very particularly preferably represents hydrogen (a) or represents one of the groups

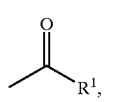
(b)

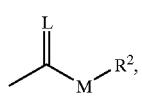
(c)

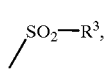
(d)

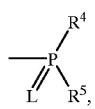
(e)

E or
(f)

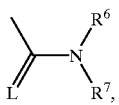
(g)

in which
E represents a metal ion equivalent or an ammonium ion,
L represents oxygen or sulphur and
M represents oxygen or sulphur.

$R^1$ very particularly preferably represents respectively optionally fluorine- or chlorine-substituted $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl, poly-$C_1$–$C_4$-alkoxy-$C_1$–$C_4$-alkyl or very particularly preferably represents optionally fluorine-, chlorine-, methyl-, ethyl-, n-propyl-, i-propyl-, n-butyl-, i-butyl-, tert-butyl-, methoxy-, ethoxy-, n-propoxy- or iso-propoxy-substituted $C_3$–$C_6$-cycloalkyl in which optionally one or two not directly adjacent methylene groups are replaced by oxygen and/or sulphur, very particularly preferably represents optionally fluorine-, chlorine-, bromine-, cyano-, nitro-, methyl-, ethyl-, n-propyl-, i-propyl-, methoxy-, ethoxy-, trifluoromethyl-, trifluoromethoxy-, methylthio-, ethylthio-, methylsulphonyl- or ethylsulphonyl-substituted phenyl, very particularly preferably represents optionally fluorine-, chlorine-, bromine-, methyl-, ethyl-, n-propyl-, i-propyl-, methoxy-, ethoxy-, trifluoromethyl- or trifluoromethoxy-substituted benzyl, very particularly preferably represents respectively optionally fluorine-, chlorine-, bromine-, methyl- or ethyl-substituted furanyl, thienyl or pyridyl, very particularly preferably represents optionally fluorine-, chlorine-, methyl- or ethyl-substituted phenoxy-$C_1$–$C_4$-alkyl or very particularly preferably represents respectively optionally fluorine-, chlorine-, amino-, methyl- or ethyl-substituted pyridyloxy-$C_1$–$C_4$-alkyl, pyrimidyloxy-$C_1$–$C_4$-alkyl or thiazolyloxy-$C_1$–$C_4$-alkyl $R^2$ very particularly preferably represents respectively optionally fluorine- or chlorine-substituted $C_1$–$C_{14}$-alkyl, $C_2$–$C_{14}$-alkenyl, $C_1$–$C_4$-alkoxy-$C_2$–$C_6$-alkyl or poly-$C_1$–$C_4$-alkoxy-$C_2$–$C_6$-alkyl, very particularly preferably represents optionally fluorine-, chlorine-, methyl-, ethyl-, n-propyl-, iso-propyl- or methoxy-substituted $C_3$–$C_6$-cycloalkyl, or very particularly preferably represents respectively optionally fluorine-, chlorine-, cyano-, nitro-, methyl-, ethyl-, n-propyl-, i-propyl-, methoxy-, ethoxy-, trifluoromethyl- or trifluoromethoxy-substituted phenyl or benzy.

$R^3$ very particularly preferably represents optionally fluorine- or chlorine-substituted methyl, ethyl, propyl, iso-propyl, n-butyl, tert-butyl or respectively optionally fluorine-, chlorine-, bromine-, methyl-, ethyl-, iso-propyl-, tert-butyl-, methoxy-, ethoxy-, iso-propoxy-, trifluoromethyl-, trifluoromethoxy-, cyano- or nitro-substituted phenyl or benzyl.

$R^4$ and $R^5$ independently of one another each very particularly preferably represent respectively optionally fluorine- or chlorine-substituted $C_1$–$C_4$-alkyl, $C_1$–$C_4$-alkoxy, $C_1$–$C_4$-alkylamino, di-($C_1$–$C_4$-alkyl)-amino or $C_1$–$C_4$-alkylthio or very particularly preferably represent respectively optionally fluorine-, chlorine-, bromine-, nitro-, cyano-, methyl-, methoxy-, trifluoromethyl- or trifluoromethoxy-substituted phenyl, phenoxy or phenylthio.

$R^6$ and $R^7$ independently of one another each very particularly preferably represent hydrogen, very particularly preferably represent respectively optionally fluorine- or chlorine-substituted $C_1$–$C_4$-alkyl, $C_3$–$C_6$-cycloalkyl, $C_1$–$C_4$-alkoxy, $C_3$–$C_4$-alkenyl or $C_1$–$C_4$-alkoxy-$C_2$–$C_4$-alkyl, very particularly preferably represent respectively optionally fluorine-, chlorine-, bromine-, methyl-, methoxy- or trifluoromethyl-substituted phenyl or benzyl, or together very particularly preferably represent an optionally methyl- or ethyl-substituted $C_5$–$C_6$-alkylene radical in which optionally one methylene group is replaced by oxygen or sulphur.

Particular preference is given to compounds of the formula (I) in which Z does not represent hydrogen.

Preference is also given to those compounds where D does not represent methyl.

The abovementioned definitions or illustrations of radicals mentioned generally or in preferred ranges can be combined with each other as desired, i.e. also between the respective ranges and preferred ranges. They apply correspondingly to the final products and to the precursors and intermediates.

For the purpose of the invention, preference is given to compounds of the formula (I) in which there exists a combination of the meanings mentioned above as preferred (preferably).

For the purpose of the invention, particular preference is given to compounds of the formula (I) in which there exists a combination of the meanings mentioned above as particularly preferred.

For the purpose of the invention, very particular preference is given to compounds of the formula (I) in which there exists a combination of the meanings mentioned above as very particularly preferred.

Saturated or unsaturated hydrocarbon radicals such as alkyl or alkenyl can, as far as possible, in each case be straight-chain or branched, also in combination with hetero atoms, for example in alkoxy.

Optionally substituted radicals can be mono- or polysubstituted, it being possible in the case of polysubstitution for the substituents to be identical or different.

In addition to the compounds mentioned in the Preparation Examples, the following compounds of the formula (I-1-a) may be specifically mentioned:

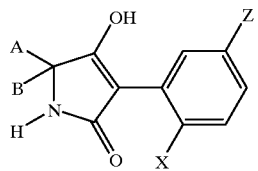

TABLE 1

| X = $CH_3$; Z = $CH_3$ | |
|---|---|
| A | B |
| $CH_3$ | $CH_3$ |
| $C_2H_5$ | $CH_3$ |
| $C_3H_7$ | $CH_3$ |
| i-$C_3H_7$ | $CH_3$ |
| $C_4H_9$ | $CH_3$ |
| i-$C_4H_9$ | $CH_3$ |
| s-$C_4H_9$ | $CH_3$ |
| t-$C_4H_9$ | $CH_3$ |
| $C_2H_5$ | $C_2H_5$ |
| $C_3H_7$ | $C_3H_7$ |
| cyclopropyl | $CH_3$ |
| cyclopentyl | $CH_3$ |
| cyclohexyl | $CH_3$ |
| —$(CH_2)_2$— | |
| —$(CH_2)_4$— | |
| —$(CH_2)_5$— | |
| —$(CH_2)_6$— | |
| —$(CH_2)_7$— | |
| —$(CH_2)_2$—O—$(CH_2)_2$— | |
| —$(CH_2)_2$—S—$(CH_2)_2$— | |

TABLE 1-continued

| X = $CH_3$; Z = $CH_3$ | |
|---|---|
| A | B |
| —$CH_2$—$CHCH_3$—$(CH_2)_3$— | |
| —$(CH_2)_2$—$CHCH_3$—$(CH_2)_2$— | |
| —$(CH_2)_2$—$CHC_2H_5$—$(CH_2)_2$— | |
| —$(CH_2)_2$—$CHC_3H_7$—$(CH_2)_2$— | |
| —$(CH_2)_2$—CHi—$C_3H_7$—$(CH_2)_2$— | |
| —$(CH_2)_2$—$CHOCH_3$—$(CH_2)_2$— | |
| —$(CH_2)_2$—$CHOC_2H_5$—$(CH_2)_2$— | |
| —$(CH_2)_2$—$CHOC_3H_7$—$(CH_2)_2$— | |
| —$(CH_2)_2$—CHiO—$C_3H_7$—$(CH_2)_2$— | |
| —$(CH_2)_2$—C($CH_3$)$_2$—$(CH_2)_2$— | |
| —$CH_2$—$(CHCH_3)_2$—$(CH_2)_2$— | |
| —$CH_2$—CH—$(CH_2)_2$—CH— bridged by —$CH_2$— | |
| —$CH_2$—CH—CH—$CH_2$— bridged by —$(CH_2)_4$— | |
| —$CH_2$—CH—CH—$(CH_2)_2$— bridged by —$(CH_2)_3$— | |
| indane | |
| tetralin | |

Table 2
A and B are each as defined in Table 1 with

X=$CH_3$; Z=Cl

Table 3
A and B are each as defined in Table 1 with

X=Cl; Z=$CH_3$

In addition to the compounds mentioned in the preparation examples, the following compounds of the formula (I-2-a) may be specifically mentioned:

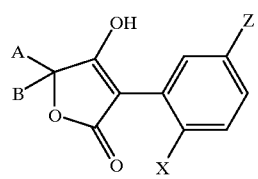

TABLE 4

| X = $CH_3$; Z = $CH_3$ | |
|---|---|
| A | B |
| $CH_3$ | $CH_3$ |
| $C_2H_5$ | $CH_3$ |

TABLE 4-continued

X = CH₃; Z = CH₃

| A | B |
|---|---|
| C₃H₇ | CH₃ |
| i-C₃H₇ | CH₃ |
| C₄H₉ | CH₃ |
| i-C₄H₉ | CH₃ |
| s-C₄H₉ | CH₃ |
| t-C₄H₉ | CH₃ |
| C₂H₅ | C₂H₅ |
| C₃H₇ | C₃H₇ |
| cyclopropyl | CH₃ |
| cyclopentyl | CH₃ |
| cyclohexyl | CH₃ |
| —(CH₂)₂— | |
| —(CH₂)₄— | |
| —(CH₂)₅— | |
| —(CH₂)₆— | |
| —(CH₂)₇— | |
| —(CH₂)₂—O—(CH₂)₂— | |
| —(CH₂)₂—S—(CH₂)₂— | |
| —CH₂—CHCH₃—(CH₂)₃— | |
| —(CH₂)₂—CHCH₃—(CH₂)₂— | |
| —(CH₂)₂—CHC₂H₅—(CH₂)₂— | |
| —(CH₂)₂—CHC₃H₇—(CH₂)₂— | |
| —(CH₂)₂—CHi—C₃H₇—(CH₂)₂— | |
| —(CH₂)₂—CHOCH₃—(CH₂)₂— | |
| —(CH₂)₂—CHOC₂H₅—(CH₂)₂— | |
| —(CH₂)₂—CHOC₃H₇—(CH₂)₂— | |
| —(CH₂)₂—CHiO—C₃H₇—(CH₂)₂— | |
| —(CH₂)₂—C(CH₃)₂—(CH₂)₂— | |
| —CH₂—(CHCH₃)₂—(CH₂)₂— | |
| —CH₂—CH—(CH₂)₂—CH— with —CH₂— bridge | |
| —CH₂—CH—CH—CH₂— with —(CH₂)₄— bridge | |
| —CH₂—CH—CH—(CH₂)₂— with —(CH₂)₃— bridge | |
| indanyl | |
| tetrahydronaphthyl | |

Table 5

A and B are each as defined in Table 4 with

X=CH₃; Z=Cl

Table 6

A and B are each as defined in Table 4 with

X=Cl; Z=CH₃

In addition to the compounds mentioned in the preparation examples, the following compounds of the formula (I-3-a) may be specifically mentioned:

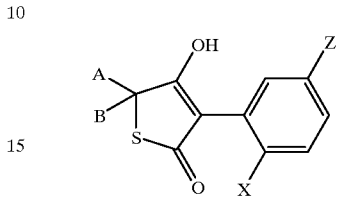

TABLE 7

X = CH₃; Z = CH₃

| A | B |
|---|---|
| CH₃ | CH₃ |
| C₂H₅ | CH₃ |
| C₃H₇ | CH₃ |
| i-C₃H₇ | CH₃ |
| C₄H₉ | CH₃ |
| i-C₄H₉ | CH₃ |
| s-C₄H₉ | CH₃ |
| t-C₄H₉ | CH₃ |
| C₂H₅ | C₂H₅ |
| C₃H₇ | C₃H₇ |
| cyclopropyl | CH₃ |
| cyclopentyl | CH₃ |
| cyclohexyl | CH₃ |
| —(CH₂)₂— | |
| —(CH₂)₄— | |
| —(CH₂)₅— | |
| —(CH₂)₆— | |
| —(CH₂)₇— | |
| —(CH₂)₂—O—(CH₂)₂— | |
| —(CH₂)₂—S—(CH₂)₂— | |
| —CH₂—CHCH₃—(CH₂)₃— | |
| —(CH₂)₂—CHCH₃—(CH₂)₂— | |
| —(CH₂)₂—CHC₂H₅—(CH₂)₂— | |
| —(CH₂)₂—CHC₃H₇—(CH₂)₂— | |
| —(CH₂)₂—CHi—C₃H₇—(CH₂)₂— | |
| —(CH₂)₂—CHOCH₃—(CH₂)₂— | |
| —(CH₂)₂—CHOC₂H₅—(CH₂)₂— | |
| —(CH₂)₂—CHOC₃H₇—(CH₂)₂— | |
| —(CH₂)₂—CHiO—C₃H₇—(CH₂)₂— | |
| —(CH₂)₂—C(CH₃)₂—(CH₂)₂— | |
| —CH₂—(CHCH₃)₂—(CH₂)₂— | |
| —CH₂—CH—(CH₂)₂—CH— with —CH₂— bridge | |
| —CH₂—CH—CH—CH₂— with —(CH₂)₄— bridge | |

TABLE 7-continued

X = CH₃; Z = CH₃

| A | B |
|---|---|
| —CH₂—CH———CH—(CH₂)₂— <br> └—(CH₂)₃—┘ | |

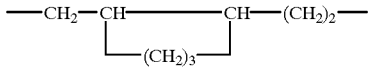

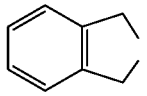

Table 8

A and B are each as defined in Table 7 with

X=CH₃; Z=Cl

Table 9

A and B are each as defined in Table 7 with

X=Cl; Z=CH₃

In addition to the compounds mentioned in the Preparation Examples, the following compounds of the formula (I-4-a) may be specifically mentioned:

TABLE 10

X = CH₃; Z = CH₃

| A | D |
|---|---|
| CH₃ | 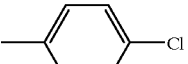 |
| CH₃ | 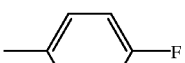 |
| CH₃ |  |
| CH₃ | 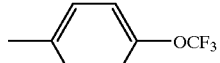 |

TABLE 10-continued

X = CH₃; Z = CH₃

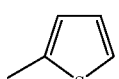

| A | D |
|---|---|
| CH₃ | 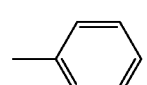 |
| CH₃ | 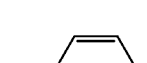 |
| CH₃ | 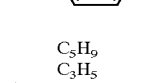 |
| CH₃ | 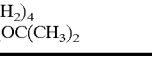 |
| CH₃ | C₅H₉ |
| CH₃ | C₃H₅ |
| (CH₂)₃ | |
| (CH₂)₄ | |
| C(CH₃)₂OC(CH₃)₂ | |

Table 11

A and D are each as defined in Table 10 with

X=CH₃; Z=Cl

Table 12

A and D are each as defined in Table 10 with

X=Cl; Z=CH₃

If according to process (A) ethyl N-[(3-chloro-6-methyl)-phenylacetyl]-1amino-4-ethyl-cyclohexane-carboxylate is used as starting material, the course of the process according to the invention can be represented by the following reaction scheme:

 

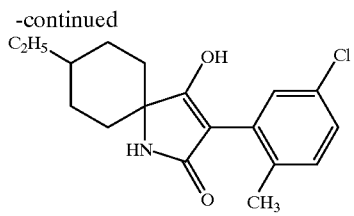

If according to process (B) ethyl O-[(2,5-dichloro)-phenylacetyl]-2-hydroxy-isobutyrate is used, the course of the process according to the invention can be represented by the following reaction scheme:

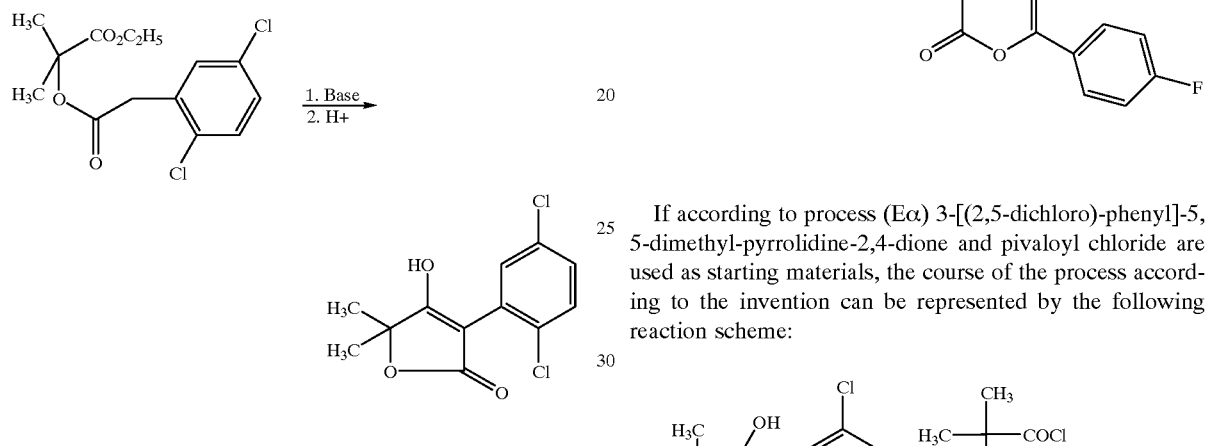

If according to process (C) ethyl 2-[(2-chloro-5-methyl)-phenyl]-4-(4-methoxy)benzylmercapto-4-methyl-3-oxo-valerate is used, the course of the process according to the invention can be represented by the following reaction scheme:

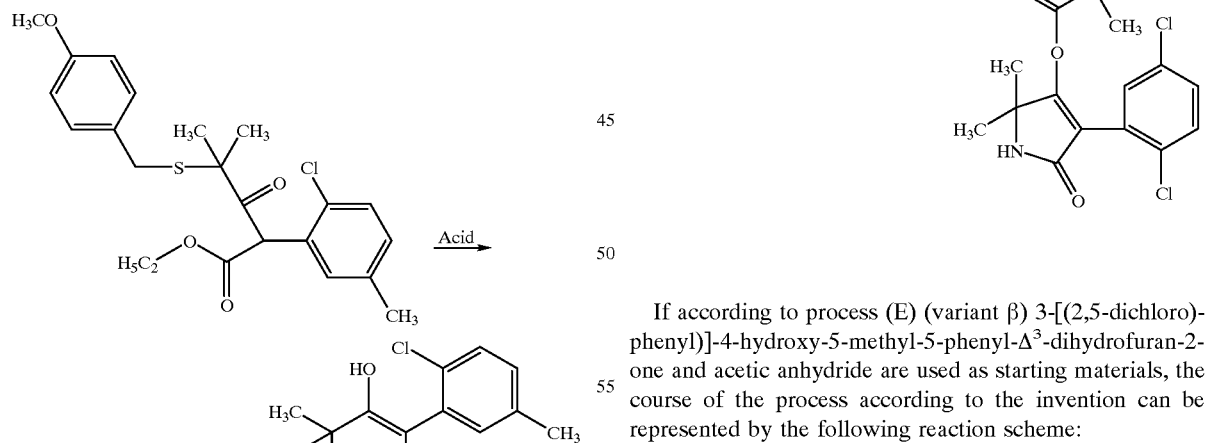

If, for example, according to process (D) (chlorocarbonyl)-2-[(3-chloro-6-methyl)phenyl]-ketene and 4-fluoro-propiophenone are used as starting materials, the course of the process according to the invention can be represented by the following reaction scheme:

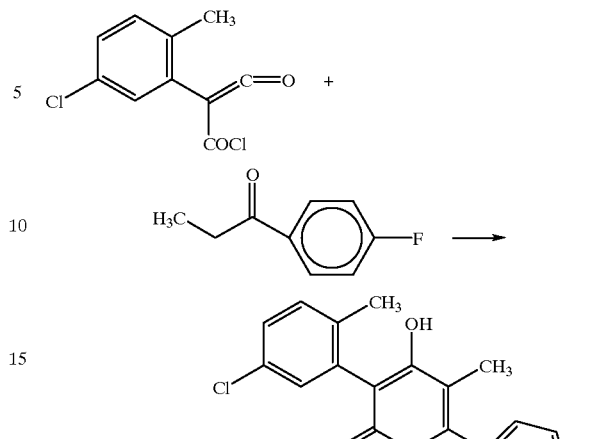

If according to process (Eα) 3-[(2,5-dichloro)-phenyl]-5,5-dimethyl-pyrrolidine-2,4-dione and pivaloyl chloride are used as starting materials, the course of the process according to the invention can be represented by the following reaction scheme:

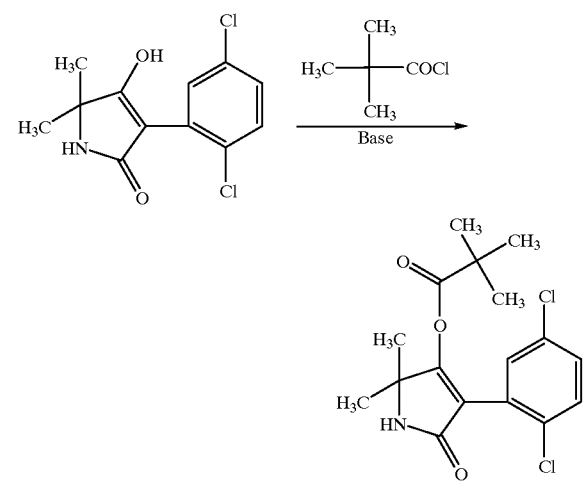

If according to process (E) (variant β) 3-[(2,5-dichloro)-phenyl)]-4-hydroxy-5-methyl-5-phenyl-Δ³-dihydrofuran-2-one and acetic anhydride are used as starting materials, the course of the process according to the invention can be represented by the following reaction scheme:

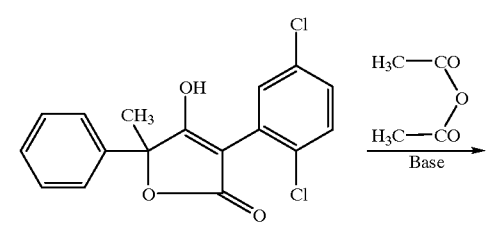

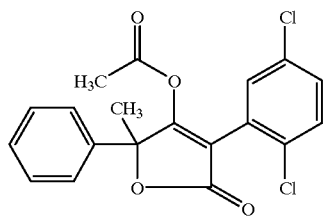

If according to process (F) 8-[(2-chloro-5-methyl)-phenyl]-5,5-pentamethylenepyrrolidine-2,4-dione and ethoxyethyl chloroformate are used as starting materials, the course of the process according to the invention can be represented by the following reaction scheme:

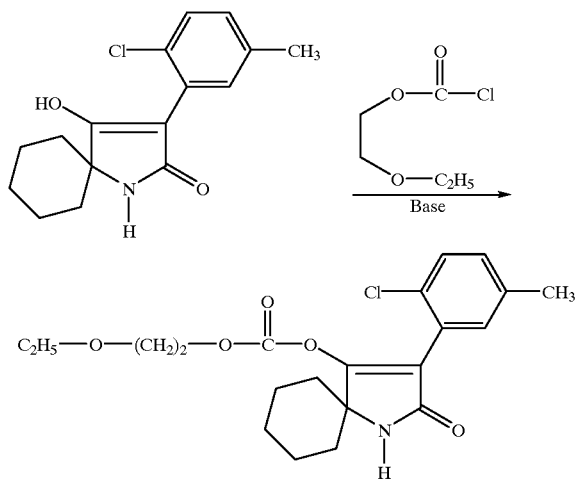

If according to process (G) 3-[(2-bromo-5-methyl)-phenyl]-4-hydroxy-5-methyl-6-(3-pyridyl)-pyrone and methyl chloromonothioformate are used as starting materials, the course of the reaction can be represented in the following manner:

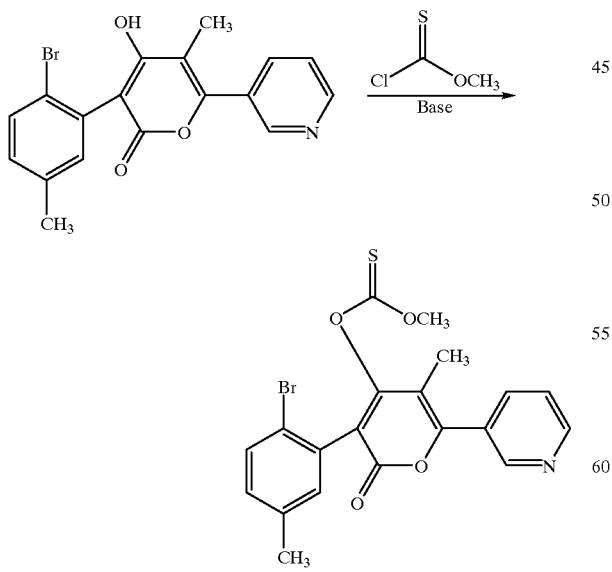

If according to process (H) 2-[(2,5-dimethyl)-phenyl]-5,5-[(3-methyl)-pentamethylene]pyrrolidine-2,4-dione and methanesulphonyl chloride are used as starting materials, the course of the reaction can be represented by the following reaction scheme:

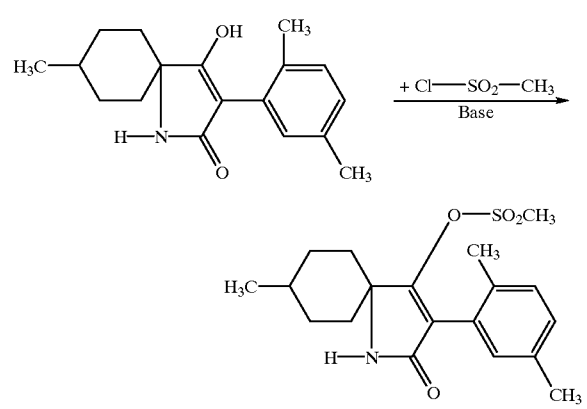

If according to process (I) 2-[(2-chloro-5-methyl)-phenyl]-4-hydroxy-5-methyl-6-(2-pyridyl)-pyrone and 2,2,2-trifluoroethyl chloromethanethio-phosphonate are used as starting materials, the course of the reaction can be represented by the following reaction scheme:

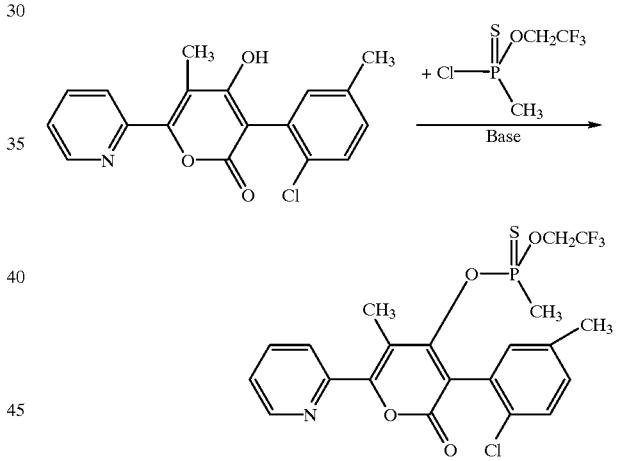

If according to process (J) 3-[(2,5-dichloro)-phenyl]-5-cyclopropyl-5-methyl-pyrrolidine-2,4-dione and NaOH are used as components, the course of the process according to the invention can be represented by the following reaction scheme:

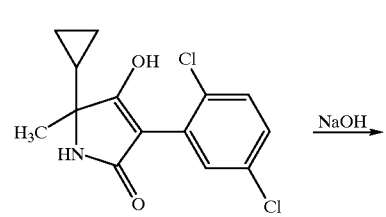

-continued

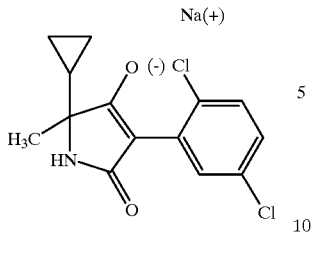

If according to process (K) (variant α) 3[(2-chloro-5-methyl)-phenyl]-4-hydroxy-5,5-tetramethylene-Δ³-dihydro-furan-2-one and ethyl isocyanate are used as starting materials, the course of the reaction can be represented by the following reaction scheme:

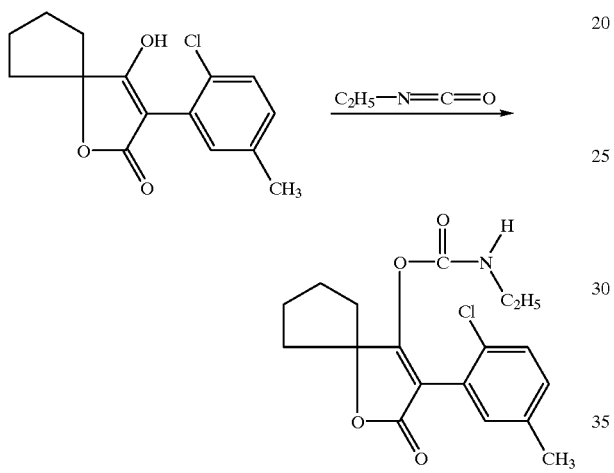

If according to process (K) (variant β) 3-[(2-chloro-5-methyl)-phenyl]-5,5-dimethyl-pyrrolidine-2,4-dione and dimethylcarbamoyl chloride are used as starting materials, the course of the reaction can be represented by the following scheme:

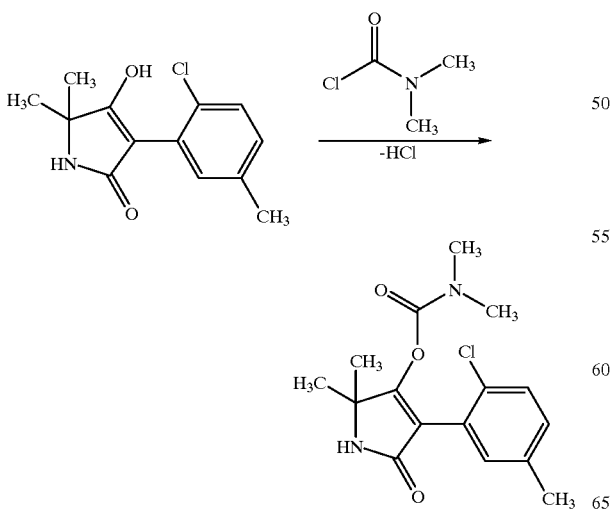

The compounds of the formula (II)

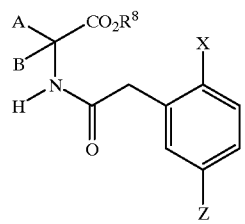

(II)

in which

A, B, X, Z and R⁸ are each as defined above, required as starting materials in process (A) according to the invention are novel.

The acylamino acid esters of the formula (II) are obtained, for example, when amino acid derivatives of the formula (XVIII)

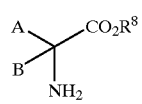

(XVIII)

in which

A, B and R⁸ are as defined above, are acylated using substituted phenylacetyl halides of the formula (XIX)

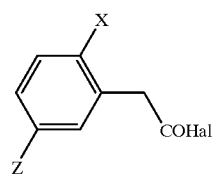

(XIX)

in which

X and Z are each as defined above and

Hal represents chlorine or bromine, (Chem. Reviews 52, 237–416 (1953); Bhattacharya, Indian J. Chem. 6, 341–5, 1968) or when acylamino acids of the formula (XX)

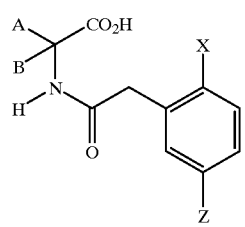

(XX)

in which

A, B, X and Z are each as defined above, are esterified (Chem. Ind. (London) 1568 (1968)).

The compounds of the formula (XX)

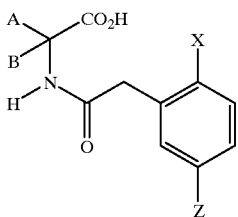

(XX)

in which

A, B, X and Z are each as defined above, are novel.

The compounds of the formula (XX) are obtained when amino acids of the formula (XXI)

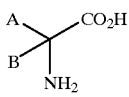

(XXI)

in which

A and B are each as defined above, are acylated using substituted phenylacetyl halides of the formula (XIX)

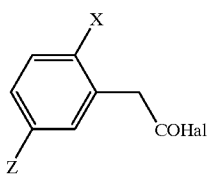

(XIX)

in which

X and Z are each as defined above and

Hal represents chlorine or bromine, according to Schotten-Baumann (Organikum, VEB Deutscher Verlag der Wissenschaften, Berlin 1977, p. 505).

Some of the compounds of the formula (XlX) are novel. They can be prepared by known methods.

The compounds of the formula (XIX) are obtained, for example, by reacting substituted phenylacetic acids of the formula (XXXII)

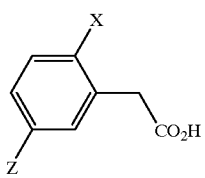

(XXII)

in which

X and Z are each as defined above, with halogenating agents (for example thionyl chloride, thionyl bromide, oxalyl chloride, phosgene, phosphorus trichloride, phosphorus tribromide or phosphorus pentachloride), if appropriate in the presence of a diluent (for example optionally chlorinated aliphatic or aromatic hydrocarbons such as toluene or methylene chloride) at temperatures from −20° C. to 150° C., preferably from −10° C. to 100° C.

The compounds of the formula (XXII) are novel with the exception of 2,5-dichlorophenylacetic acid (CAS 5398798), 5-chloro-2-methoxyphenylacetic acid (CAS 7569-6-22), 2-chloro-5-methylphenylacetic acid (CAS 81682-39-5), 2,5-difluorophenylacetic acid (CAS 85068-27-5), 2-bromo-5-methylphenylacetic acid (BRN 3 249 577) and 2-chloro-5-trifluoromethylphenylacetic acid (CAS 22893-39-6), they can be prepared by methods known from the literature (Organikum, 15th edition, p. 533, VEB Deutscher Verlag der Wissenschaften, Berlin 1977). The compounds of the formula (XXII) are obtained, for example, by hydrolysing substituted phenylacetic acid esters of the formula (XXIII)

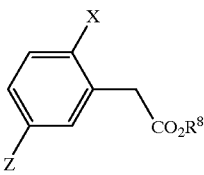

(XXIII)

in which

X, Z and $R^8$ are each as defined above, at temperatures between 0° C. and 150° C., preferably between 20° C. and 100° C., in the presence of an acid (for example an inorganic acid such as hydrochloric acid) or of a base (for example of an alkali metal hydroxide such as sodium hydroxide or potassium hydroxide) and, if appropriate, of a diluent (for example of an aqueous alcohol such as methanol or ethanol).

The compounds of the formula (XXIII) are novel with the exception of methyl 2,5-dichlorophenylacetate (CAS 96129-66-7) and methyl 5-chloro-2-methoxy-phenylacetate (CAS 26939-01-5), they can be prepared by methods known in principle.

The compounds of the formula (XXIII) are obtained, for example, by reacting substituted 1,1,1-trichloro-2-phenylethanes of the formula (XXIV)

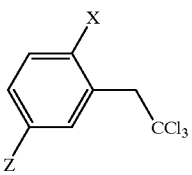

(XXIV)

in which

X and Z are each as defined above, first with alkoxides (for example alkali metal alkoxides such as sodium methoxide or sodium ethoxide) in the presence of a diluent (for example the alcohol derived from the alkoxide) at temperatures between 0° C. and 150° C., preferably between 20° C. and 120° C., and then reacting with an acid (preferably an inorganic acid, such as sulphuric acid) at temperatures between −20° C. and 150° C., preferably 0° C. and 100° C. (cf. DE 3 314 249).

The compounds of the formula (XXIV) are novel, they can be prepared by methods known in principle.

The compounds of the formula (XXIV) are obtained, for example, when anilines of the formula (XXV)

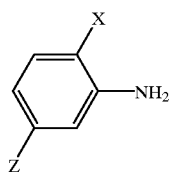

(XXV)

in which

X and Z are as defined above, are reacted with vinylidene chloride (CH$_2$=CC$_2$) in the presence of an alkyl nitrite of the formula (XXVI)

$R^{21}$—ONO (XXVI)

in which $R^{21}$ represents alkyl, preferably C$_1$–C$_6$-alkyl, in the presence of copper(II) chloride and, if appropriate, in the presence of a diluent (for example of an aliphatic nitrile such as acetonitrile) at a temperature of –20° C. to 80° C., preferably 0° C. to 60° C.

The compounds of the formulae (XXV) and (XXVI) are known compounds of organic chemistry. Copper(II) chloride and vinylidene chloride have long been known and are commercially available.

Some of the compounds of the formulae (XVIII) and (XXI) are known and/or they can be prepared by known processes (see, for example, Compagnon, Miocque Ann. Chim. (Paris) [14]5, p. 11–22, 23–27 (1970)).

The substituted cyclic aminocarboxylic acids of the formula (XXIa), in which A and B form a ring, are in general obtainable by the Bucherer-Bergs synthesis or by the Strecker synthesis and are in each case obtained here in different isomeric forms. Thus, according to the conditions of the Bucherer-Bergs synthesis mainly the isomers (in the following designated as β for the sake of simplicity) in which the radicals R and the carboxyl group are equatorial are obtained, while according to the conditions of the Strecker synthesis mainly the isomers (in the following designated as α for the sake of simplicity) are obtained in which the amino group and the radicals R are equatorial.

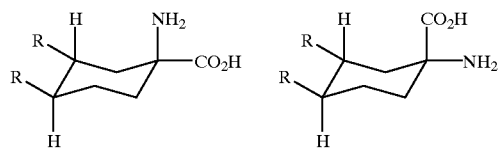

Bucherer-Bergs synthesis
(β-isomer)
Strecker synthesis
(α-isomer)
(L. Munday, J. Chem. Soc. 4372 (1961); J. T. Eward, C. Jitrangeri, Can. J. Chem. 53, 3339 (1975).

Furthermore the starting materials of the formula (II)

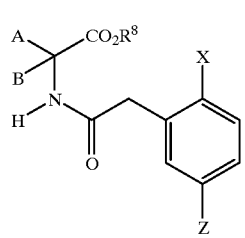

(II)

in which

A, B, X, Z and $R^8$ are each as defined above, used in the above process (A) can be prepared by reacting aminonitriles of the formula (XXVII)

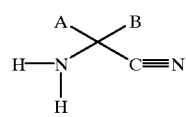

(XXVII)

in which

A and B are each as defined above, with substituted phenylacetyl halides of the formula (XIX)

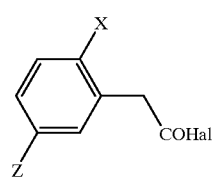

(XIX)

in which

X, Z and Hal are each as defined above, to give compounds of the formula (XXVIII)

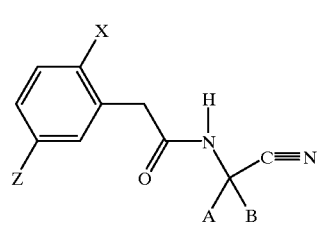

(XXVIII)

in which

A, B, X and Z are each as defined above, and then subjecting these to an acidic alcoholysis.

The compounds of the formula (XXVIII) are also novel.

The compounds of the formula (III)

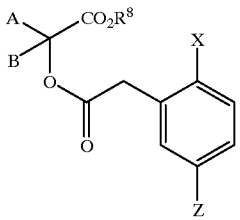
(III)

in which

A, B, X, Z and $R^8$ are each as defined above, required as starting materials in process (B) according to the invention are novel.

They can be prepared in a simple manner by methods known in principle.

The compounds of the formula (III) are obtained, for example, when 2-hydroxycarboxylic acid esters of the formula (XXIX)

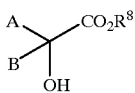
(XXIX)

in which

A, B and $R^8$ are each as defined above, are acylated using substituted phenylacetyl halides of the formula (XIX)

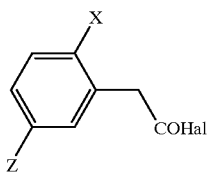
(XIX)

in which

X, Z and Hal are each as defined above (Chem. Reviews 52, 237–416 (1953)).

The compounds of the formula (IV)

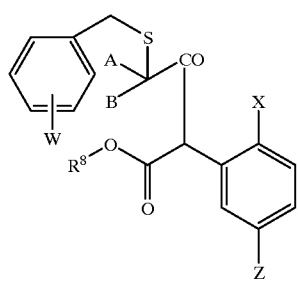
(IV)

in which

A, B, W, X, Z and $R^8$ are each as defined above, required as starting materials in the above process (C) are novel. They can be prepared by methods known in principle.

The compounds of the formula (IV) are obtained for example, when substituted phenylacetic acid esters of the formula (XXIII)

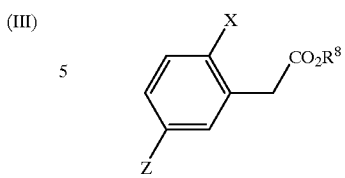
(XXIII)

in which

X, $R^8$ and Z are each as defined above, are acylated using 2-benzylthio-carbonyl halides of the formula (XXX)

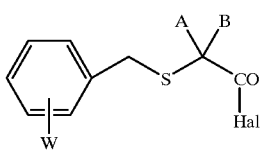
(XXX)

in which

A, B and W are each as defined above and

Hal represents halogen (in particular chlorine or bromine), in the presence of strong bases (see, for example, M. S. Chambers, E. J. Thomas, D. J. Williams, J. Chem. Soc. Chem. Commun., (1987), 1228).

The benzylthio-carbonyl halides of the formula (XXX) are known in some cases and/or can be prepared by known methods (J. Antibiotics (1983), 26, 1589).

The halogenocarbonylketenes of the formula (VI) in which Z does not represent hydrogen, which are required as starting materials in process (D), are novel. They can be prepared in a simple manner by methods known in principle (cf., for example, Org. Prep. Proced. Int., 7, (4), 155–158, 1975 and DE 1 945 703).

The compounds of the formula (VI)

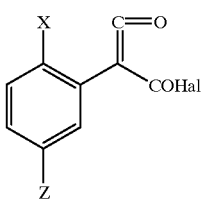
(VI)

in which

X and Z are each as defined above and

Hal represents chlorine or bromine, are obtained when substituted phenylmalonic acids of the formula (XXXI)

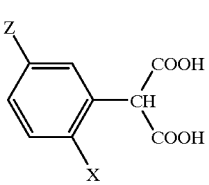
(XXXI)

in which

X and Z are each as defined above, are reacted with acid halides, for example thionyl chloride, phosphorus(V) chloride, phosphorus(III) chloride, oxalyl chloride, phosgene or thionyl bromide, if appropriate in the presence of catalysts, for example diethylformamide, methylstearylformamide or triphenylphosphine and, if appropriate, in the presence of bases, for example pyridine or triethylamine, at a temperature between −20° C. and 200° C., preferably between 0° C. and 150° C.

The substituted phenylmalonic acids of the formula (XXXI) in which Z does not represent hydrogen are novel. However, they may be prepared in a simple manner by known processes (cf., for example, Organikum, VEB Deutscher Verlag der Wissenschaften, Berlin 1977, p. 517 ff), for example by hydrolysis of substituted phenylmalonic esters of the formula (XXXII)

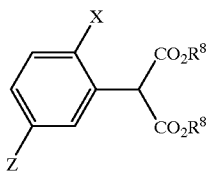

(XXXII)

in which

X, Z and $R^8$ are each as defined above.

The carbonyl compounds of the formula (V) or their silyl enole ethers of the formula (Va)

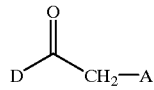

(V)

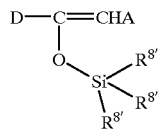

(Va)

in which

A, D and $R^8$ are each as defined above, required as starting materials for process (D) according to the invention are compounds which are commercially available, generally known or accessible by known processes.

The malonic acid esters of the formula (XXXII)

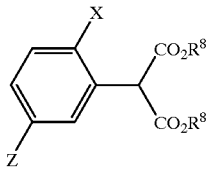

(XXXII)

in which $R^8$, X and Z are each as defined above, and Z is not hydrogen, are novel.

They can be prepared by generally known methods of organic chemistry (cf., for example, Tetrahedron Lett. 27, 2763 (1986) and Organikum VEB Deutscher Verlag der Wissenschaften, Berlin 1977, p. 587 ff).

The acid halides of the formula (VII), carboxylic anhydrides of the formula (VIII), chloroformic acid esters or chloroformic acid thioesters of the formula (IX), chloromonothioformic acid esters or chlorodithioformic acid esters of the formula (X), sulphonyl chlorides of the formula (XII), phosphorus compounds of the formula (XIII) and metal hydroxides, metal alkoxides or amines of the formula (XIV) and (XV) and isocyanates of the formula (XVI) and carbamoyl chlorides of the formula (XVII) additionally required as starting materials for carrying out processes (F), (G), (H), (I), (J) and (K) according to the invention are generally known compounds of organic or inorganic chemistry.

The compounds of the formulae (V), (VII) to (XVII), (XVIII), (XXI), (XXII), (XXIX), (XXX) and (XXXI) are moreover disclosed in the patent applications cited at the outset and/or can be prepared by the methods given there.

Process (A) is characterized in that compounds of the formula (II) in which A, B, X, Z and $R^8$ are each as defined above are subjected to an intramolecular condensation in the presence of a diluent and in the presence of a base.

Suitable diluents for the process (A) according to the invention are all organic solvents which are inert to the reaction participants. Those preferably utilizable are hydrocarbons, such as toluene and xylene, furthermore ethers, such as dibutyl ether, tetrahydrofuran, dioxane, glycol dimethyl ether and diglycol dimethyl ether, additionally polar solvents, such as dimethyl sulphoxide, sulpholane, dimethyl-formamide and n-methyl-pyrrolidone, and also alcohols such as methanol, ethanol, propanol, iso-propanol, butanol, iso-butanol and tert-butanol.

Suitable bases (deprotonating agents) for carrying out process (A) according to the invention are all customary proton acceptors. Those preferably utilizable are alkali metal and alkaline earth metal oxides, hydroxides and carbonates, such as sodium hydroxide, potassium hydroxide, magnesium oxide, calcium oxide, sodium carbonate, potassium carbonate and calcium carbonate, each of which can also be employed in the presence of a phase-transfer catalyst, for example triethylbenzylammonium chloride, tetrabutylammonium bromide, Adogene 464 (=methyltrialkyl($C_8$–$C_{10}$) ammonium chloride) or TDA 1 (=tris-(methoxyethoxyethyl)-amine. Alkali metals such as sodium or potassium can also be used. Furthermore, alkali metal and alkaline earth metal amides and hydrides, such as sodium amide, sodium hydride and calcium hydride, and additionally also alkali metal alkoxides, such as sodium methoxide, sodium ethoxide and potassium tert-butoxide can be employed.

When carrying out process (A) according to the invention, the reaction temperature can be varied within a relatively wide range. In general, the reaction is carried out at temperatures between 0° C. and 250° C., preferably between 50° C. and 150° C.

Process (A) according to the invention is generally carried out under atmospheric pressure.

When carrying out process (A) according to the invention, the reaction component of the formula (II) and the deprotonating base are generally employed in equimolar to approximately double equimolar amounts. However, it is also possible to use one component or the other in a relatively large excess (up to 3 mol).

Process (B) is characterized in that compounds of the formula (III) in which A, B, X, Z and $R^8$ are each as defined above are condensed intramolecularly in the presence of a diluent and in the presence of a base.

Suitable diluents for the process (B) according to the invention are all organic solvents which are inert to the reaction participants. Those preferably utilizable are hydrocarbons, such as toluene and xylene, furthermore ethers, such as dibutyl ether, tetrahydrofuran, dioxane, glycol dimethyl ether and diglycol dimethyl ether, and additionally polar solvents, such as dimethyl sulphoxide, sulpholane, dimethylformamide and N-methyl-pyrrolidone. Alcohols such as methanol, ethanol, propanol, iso-propanol, butanol, iso-butanol and tert-butanol can also be used.

Suitable bases (deprotonating agents) for carrying out the process (B) according to the invention are all customary proton acceptors. Those preferably utilizable are alkali metal and alkaline earth metal oxides, hydroxides and carbonates, such as sodium hydroxide, potassium hydroxide, magnesium oxide, calcium oxide, sodium carbonate, potassium carbonate and calcium carbonate, each of which can also be employed in the presence of phase-transfer catalysts, for example triethylbenzylammonium chloride, tetrabutylammonium bromide, Adogene 464 (=methyltrialkyl($C_8$–$C_{10}$-ammonium chloride) or TDA 1 (=tris-(methoxyethoxyethyl)-amine). Alkali metals such as sodium or potassium can also be used. Suitable are also alkali metal and alkaline earth metal amides and hydrides, such as sodium amide, sodium hydride and calcium hydride, and also alkali metal alkoxides, such as sodium methoxide, sodium ethoxide and potassium tert-butoxide.

When carrying out process (B) according to the invention, the reaction temperature can be varied within a relatively wide range. In general, the reaction is carried out at temperatures between 0° C. and 250° C., preferably between 50° C. and 150° C.

Process (B) according to the invention is generally carried out under atmospheric pressure.

When carrying out the process (B) according to the invention, the reaction components of the formula (III) and the deprotonating bases are generally employed in approximately equimolar amounts. However, it is also possible to use one component or the other in a relatively large excess (up to 3 mol).

Process (C) is characterized in that compounds of the formula (IV) in which A, B, W, X, Z and $R^8$ are each as defined above are cyclized intramolecularly in the presence of an acid and, if appropriate, in the presence of a diluent.

Suitable diluents for the process (C) according to the invention are all organic solvents which are inert to the reaction participants. Those preferably utilizable are hydrocarbons, such as toluene and xylene, furthermore halogenated hydrocarbons, such as dichloromethane, chloroform, ethylene chloride, chlorobenzene, dichlorobenzene, and additionally polar solvents, such as dimethyl sulphoxide, sulpholane, dimethylformamide and N-methyl-pyrrolidone. Alcohols such as methanol, ethanol, propanol, iso-propanol, butanol, iso-butanol and tert-butanol can also be used.

The acid employed can, if appropriate, also be used as a diluent.

Acids which can be employed in process (C) according to the invention are all customary inorganic and organic acids, for example hydrohalic acids, sulphuric acid, alkyl-, aryl- and haloalkyl sulphonic acids; halogenated alkylcarboxylic acids, for example trifluoroacetic acid, are used in particular.

When carrying out process (C) according to the invention, the reaction temperature can be varied within a relatively wide range. In general, the reaction is carried out at temperatures between 0° C. and 250° C., preferably between 50° C. and 150° C.

Process (C) according to the invention is generally carried out under atmospheric pressure.

When carrying out process (C) according to the invention, the reaction components of the formulae (IV) and the acid are employed, for example, in equimolar amounts. However, it is, if appropriate, also possible to employ the acid in catalytic amounts.

Process (D) according to the invention is characterized in that carbonyl compounds of the formula (V) or their silyl enol ethers of the formula (Va) are reacted with ketene acid halides of the formula (VI), if appropriate in the presence of a diluent and if appropriate in the presence of an acid acceptor.

Suitable diluents for the process (D) according to the invention are all organic solvents which are inert to the reaction participants. Those preferably utilizable are hydrocarbons, such as o-dichlorobenzene, tetraline, toluene and xylene, furthermore ethers, such as dibutyl ether, glycol dimethyl ether and diglycol dimethyl ether, and additionally polar solvents, such as dimethyl sulphoxide, sulpholane, dimethylformamide or N-methyl-pyrrolidone.

Acid acceptors which can be used when carrying out process (D) according to the invention are all customary acid acceptors.

Those preferably utilizable are tertiary amines, such as triethylamine, pyridine, diazabicyclooctane (DABCO), diazabicycloundecene (DBU), diazabicyclononene (DBN), Hünig base or N,N-dimethyl-aniline.

When carrying out process (D) according to the invention, the reaction temperature can be varied within a relatively wide range. The reaction is expediently carried out at temperatures between 0° C. and 250° C., preferably between 50° C. and 220° C.

Process (D) according to the invention is preferably carried out under atmospheric pressure.

When carrying out process (D) according to the invention, the reaction components of the formulae (V) and (VI) and, if appropriate, the acid acceptor are in general employed in approximately equimolar amounts. However, it is also possbile to use one component or the other in a relatively large excess (up to 5 mol).

Process (Eα) is characterized in that compounds of the formulae (I-1-a) to (I-4-a) are in each case reacted with carboxylic acid halides of the formula (VII), if appropriate in the presence of a diluent and if appropriate in the presence of an acid-binding agent.

Suitable diluents for the process (Eα) according to the invention are all solvents inert to the acid halides. Those preferably utilizable are hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, and also ketones, such as acetone and methyl isopropyl ketone, furthermore ethers, such as diethyl ether, tetrahydrofuran and dioxan, moreover carboxylic acid esters, such as ethyl acetate, and also strongly polar solvents, such as dimethylformamide, dimethylsulphoxide and sulpholane. If the stability to hydrolysis of the acid halide permits, the reaction can also be carried out in the presence of water.

Suitable acid-binding agents in the reaction of process (Eα) according to the invention are all customary acid acceptors. Those preferably utilizable are tertiary amines, such as triethylamine, pyridine, diazabicyclooctane (DABCO), diazabicycloundecene (DBU), diazabicyclononene (DBN), Hünig base and N,N-dimethyl-aniline, furthermore alkaline earth metal oxides, such as magnesium oxide and calcium oxide, and also alkali metal and alkaline earth metal carbonates, such as sodium carbonate, potassium carbonate and calcium carbonate and also alkali metal hydroxides such as sodium hydroxide and potassium hydroxide.

The reaction temperature in the process (Eα) according to the invention can be varied within a relatively wide range. In general, the reaction is carried out at temperatures between −20° C. and +150° C., preferably between 0° C. and 100° C.

When carrying out process (Eα) according to the invention, the starting materials of the formulae (I-1-a) to (I-4-a) and the carboxylic acid halide of the formula (VII) are in general each used in approximately equivalent amounts. However, it is also possible to employ the carboxylic acid halide in a relatively large excess (up to 5 mol). Work-up is carried out according to customary methods.

Process (Eβ) is characterized in that compounds of the formulae (I-1-a) to (I-4-a) are each reacted with carboxylic anhydrides of the formula (VIII), if appropriate in the presence of a diluent and if appopriate in the presence of an acid-binding agent.

Preferred diluents for the process (Eβ) according to the invention are those diluents which are also preferred when using acid halides. Otherwise, a carboxylic anhydride employed in excess may also simultaneously function as diluent.

Possible acid-binding agents added in process (Eβ) are preferably those acid-binding agents that are also preferred when using acid-halides.

The reaction temperature in the process (Eβ) according to the invention can be varied within a relatively wide range. In general, the reaction is carried out at temperatures between −20° C. and +150° C., preferably between 0° C. and 100° C.

When carrying out process (Eβ) according to the invention, the starting materials of the formulae (I-1-a) to (I-4-a) and the carboxylic anhydride of the formula (VIII) are in general each used in approximately equivalent amounts. However, it is also possible to employ the carboxylic anhydride in a relatively large excess (up to 5 mol). Work-up is carried out according to customary methods.

In general, a procedure is used in which diluent and excess carboxylic anhydride and the resulting carboxylic acid are removed by distillation or by washing with an organic solvent or with water.

Process (F) is characterized in that compounds of the formulae (I-1-a) to (I-4-a) are in each case reacted with chloroformic acid esters or chloroformic acid thioesters of the formula (IX), if appropriate in the presence of a diluent and if appropriate in the presence of an acid-binding agent.

Suitable acid-binding agents for process (F) according to the invention are all customary acid acceptors. Those preferably utilizable are tertiary amines, such as triethylamine, pyridine, DABCO, DBU, DBA, Hünig base and N,N-dimethylaniline, furthermore alkaline earth metal oxides, such as magnesium oxide and calcium oxide, additionally alkali metal and alkaline earth metal carbonates, such as sodium carbonate, potassium carbonate and calcium carbonate and also alkali metal hydroxides such as sodium hydroxide and potassium hydroxide.

Suitable diluents for the process (F) according to the invention are all solvents which are inert to the chloroformic acid esters or chloroformic acid thioesters. Those preferably utilizable are hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, additionally ketones, such as acetone and methyl isopropyl ketone, furthermore ethers, such as diethyl ether, tetrahydrofuran and dioxan, moreover carboxylic acid esters, such as ethyl acetate, furthermore nitriles, such as acetonitrile, and also strongly polar solvents, such as dimethylformamide, dimethyl sulphoxide and sulpholane.

When carrying out process (F) according to the invention, the reaction temperature can be varied within a relatively wide range. The reaction temperature is generally between −20° C. and +100° C., preferably between 0° C. and 50° C.

Process (F) according to the invention is in general carried out under atmospheric pressure.

When carrying out process (F) according to the invention, the starting materials of the formulae (I-1-a) to (I-4-a) and the appropriate chloroformic acid ester or chloroformic acid thioester of the formula (IX) are in general each used in approximately equivalent amounts. However, it is also possible to employ one component or the other in a relatively large excess (up to 2 mol). Work-up is carried out according to customary methods. In general, a procedure is used in which precipitated salts are removed and the reaction mixture which remains is concentrated by stripping off the diluent.

Process (G) according to the invention is characterized in that compounds of the formula (I-1-a) to (I-4-a) are in each case reacted with compounds of the formula (X) in the presence of a diluent and, if appropriate, in the presence of an acid-binding agent.

In preparation process (G), about 1 mol of chloromonothioformic acid ester or chlorodithioformic acid ester of the formula (X) is reacted per mol of a starting material of the formulae (I-1-a) to (I-4-a), at 0 to 120° C., preferably at 20 to 60° C.

Diluents which may be added, if appropriate, are all inert polar organic solvents, such as ethers, amides, sulphones, sulphoxides, and also halogenoalkanes.

Dimethyl sulphoxide, tetrahydrofuran, dimethylformamide or methylene chloride are preferably employed.

If, in a preferred embodiment, the enolate salt of the compounds (I-1-a) to (I-4-a) is prepared by addition of strong deprotonating agents, for example sodium hydride or potassium tert-butoxide, the further addition of acid-binding agents can be dispensed with.

If acid-binding agents are used, customary inorganic or organic bases are suitable; sodium hydroxide, sodium carbonate, potassium carbonate, pyridine and triethylamine may be mentioned by way of example.

The reaction can be carried out at atmospheric pressure or at elevated pressure; it is preferably carried out at atmospheric pressure. Work-up takes place according to customary methods.

Process (H) according to the invention is characterized in that compounds of the formulae (I-1-a) to (I-4-a) are in each case reacted with sulphonyl chlorides of the formula (XII), if appropriate in the presence of a diluent and if appropriate in the presence of an acid-binding agent.

In preparation process (H), about 1 mol of sulphonyl chloride of the formula (XII) is reacted per mol of starting material of the formulae (I-1-a) to (I-4-a) at −20 to 150° C., preferably at 0 to 70° C.

Process (H) is preferably carried out in the presence of a diluent.

Suitable diluents are all inert polar organic solvents, such as ethers, amides, ketones, carboxylic acid esters, nitriles, sulphones, sulphoxides or halogenated hydrocarbons such as methylene chloride.

Dimethyl sulphoxide, tetrahydrofuran, dimethylformamide and methylene chloride are preferably employed.

If, in a preferred embodiment, the enolate salt of the compounds (I-1-a) to (I-4-a) is prepared by addition of strong deprotonating agents (for example sodium hydride or potassium tert-butoxide), the further addition of acid-binding agents can be dispensed with.

If acid-binding agents are employed, customary inorganic or organic bases are suitable; sodium hydroxide, sodium carbonate, potassium carbonate, pyridine and triethylamine may be mentioned by way of example.

The reaction can be carried out at atmospheric pressure or at elevated pressure; it is preferably carried out at atmospheric pressure. Work-up takes place according to customary methods.

The process (I) according to the invention is characterized in that compounds of the formulae (I-1-a) to (I-4-a) are in each case reacted with phosphorus compounds of the formula (XIII), if appropriate in the presence of a diluent and if appropriate in the presence of an acid-binding agent.

In preparation process (I), 1 to 2, preferably 1 to 1.3, mol of the phosphorus compound of the formula (XIII) is reacted per 1 mol of the compounds (I-1-a) to (I-4-a) at temperatures between −40° C. and 150° C., preferably between −10° C. and 110° C., to give compounds of the formulae (I-1-e) to (I-4-e).

The process (I) is preferably carried out in the presence of a diluent.

Suitable diluents are all inert polar organic solvents, such as ethers, carboxylic acid esters, halogenated hydrocarbons, ketones, amides, nitriles, sulphones, sulphoxides, etc.

Acetonitrile, dimethyl sulphoxide, tetrahydrofuran, dimethylformamide or methylene chloride are preferably employed.

Acid-binding agents which may be added, if appropriate, are customary inorganic or organic bases, such as hydroxides, carbonates or amines. By way of example, sodium hydroxide, sodium carbonate, potassium carbonate, pyridine and triethylamine may be mentioned.

The reaction may be carried out at atmospheric pressure or at elevated pressure; it is preferably carried out at atmospheric pressure. Work-up takes place according to conventional methods of organic chemistry. The end products are preferably purified by crystallization, chromatographic purification or by so-called "incipient distillation", i.e. removal of the volatile constituents in vacuo.

Process (J) is characterized in that compounds of the formulae (I-1-a) to (I-4-a) are in each case reacted with metal hydroxides or metal alkoxides of the formula (XIV) or amines of the formula (XV), if appropriate in the presence of a diluent.

Preferred diluents for process (J) according to the invention are ethers such as tetrahydrofuran, dioxan and diethyl ether or else alcohols such as methanol, ethanol and isopropanol, but also water. Process (J) according to the invention is generally carried out under atmospheric pressure. The reaction temperature is in general between −20° C. and 100° C., preferably between 0° C. and 50° C.

Process (K) according to the invention is characterized in that compounds of the formulae (I-1-a) to (I-4-a) are in each case reacted with (Kα) compounds of the formula (XVI), if appropriate in the presence of a diluent and if appropriate in the presence of a catalyst, or (Kβ) with compounds of the formula (XVII), if appropriate in the presence of a diluent and if appropriate in the presence of an acid-binding agent.

In preparation process (Kα), about 1 mol of isocyanate of the formula (XVI) is reacted per mole of starting material of the formulae (I-1-a) to (I-4-a) at 0 to 100° C., preferably at 20 to 50° C.

Process (Kα) is preferably carried out in the presence of a diluent.

Suitable diluents are all inert organic solvents, such as aromatic hydrocarbons, halogenated hydrocarbons, ethers, amides, nitrites, sulphones or sulphoxides.

Catalysts may, if desired, be added to accelerate the reaction. The catalysts employed can very advantageously be organotin compounds, for example dibutyltin dilaurate.

The reaction is preferably carried out at atmospheric pressure.

In preparation process (Kβ), about 1 mol of carbamoyl chloride of the formula (XVII) is reacted at 0 to 150° C., preferably at 20 to 70° C., per mole of starting material of the formulae (I-1-a) to (I-4-a).

Possible diluents optionally added are all inert polar organic solvents, such as ethers, carboxylic acid esters, nitriles, ketones, amides, sulphones, sulphoxides or halogenated hydrocarbons.

Dimethyl sulphoxide, tetrahydrofuran, dimethylformamide or methylene chloride are preferably employed.

If, in a preferred embodiment, the enolate salt of the compound (I-1-a) to (I-4-a) is prepared by addition of strong deprotonating agents (e.g. sodium hydride or potassium tertiary butoxide), the further addition of acid-binding agents can be dispensed with.

If acid-binding agents are employed, customary inorganic or organic bases are suitable; those which may be mentioned by way of example are sodium hydroxide, sodium carbonate, potassium carbonate, triethylamine or pyridine.

The reaction can be carried out at atmospheric pressure or at elevated pressure, preferably at atmospheric pressure. Work-up takes place according to customary methods.

The active compounds are suitable for controlling animal pests, preferably arthropods and nematodes, in particular insects and arachnida, which are encountered in agriculture, in forestry, in the protection of stored products and of materials, and in the hygiene field. They are active against normally sensitive and resistant species and against all or some stages of development. The abovementioned pests include:

From the order of Isopoda, for example, *Oniscus asellus, Armadillidium vulgare* and *Porceillio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for exanple, *Lepisma saccharina.*

From the order of the Collembola, for example, *Onychiurus armatus.*

From the order of the Orthoptera, for example, *Blatta orientalis, Periplaneta americana, Leucophaea maderae, Blatella germanica, Acheta domesticus, Gryllotalpa spp., Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Phylloxera vastatrix,* Pemphigus spp., *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp, *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehnielia, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., Melolontha melolontha, Amphimallon solstitialis and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The active compounds according to the invention are distinguished by a high insecticidal and acaricidal activity.

They can be used to particularly good effect for controlling insects which are injurious to plants, such as, for example, against the larvae of the mustard beetle (*Phaedon cochleariae*), against the larvae of the green rice leaf hopper (*Nephotettix cincticeps*) or against the caterpillars of the cabbage moth (*Plutella maculipennis*) (cf. the Use Examples).

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes of methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkylsulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compound according to the invention can be present in its commercially available formulations and in the use forms prepared from these formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms.

Examples of particularly advantageous mixture components are the following compounds:

Fungicides 2-aminobutane; 2-anilino-4-methyl-6-cyclopropyl-pyrimidine; 2',6'-dibromo-2-methyl-4'- trifluoromethoxy-4'-trifluoro-methyl-1,3-thiazole-5-carboxanilide; 2,6-dichloro-N-(4-trifluoromethylbenzyl)-benzamide; (E)-2-methoxyimino-N-methyl-2-(2-phenoxyphenyl)-acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino-[alpha-(o-tolyloxy)-o-tolyl]-acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulphamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulphocarb, methfuroxam, metiram, metsulphovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebucanozole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram.

Bactericides bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides abamectin, AC 303 630, acephate, acrinathrin, alanycarb, aldicarb, alphamethrin, amitraz, avermectin, AZ 60541, azadirachtin, azinphos A, azinphos M, azocyclotin. *Bacillus thuringiensis*, bendiocarb, benfuracarb, bensultap, beta-cyfluthrin, bifenthrin, BPMC, brofenprox, bromophos A, bufencarb, buprofezin, butocarboxim, butylpyridaben, cadusafos, carbaryl, carbofuran, carbophenothion, carbosulphan, cartap, CGA 157 419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton-M, demeton-S, demeton-S-methyl, diafenthiuron, diazinon, dichlofenthion, dichlorvos, dicliphos, dicrotophos, diethion, diflubenzuron, dimethoate, dimethylvinphos, dioxathion, disulphoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivemectin, lambda-cyhalothrin, lufenuron, malathion, mecarbam, mevinphos, mesulphenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen, quinalphos, RH 5992, salithion, sebufos, silafluofen, sulphotep, sulprofos, tebufenozid, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, YI 5301/5302, zetamethrin.

Herbicides for example anilides such as, for example, diflufenican and propanil; arylcarboxylic acids such as, for example, dichloropicolinic acid, dicamba and picloram; aryloxyalkanoic acids such as, for example, 2,4-D, 2,4-DB, 2,4-DP, fluroxypyr, MCPA, MCPP and triclopyr; aryloxy-phenoxyalkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenz-thiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amidosulphuron, bensulphuron-methyl, chlorimuron-ethyl, chlorsulphuron, cinosulphuron, metsulphuron-methyl, nicosulphuron, primisulphuron, pyrazosulphuron-ethyl, thifensulphuron-methyl, triasulphuron and tribenuronmethyl; thiocarbamates such as, for example, butylate, cycloate, di-allate, EPTC, esprocarb, molinate, prosulphocarb, thiobencarb and tri-allate; triazines such as, for example, atrazine, cyanazine, simazine, simetryne, terbutryne and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane The active compound according to the invention can furthermore be present in its commercially available formulations and in the use forms prepared from these formulations, as a mixture with synergistic agents. Synergistic agents are compounds which increase the action of the active compounds without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds according to the invention are not only active against plant, hygiene and stored-product pests, but also, in the veterinary medicine sector, against animal parasites (ectoparasites), such as ixodid ticks, argasid ticks, scab mites, trombiculid mites, flies (stinging and sucking), parasitic fly larvae, lice, hair lice, bird lice and fleas. These parasites include:

From the order of the Anoplurida, for example, Haematopinus spp., Linognathus spp., Pediculus spp., Phtirus spp., Solenopotes spp.

From the order of the Mallophagida and the sub-orders Amblycerina and Ischnocerina, for example, Trimenopon spp., Menopon spp., Trinoton spp., Bovicola spp., Werneckiella spp., Lepikentron spp., Damalina spp., Trichodectes spp., Felicola spp.

From the order Diptera and the sub-orders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp. and Melophagus spp., From the order of the Siphonapterida, for example, Pulex spp., Ctenocephalides spp., Xenopsylla spp. and Ceratophyllus spp.

From the order of the Heteropterida, for example, Cimex spp., Triatoma spp., Rhodnius spp. and Panstrongylus spp.

From the order of the Blattarida, for example, *Blatta orientalis, Periplaneta americana, Blattela germanica* and Supella spp.

From the sub-class of the Acaria (Acarida) and the orders of the Meta- and Mesostigmata, for example Argas spp., Ornithodorus spp., Otabius spp., Ixodes spp., Amblyomma spp., Boophilus spp., Dermacentor spp., Haemaphysalis spp., Hyalomma spp., Rhipicephalus spp., Dermanyssus spp., Raillietia spp., Pneumonyssus spp., Sternostoma spp. and Varroa spp.

From the order of the Actinedida (Prostigmata) and Acaridida (Astigmata), for example Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Octodectes spp., Sarcoptes spp., Notoedres spp., Knemidocoptes spp., Cytodites spp. and Laminosioptes spp.

For example, they show an outstanding activity against *Boophilus microplus* and *Lucilia cuprina*.

The active compounds of the formula (I) according to the invention are also suitable for controlling arthropods which attack agricultural livestock, such as, for example, cattle, sheep, goats, horses, pigs, donkeys, camels, buffalo, rabbits, chickens, turkeys, ducks, geese, honey bees, other domestic animals, such as, for example, dogs, cats, cage birds, aquarium fish, and so-called experimental animals such as, for example, hamsters, guinea-pigs, rats and mice. By controlling these arthropods, it is intended to reduce mortality and decreased performance (in meat, milk, wool, hides, eggs, honey and the like), so that more economical and simpler animal keeping is made possible by using the active compounds according to the invention.

In the veterinary sector, the active compounds according to the invention are used in a known manner by enteral administration, for example in the form of tablets, capsules, drinks, drenches, granules, pastes, boluscs, the feed-through method, suppositories, by parenteral administration, such as, for example, by means of injections (intramuscular, subcutaneous, intravenous, intraperitoneal and the like), implants, by nasal application, by dermal administration, for example in the form of dipping or bathing, spraying, pouring-on and spotting-on, washing, dusting, and with the aid of shaped articles which comprise active compound, such as collars, ear tags, tail marks, limb bands, halters, marking devices and the like.

When administered to livestock, poultry, domestic animals and the like, the active compounds of the formula (I) can be used as formulations (for example powders, emulsions, flowables) which comprise the active compounds in an amount of 1 to 80% by weight, either directly or after dilution by a factor of 100 to 10,000, or they may be used in the form of a chemical bath.

Furthermore, it has been found that the compounds of the formula (I) according to the invention have a potent insecticidal action against insects which destroy industrial materials.

The following insects may be mentioned by way of example and as being preferred, but without any limitation:

Beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis,* Zyleborus spec., Tryptodendron spec., *Apate monachus, Bostrychus capucins, Heterobostrychus brunneus,* Sinoxylon spec., *Dinoderus minutus.*

Dermapterans, such as *Sirex juvencus, Urocerus gigas, Urocerus gigas taignus, Urocerus augur.*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristletails, such as *Lepisma saccharina.*

Industrial materials are to be understood as meaning, in the present context, non-live materials such as, preferably, synthetic materials, glues, sizes, paper and board, leather, wood and timber products, and paint.

The materials to be very particularly protected against attack by insects are wood and timber products.

Wood and timber products which can be protected by the composition according to the invention or mixtures comprising such a composition are to be understood as meaning, for example, construction timber, wooden beams, railway sleepers, bridge components, jetties, wooden vehicles, boxes, pallets, containers, telephone poles, wood lagging, windows and doors made of wood, plywood, particle board, joiner's articles, or wood products which, quite generally, are used in the construction of houses or in joinery.

The active compounds can be used as such, in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if appropriate desiccants and UV stabilizers and, if appropriate, colorants and pigments and other processing auxiliaries.

The insecticidal compositions or concentrates used for the protection of wood and wooden materials comprise the active compound according to the invention at a concentration of 0.0001 to 95% by weight, in particular 0.001 to 60% by weight.

The amount of the compositions or concentrates employed depends on the species and the occurrence of the insects and on the medium. The optimum rate of application can be determined upon use in each case by test series. However, in general, it suffices to employ 0.0001 to 20% by weight, preferably 0.001 to 10% by weight, of the active compound, based on the material to be protected.

The solvent and/or diluent used is an organochemical solvent or solvent mixture and/or an oily or oil-type organochemical solvent or solvent mixture of low volatility and/or a polar organochemical solvent or solvent mixture and/or water and, if appropriate, an emulsifier and/or wetting agent.

Organochemical solvents which are preferably employed are oily or oil-type solvents having an evaporation number of above 35 and a flashpoint of above 30° C., preferably above 45° C. Substances which are used as such oily and oil-type solvents which have low volatility and are insoluble in water are suitable mineral oils or their aromatic fractions, or mineral-oil-containing solvent mixtures, preferably white spirit, petroleum and/or alkylbenzene.

Substances which are advantageously used are mineral oils with a boiling range of 170 to 220° C., white spirit with a boiling range of 170 to 220° C., spindle oil with a boiling range of 250 to 350° C., petroleum or aromatics of boiling range 160 to 280° C., essence of turpentine and the like.

In a preferred embodiment, liquid aliphatic hydrocarbons with a boiling range of 180 to 210° C. or high-boiling mixtures of aromatic and aliphatic hydrocarbons ith a boiling range of 180 to 220° C. and/or spindle oil and/or monochloronaphthalene, preferably α-monochloronaphthalene, are used.

The organic oily or oil-type solvents of low volatility having an evaporation number of above 35 and a flashpoint of above 30° C., preferably above 45° C., can be partially replaced by organochemical solvents of high or medium volatility, with the proviso that the solvent mixture also has an evaporation number of above 35 and a flashpoint of above 30° C., preferably above 45° C., and that the insecticide/fungicide mixture is soluble or emulsifiable in this solvent mixture.

In a preferred embodiment, part of the organochemical solvent or solvent mixture is replaced by an aliphatic polar organochemical solvent or solvent mixture. Substances which are preferably used are aliphatic organochemical solvents having hydroxyl and/or ester and/or ether groups, such as, for example, glycol ether, esters and the like.

The organochemical binders used within the scope of the present invention are the synthetic resins and/or binding drying oils which are known per se and can be diluted with water and/or are soluble or dispersible or emulsifiable in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indene/coumarone resin, silicone resin, drying vegetable and/or drying oils and/or physically drying binders based on a natural and/or synthetic resin.

The synthetic resin used as the binder can be employed in the form of an emulsion, dispersion or solution. Up to 10% by weight of bitumen or bituminous substances can also be used as binders. In addition, colorants, pigments, water repellents, odour-masking substances and inhibitors or anti-corrosives known per se and the like can also be employed.

The composition or the concentrate preferably comprises, in accordance with the invention, at least one alkyd resin or modified alkyd resin and/or a drying vegetable oil as the organochemical binder. Preferably used according to the invention are alkyd resins with an oil content of over 45% by weight, preferably 50 to 68% by weight.

All or some of the abovementioned binder can be replaced by a fixative (mixture) or a plasticizer (mixture). These additives are intended to prevent volatilization of the active compounds and crystallization or precipitation. They preferably replace 0.01 to 30% of the binder (based on 100% of binder employed).

The plasticizers are from the chemical classes of the phthalic esters, such as dibutyl phthalate, dioctyl phthalate or benzylbutyl phthalate, the phosphoric esters, such as tributyl phosphate, the adipic esters, such as di-(2-ethylhexyl) adipate, the stearates, such as butyl stearate or amyl stearate, the oleates, such as butyl oleate, the glycerol ethers or relatively high-molecular-weight glycol ethers, glycerol esters and p-toluene-sulphonic esters.

Fixatives are chemically based on polyvinyl alkyl ethers, such as, for example, polyvinyl methyl ether, or ketones, such as benzophenone or ethylene benzophenone.

Particularly suitable as a solvent or diluent is also water, if appropriate as a mixture with one or more of the abovementioned organochemical solvents or diluents, emulsifiers and dispersants.

Particularly effective protection of wood is achieved by large-scale industrial impregnation processes, for example vacuum, double-vacuum or pressure processes.

If appropriate, the ready-to-use compositions can additionally comprise one or more other insecticides and, if appropriate, additionally one or more fungicides.

Suitable additional components which may be admixed are, preferably, the insecticides and fungicides mentioned in WO 94/29 268. The compounds mentioned in that document are expressly part of the present application.

Very particularly preferred components which may be admixed are insecticides, such as chlorpyriphos, phoxim, silafluofin, alphamethrin, cyfluthrin, cypermethrin, deltamethrin, permethrin, imidacloprid, NI-25, flufenoxuron, hexaflumuron and triflumuron, and fungicides, such as epoxyconazole, hexaconazole, azaconazole, propiconazole, tebuconazole, cyproconazole, metconazole, imazalil, dichloro-fluanide, tolylfluanide, 3-iodo-2-propinylbutyl carbamate, N-octyl-isothiazolin-3-one and 4,5-dichloro-N-octylisothiazolin-3-one.

The preparation and the use of the active compounds according to the invention can be seen from the examples below.

PREPARATION EXAMPLES

Example (I-1-a-1)

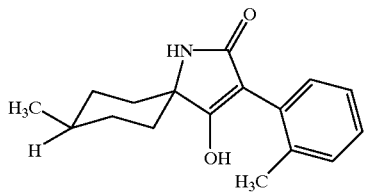

At 80° C., 17.9 g of the compound of Example II-1 in 36 ml of anhydrous dimethylformamide (DMF) are added dropwise to 14.94 g (0.128 mol) of potassium tert-butoxide in 51 ml of anhydrous DMF, and the mixture is stirred at room temperature for 1.5 hours. 440 ml of ice-water are then added and the mixture is acidified to pH 1 at 0–20° C. using concentrated HCl and the precipitate is filtered off with suction and dried. The crude product is stirred with methyl tert-butyl ether (MTBE)/n-hexane, filtered off with suction and dried.

Yield: 10 g (62% of theory); mp.: >220° C.

Similar to Example (I-1-a-1) and/or according to the general preparation instructions, the following compounds of the formula (I-1-a) are obtained:

Example (I-1-b-1)

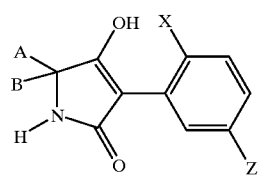

2.3 g (8 mmol) of the compound of Example I-1-a-2 are precharged in 50 ml of anhydrous ethyl acetate and admixed with 1.34 ml (9.6 mmol) of triethylamine, and 1.01 ml (9.6 mmol) of isobutyryl chloride in 5 ml of anhydrous ethyl acetate are added dropwise under reflux. After 16 hours at reflux, the mixture is concentrated and the residue is taken up in methylene chloride, washed 2× with 50 ml of 0.5N NaOH each time, dried and evaporated. The residue is recrystallized from methyl tert-butyl ether (MTB ether)/n-hexane.

Yield: 1.8 g (Δ 62% of theory) mp.: 163° C.

Similar to Example (I-1-b-1) and/or according to the general preparation instructions, the following compounds of the formula (I-b-1) are obtained:

(I-1-a)

| Ex. No. | X | Z | A | B | Isomer | mp. ° C. |
|---|---|---|---|---|---|---|
| I-1-a-2 | CH$_3$ | H | —(CH$_2$)$_2$—CHOCH$_3$—(CH$_2$)$_2$— | | β | >220 |
| I-1-a-3 | CH$_3$ | CH$_3$ | —(CH$_2$)$_2$—CHCH$_3$—(CH$_2$)$_2$— | | β | >220 |
| I-1-a-4 | CH$_3$ | CH$_3$ | —(CH$_2$)$_2$—CHOCH$_3$—(CH$_2$)$_2$— | | β | >220 |
| I-1-a-5 | OCH$_3$ | H | —(CH$_2$)$_2$—CHCH$_3$—(CH$_2$)$_2$— | | β | 181 |
| I-1-a-6 | i-C$_3$H$_7$ | H | —(CH$_2$)$_2$—CHCH$_3$—(CH$_2$)$_2$— | | β | 193 |
| I-1-a-7 | Cl | NO$_2$ | —(CH$_2$)$_2$—CHCH$_3$—(CH$_2$)$_2$— | | β | >220 |
| I-1-a-8 | CH$_3$ | CH$_3$ | —(CH$_2$)$_2$—CHOC$_2$H$_5$—(CH$_2$)$_2$— | | β | 128 |
| I-1-a-9 | OCH$_2$—C$_6$H$_5$ | H | —(CH$_2$)$_2$—CHCH$_3$—(CH$_2$)$_2$— | | β | 188 |
| I-1-a-10 | CH$_3$ | CH$_3$ | i-C$_3$H$_7$ | CH$_3$ | — | 117 |
| I-1-a-11 | CH$_3$ | CH$_3$ | CH$_3$ | CH$_3$ | — | 210 |
| I-1-a-12 | Br | OCH$_3$ | —(CH$_2$)$_2$—CHCH$_3$—(CH$_2$)$_2$— | | β | >220 |
| I-1-a-13 | Cl | NH$_2$ | —(CH$_2$)$_2$—CHCH$_3$—(CH$_2$)$_2$— | | β | |
| I-1-a-14 | OCH$_3$ | Cl | —(CH$_2$)$_2$—CHOCH$_3$—(CH$_2$)$_2$— | | β | >220 |
| I-1-a-15 | Br | OCH$_3$ | —(CH$_2$)$_2$—CHOCH$_3$—(CH$_2$)$_2$— | | β | >220 |
| I-1-a-16 | Cl | CH$_3$ | —(CH$_2$)$_2$—CHOCH$_3$—(CH$_2$)$_2$— | | β | >220 |
| I-1-a-17 | F | OCH$_3$ | —(CH$_2$)$_2$—CHOCH$_3$—(CH$_2$)$_2$— | | β | >220 |
| I-1-a-18 | CH$_3$ | CH$_3$ | —(CH$_2$)$_2$—O—(CH$_2$)$_2$— | | — | 215 |
| I-1-a-19 | Cl | Cl | —(CH$_2$)$_2$—CHOCH$_3$—(CH$_2$)$_2$— | | β | 218 |
| I-1-a-20 | F | F | —(CH$_2$)$_2$—CHOCH$_3$—(CH$_2$)$_2$— | | β | >220 |
| I-1-a-21 | Br | Br | —(CH$_2$)$_2$—CHOCH$_3$—(CH$_2$)$_2$— | | β | >220 |
| I-1-a-22 | Cl | H | —(CH$_2$)$_2$—CHOCH$_3$—(CH$_2$)$_2$— | | β | 218 |
| I-1-a-23 | Cl | NO$_2$ | —(CH$_2$)$_2$—CHOCH$_3$—(CH$_2$)$_2$— | | β | >220 |
| I-1-a-24 | F | CH$_3$ | —(CH$_2$)$_2$—CHOCH$_3$—(CH$_2$)$_2$— | | β | 200–201 |

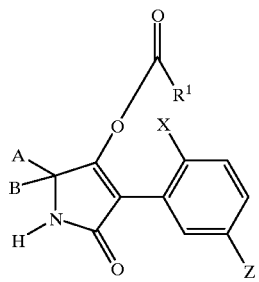

(I-1-b)

| Ex. No. | X | Z | A | B | R¹ | mp. °C. | Isomer |
|---|---|---|---|---|---|---|---|
| I-1-b-2 | i-$C_3H_7$ | H | —$(CH_2)_2$—$CHCH_3$—$(CH_2)_2$— | | i-$C_3H_7$— | 183 | β |
| I-1-b-3 | i-$C_3H_7$ | H | —$(CH_2)_2$—$CHCH_3$—$(CH_2)_2$— | | t-$C_4H_9$— | 198 | β |
| I-1-b-4 | $CH_3$ | $CH_3$ | —$(CH_2)_2$—$CHCH_3$—$(CH_2)_2$— | | i-$C_3H_7$— | 170 | β |
| I-1-b-5 | $CH_3$ | $CH_3$ | —$(CH_2)_2$—$CHCH_3$—$(CH_2)_2$— | | t-$C_4H_9$—$CH_2$— | 198 | β |
| I-1-b-6 | $CH_3$ | $CH_3$ | —$(CH_2)_2$—$CHCH_3$—$(CH_2)_2$— | | 4-Cl—$C_6H_4$— | 213 | β |
| I-1-b-7 | $CH_3$ | $CH_3$ | —$(CH_2)_2$—$CHOCH_3$—$(CH_2)_2$— | | i-$C_3H_7$— | 145 | β |
| I-1-b-8 | $CH_3$ | $CH_3$ | —$(CH_2)_2$—$CHOCH_3$—$(CH_2)_2$— | | t-$C_4H_9$—$CH_2$— | 194 | β |
| I-1-b-9 | $CH_3$ | $CH_3$ | $CH_3$ | $CH_3$ | i-$C_3H_7$— | 188 | — |
| I-1-b-10 | $CH_3$ | $CH_3$ | —$(CH_2)_2$—$CHOC_2H_5$—$(CH_2)_2$— | | i-$C_3H_7$— | 143 | β |
| I-1-b-11 | Br | $OCH_3$ | —$(CH_2)_2$—$CHCH_3$—$(CH_2)_2$— | | i-$C_3H_7$— | 151 | β |
| I-1-b-12 | Cl | $NO_2$ | —$(CH_2)_2$—$CHCH_3$—$(CH_2)_2$— | | i-$C_3H_7$— | >220 | β |
| I-1-b-13 | O—$CH_2$—$C_6H_5$ | H | —$(CH_2)_2$—$CHCH_3$—$(CH_2)_2$— | | i-$C_3H_7$— | 161 | β |
| I-1-b-14 | $CH_3$ | $CH_3$ | i-$C_3H_7$ | $CH_3$ | $C_2H_5$—O—$CH_2$— | 103 | — |
| I-1-b-15 | $CH_3$ | $CH_3$ | —$(CH_2)_2$—$CHOCH_3$—$(CH_2)_2$— | | i-$C_4H_9$— | 157 | β |
| I-1-b-16 | $CH_3$ | $CH_3$ | —$(CH_2)_2$—$CHOCH_3$—$(CH_2)_2$— | | cyclohexyl | 171 | β |
| I-1-b-17 | $CH_3$ | $CH_3$ | —$(CH_2)_2$—$CHOCH_3$—$(CH_2)_2$— | | $C_2H_5$O—$CH_2$— | 131 | β |
| I-1-b-18 | $CH_3$ | $CH_3$ | —$(CH_2)_2$—$CHOCH_3$—$(CH_2)_2$— | | 4-Cl—$C_6H_4$— | 164 | β |
| I-1-b-19 | $CH_3$ | $CH_3$ | —$(CH_2)_2$—$CHOCH_3$—$(CH_2)_2$— | | 2-thienyl | 164 | β |
| I-1-b-20 | $CH_3$ | $CH_3$ | —$(CH_2)_2$—$CHOCH_3$—$(CH_2)_2$— | | t-$C_4H_9$— | 129 | β |
| I-1-b-21 | $OCH_3$ | Cl | —$(CH_2)_2$—$CHOCH_3$—$(CH_2)_2$— | | i-$C_3H_7$— | 216–218 | β |
| I-1-b-22 | Br | $OCH_3$ | —$(CH_2)_2$—$CHOCH_3$—$(CH_2)_2$— | | i-$C_3H_7$— | 123–124 | β |
| I-1-b-23 | Cl | $CH_3$ | —$(CH_2)_2$—$CHOCH_3$—$(CH_2)_2$— | | i-$C_3H_7$— | | β |
| I-1-b-24 | Br | Br | —$(CH_2)_2$—$CHOCH_3$—$(CH_2)_2$— | | i-$C_3H_7$— | 199–200 | β |
| I-1-b-25 | $CH_3$ | $CH_3$ | —$(CH_2)_2$—$CHOC_2H_5$—$(CH_2)_2$— | | $CH_3$— | 187–188 | β |
| I-1-b-26 | $CH_3$ | $CH_3$ | —$(CH_2)_2$—$CHOC_2H_5$—$(CH_2)_2$— | | i-$C_4H_9$— | 110–111 | β |
| I-1-b-27 | $CH_3$ | $CH_3$ | —$(CH_2)_2$—$CHOC_2H_5$—$(CH_2)_2$— | | $C_2H_5$O—$CH_2$— | | β |
| I-1-b-28 | $CH_3$ | $CH_3$ | —$(CH_2)_2$—$CHOC_2H_5$—$(CH_2)_2$— | | cyclohexyl | 162–164 | β |
| I-1-b-29 | $CH_3$ | $CH_3$ | —$(CH_2)_2$—$CHOC_2H_5$—$(CH_2)_2$— | | 4-Cl—$C_6H_4$— | >225 | β |
| I-1-b-30 | $CH_3$ | $CH_3$ | —$(CH_2)_2$—$CHOC_2H_5$—$(CH_2)_2$— | | 2-thienyl | 181 | β |
| I-1-b-31 | $CH_3$ | $CH_3$ | —$(CH_2)_2$—$CHOC_2H_5$—$(CH_2)_2$— | | s-$C_4H_9$— | 103–104 | β |

Example I-1-c-1

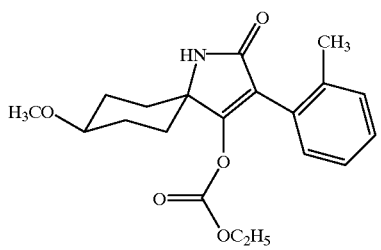

2.3 g (8 mmol) of the compound of Example I-1-a-2 are precharged in 50 ml of anhydrous methylene chloride and admixed with 1.12 ml (8 mmol) of triethylamine, and 0.8 ml (8 mmol) of ethyl chloroformate in 5 ml of anhydrous methylene chloride are added dropwise at 0–10° C. Stirring is continued at room temperature and the reaction is monitored by TLC. The mixture is then washed 2× with 50 ml of 0.5N NaOH each time, dried and evaporated, and the residue is recrystallized from MTB ether/n-hexane.

Yield: 1.7 g (Δ 59% of theory) mp.: 135° C.

Similar to Example (I-1-c-1) and/or according to the general preparation instructions, the following compounds of the formula (I-1-c) are obtained:

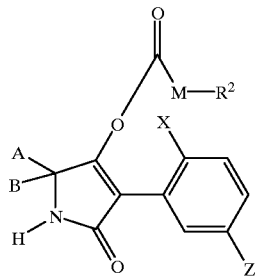

(I-1-c)

| Ex. No. | X | Z | A | B | M | R² | mp. °C. | Isomer |
|---|---|---|---|---|---|---|---|---|
| I-1-c-2 | i-C₃H₇ | H | —(CH₂)₂—CHCH₃—(CH₂)₂— | | O | C₂H₅ | 198 | β |
| I-1-c-3 | CH₃ | CH₃ | —(CH₂)₂—CHCH₃—(CH₂)₂— | | O | C₂H₅ | 146 | β |
| I-1-c-4 | CH₃ | CH₃ | —(CH₂)₂—CHOCH₃—(CH₂)₂— | | O | C₂H₅ | 128 | β |
| I-1-c-5 | CH₃ | CH₃ | CH₃ | CH₃ | O | C₂H₅ | 139 | — |
| I-1-c-6 | CH₃ | CH₃ | —(CH₂)₂—CHOC₂H₅—(CH₂)₂— | | O | C₂H₅ | 126 | β |
| I-1-c-7 | Br | OCH₃ | —(CH₂)₂—CHCH₃—(CH₂)₂— | | O | C₂H₅ | 175 | β |
| I-1-c-8 | Cl | NO₂ | —(CH₂)₂—CHCH₃—(CH₂)₂— | | O | C₂H₅ | 236 | β |
| I-1-c-9 | O—CH₂—C₆H₅ | H | —(CH₂)₂—CHCH₃—(CH₂)₂— | | O | C₂H₅ | 131 | β |
| I-1-c-10 | CH₃ | CH₃ | —(CH₂)₂—CHOCH₃—(CH₂)₂— | | O | i-C₄H₉— | 122 | β |
| I-1-c-11 | CH₃ | CH₃ | —(CH₂)₂—CHOCH₃—(CH₂)₂— | | O | C₆H₅—CH₂ | 139 | β |
| I-1-c-12 | CH₃ | CH₃ | —(CH₂)₂—CHOCH₃—(CH₂)₂— | | O | C₆H₅— | 193 | β |
| I-1-c-13 | OCH₃ | CH₃ | —(CH₂)₂—CHOCH₃—(CH₂)₂— | | O | C₂H₅— | 208–211 | β |
| I-1-c-14 | Br | OCH₃ | —(CH₂)₂—CHOCH₃—(CH₂)₂— | | O | C₂H₅— | 180–182 | β |
| I-1-c-15 | Cl | CH₃ | —(CH₂)₂—CHOCH₃—(CH₂)₂— | | O | C₂H₅— | 153–155 | β |
| I-1-c-16 | Br | Br | —(CH₂)₂—CHOCH₃—(CH₂)₂— | | O | C₂H₅— | >230 | β |
| I-1-c-17 | CH₃ | CH₃ | —(CH₂)₂—CHOC₂H₅—(CH₂)₂— | | O | i-C₄H₉— | 137–139 | β |
| I-1-c-18 | CH₃ | CH₃ | —(CH₂)₂—CHOC₂H₅—(CH₂)₂— | | O | C₆H₅—CH₂ | 135–137 | β |
| I-1-c-19 | CH₃ | CH₃ | —(CH₂)₂—CHOC₂H₅—(CH₂)₂— | | S | i-C₃H₇— | 152–154 | β |
| I-1-c-20 | CH₃ | CH₃ | —(CH₂)₂—CHOC₂H₅—(CH₂)₂— | | S | t-C₄H₉— | 200–201 | β |
| I-1-c-21 | CH₃ | CH₃ | —(CH₂)₂—CHOC₂H₅—(CH₂)₂— | | S | C₆H₅—CH₂— | 148–149 | β |

Example I-1-g-1

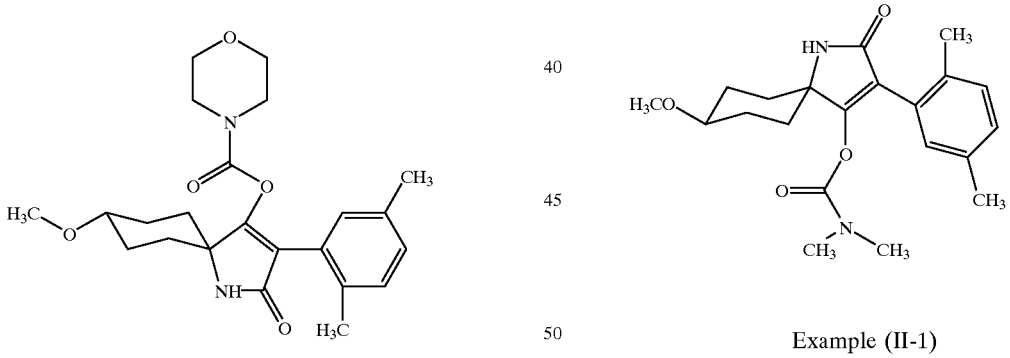

Example (II-1)

1.8 g (6 mmol) of the compound of Example I-1-a-4 and 1.2 ml (1.5 eq) triethylamine are precharged in 50 ml of methyl acetate and heated under reflux. 0.91 ml (1.1 g; 1.3 eq) of morpholine-N-carboxylic acid chloride in 5 ml of methyl acetate are added. The mixture is heated under reflux over night, concentrated and the residue is taken up in CH₂Cl₂. The organic phase is washed twice with 40 ml of N NaOH each time, dried and concentrated. The residue (2.7 g) is stirred with petrol ether, filtered off with suction and dried. Yield: 0.90 g (36% of theory), mp.: 132° C.

Example I-1-g-2

Similar to Example I1-g-1 and/or according to the general preparation instructions the compound is obtained as an oil:

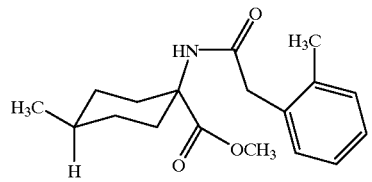

At 0–10° C., 16.9 g of 2-methylphenylacetyl chloride in 20 ml of anhydrous tetrahydrofuran (THF) are added dropwise to 20.8 g of methyl 1-amino-4-methylcyclohexanecarboxylate and 29.4 ml (0.21 mol) of triethylamine in 200 ml of anhydrous THF, and the mixture is stirred at room temperature. After the reaction has ended (control by thin-layer chromatography (TLC)), the mixture is concentrated, taken up in a mixture of 0.5N HCl/methylene chloride and the organic phase is dried and concentrated. The residue is recrystallized from MTBE/n-hexane.

Yield: 17.9 g (59% of theory); mp.: 107° C.

Similar to Example (II-1) and/or according to the general preparation instructions, the following compounds of the formula (II) are obtained:

The catalyst is filtered off, the filtrate is concentrated and the residue is recrystallized from MTBE/n-hexane. 10.3 g of a solid of mp.: 94° C. are obtained. Concentration of the mother liquor affords a further 20 g of product as an oil.

Total yield: 89% of theory.

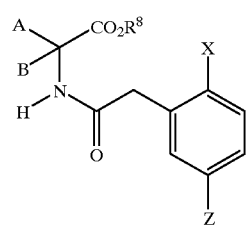

(II)

| Ex. No. | X | Z | A | B | R⁸ | Isomer | mp. °C. |
|---|---|---|---|---|---|---|---|
| II-2 | CH₃ | H | —(CH₂)₂—CHOCH₃—(CH₂)₂— | | CH₃ | β | 98 |
| II-3 | CH₃ | CH₃ | —(CH₂)₂—CHCH₃—(CH₂)₂— | | CH₃ | β | 120 |
| II-4 | CH₃ | CH₃ | —(CH₂)₂—CHOCH₃—(CH₂)₂— | | CH₃ | β | 90 |
| II-5 | CH₃ | CH₃ | CH₃ | CH₃ | CH₃ | — | |
| II-6 | OCH₃ | H | —(CH₂)₂—CHCH₃—(CH₂)₂— | | CH₃ | β | 138 |
| II-7 | O—CH₂—C₆H₅ | H | —(CH₂)₂—CHCH₃—(CH₂)₂— | | CH₃ | β | 85 |
| II-8 | OCH₃ | Cl | —(CH₂)₂—CHOCH₃—(CH₂)₂— | | CH₃ | β | 149 |
| II-9 | CH₃ | CH₃ | —(CH₂)₂—CHOC₂H₅—(CH₂)₂— | | CH₃ | β | 108 |
| II-10 | CH₃ | CH₃ | i-C₃H₇ | CH₃ | CH₃ | — | 75 |
| II-11 | CH₃ | CH₃ | —(CH₂)₂—O—(CH₂)₂— | | CH₃ | — | 153 |
| II-12 | Cl | NO₂ | —(CH₂)₂—CHCH₃—(CH₂)₂— | | CH₃ | β | 158 |
| II-13 | Cl | Cl | —(CH₂)₂—CHOCH₃—(CH₂)₂— | | CH₃ | β | 112 |
| II-14 | Cl | CH₃ | —(CH₂)₂—CHOCH₃—(CH₂)₂— | | CH₃ | β | 171 |
| II-15 | Cl | H | —(CH₂)₂—CHOCH₃—(CH₂)₂— | | CH₃ | β | 68 |
| II-16 | Br | OCH₃ | —(CH₂)₂—CHCH₃—(CH₂)₂— | | CH₃ | β | 131 |
| II-17 | Br | OCH₃ | —(CH₂)₂—CHOCH₃—(CH₂)₂— | | CH₃ | β | 158 |
| II-18 | Br | Br | —(CH₂)₂—CHOCH₃—(CH₂)₂— | | CH₃ | β | 132 |
| II-19 | F | CH₃ | —(CH₂)₂—CHOCH₃—(CH₂)₂— | | CH₃ | β | 74–76 |
| II-20 | F | OCH₃ | —(CH₂)₂—CHOCH₃—(CH₂)₂— | | CH₃ | β | 169 |
| II-21 | F | F | —(CH₂)₂—CHOCH₃—(CH₃)₂— | | CH₃ | β | 91 |
| II-22 | Cl | NH₂ | —(CH₂)₂—CHCH₃—(CH₂)₂— | | CH₃ | β | 94 |
| II-23 | Cl | NO₂ | —(CH₂)₂—CHOCH₃—(CH₂)₂— | | CH₃ | β | 127 |
| II-24 | Cl | Br | —(CH₂)₂—CHOCH₃—(CH₂)₂— | | CH₃ | β | 126–128 |
| II-25 | Cl | CF₃ | —(CH₂)₂—CHOCH₃—(CH₂)₂— | | CH₃ | β | 109–111 |
| II-26 | Br | CH₃ | —(CH₂)₂—CHOCH₃—(CH₂)₂— | | CH₃ | β | 100–102 |

Example (II-10)

At an internal temperature of 30 to 40° C., 16.7 g of the compound of Example (XXVIII-1) in 200 ml of methylene chloride are added dropwise to 32.2 g (0.326 mol) of concentrated sulphuric acid, and the mixture is stirred for a further 2 hours at this temperature. 42 ml of anhydrous methanol are then added dropwise in such a way that an internal temperature of 40° C. is obtained. The mixture is stirred at 40 to 70° C. for a further 6 hours, poured onto 0.35 kg of ice and extracted with methylene chloride, the organic phase is washed with aqueous NaHCO₃ solution, dried and concentrated and the residue is crystallized from MTBE/n-hexane.

Yield: 7.40 g (39% of theory), mp.: 75° C.

Example (II-22)

37 g of the compound of Example (II-12) in 370 ml of ethanol are admixed with Raney nickel and hydrogenated.

Example (I-2-a-1)

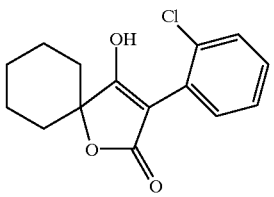

At 0 to 10° C., a solution of 16.6 g (50 mmol) of 1-ethyloxycarbonyl-cyclohexyl 2-chlorophenylacetate according to Example (III-1) in 50 ml of tetrahydrofuran (THF) are added dropwise to 8.42 g (75 mmol) of potassium tert-butoxide in 50 ml of anhydrous THF, and the mixture is stirred at room temperature for 16 h.

For work-up, the reaction mixture is added dropwise to 500 ml of ice-cold 1N HCl, and the precipitated product is filtered off with suction, washed with water and dried in a vacuum drying cabinet.

Yield: 10.19 g (80% of theory) of mp.: 231° C.

Similar and/or according to the general preparation instructions, the following compounds of the formula (I-2-a) are obtained:

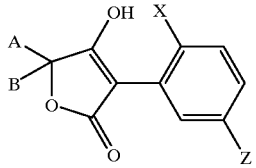
(I-2-a)

| Ex. No. | X | Z | A | B | mp. ° C. |
|---|---|---|---|---|---|
| I-2-a-2 | CH$_3$ | H | —(CH$_2$)$_5$— | | 233 |
| I-2-a-3 | OCH$_3$ | H | —(CH$_2$)$_5$— | | 177 |
| I-2-a-4 | F | H | —(CH$_2$)$_5$— | | 233 |
| I-2-a-5 | i-C$_3$H$_7$ | H | —(CH$_2$)$_5$— | | 200 |
| I-2-a-6 | CH$_3$ | CH$_3$ | —(CH$_2$)$_2$—CHOCH$_3$—(CH$_2$)$_2$— | | 180 |
| I-2-1-7 | CH$_3$ | CH$_3$ | —(CH$_2$)$_2$—CHCH$_3$—(CH$_2$)$_2$— | | 240 |

Example (I-2-b-1)

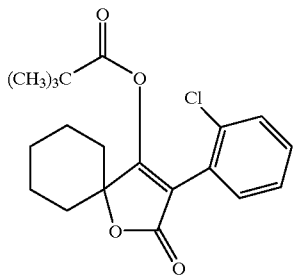

2.79 g (10 mmol) of the compound of Example (I-2-a-1) are precharged in 50 ml of anhydrous THF, 1.21 g (12 mmol) of triethylamine are added, a solution of 1.33 g (11 mmol) of pivaloyl chloride is added dropwise with ice cooling, and the mixture is stirred at room temperature for 16 h. For work-up, the mixture is stirred into 200 ml of water and the product is filtered off with suction and dried.

Yield: 3.5 g (98% of theory) of mp.: 128° C.

Similar and/or according to the general preparation instructions, the following compounds of the formula (I-2-b) are obtained:

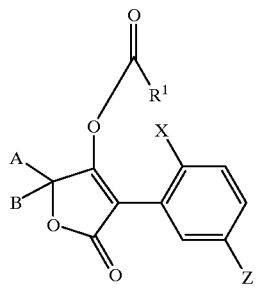
(I-2-b)

| Ex. No. | X | Z | A | B | R$^1$ | mp. ° C. |
|---|---|---|---|---|---|---|
| I-2-b-2 | CH$_3$ | H | | —(CH$_2$)$_5$— | t-C$_4$H$_9$ | 101 |
| I-2-b-3 | Cl | H | | —(CH$_2$)$_5$— | H$_5$C$_2$—C(CH$_3$)$_2$— | 90–92 |
| I-2-b-4 | OCH$_3$ | H | | —(CH$_2$)$_5$— | t-C$_4$H$_9$ | oil |
| I-2-b-5 | F | H | | —(CH$_2$)$_5$— | t-C$_4$H$_9$ | 88 |
| I-2-b-6 | i-C$_3$H$_7$ | H | | —(CH$_2$)$_5$— | t-C$_4$H$_9$ | 98 |
| I-2-b-7 | CH$_3$ | CH$_3$ | | —(CH$_2$)$_2$—CHOCH$_3$—(CH$_2$)$_2$— | i-C$_3$H$_7$ | 91 |
| I-2-b-8 | CH$_3$ | CH$_3$ | | —(CH$_2$)$_2$—CHCH$_3$—(CH$_2$)$_2$— | i-C$_3$H$_7$ | 104–106 |

Example (I-2-c-1)

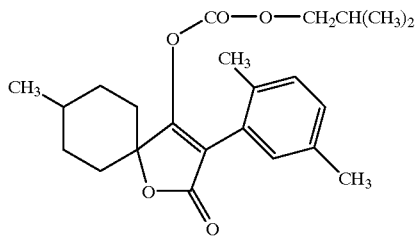

At 0 to 10° C., 1.43 g of the compound of Example (I-2-a-7) in 30 ml of methylene chloride are admixed with 0.55 g of triethylamine and 0.75 g of isobutyl chloroformate.

Work-up is carried out as described in Example (I-1-c-1).

Yield: 0.94 g; m.p.: 70° C.

Example (I-2-c-2)

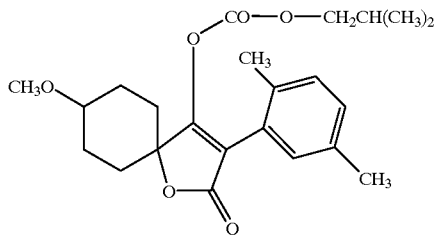

This compound was obtained in a similar manner starting from the compound of Example (I-2-a-6).

Yield: 1.7 g, semicrystalline.

Example (III-1)

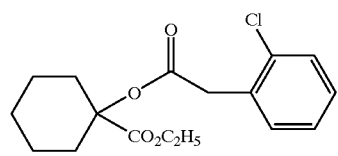

8.6 g (50 mmol) of 2-chlorophenylacetyl chloride together with 8.6 g (50 mmol) of ethyl 1-hydroxy-cyclohexanecarboxylate are stirred for 5 hours at 120° C. and degassed using an oil pump.

Yield: 15.26 g of 1-ethoxycarbonyl-cyclohexyl 2-chlorophenylacetate as a colourless oil.

$^1$H NMR (300 MHz, CDCl$_3$): δ=1.18 (t, 3H, CH$_2$CH$_3$), 1.2–1.82 (m, 8H, c-Hcx), 2.12 (m, 2H, c-Hcx), 3.81 (s, 2H, CH$_2$—CO), 4.14 (q, 2H, O—CH$_2$—CH$_3$), 7.15–7.4 (m, 4H, Ar-H).

In a similar manner and/or according to the general preparation instructions, the following compounds of the formula (III) are obtained:

(III)

| Ex. No. | X | Z | A | B | R$^8$ | mp. ° C. |
|---|---|---|---|---|---|---|
| III-2 | CH$_3$ | H | | —(CH$_2$)$_5$— | C$_2$H$_5$ | oil |
| III-3 | OCH$_3$ | H | | —(CH$_2$)$_5$— | C$_2$H$_5$ | oil |
| III-4 | F | H | | —(CH$_2$)$_5$— | C$_2$H$_5$ | oil |
| III-5 | i-C$_3$H$_7$ | H | | —(CH$_2$)$_5$— | C$_2$H$_5$ | oil |
| III-6 | CH$_3$ | CH$_3$ | | —(CH$_2$)$_2$—CHOCH$_3$—(CH$_2$)$_2$— | C$_2$H$_5$ | oil |
| III-7 | CH$_3$ | CH$_3$ | | —(CH$_2$)$_2$—CHCH$_3$—(CH$_2$)$_2$— | C$_2$H$_5$ | oil |

Example (I-3-a-1)

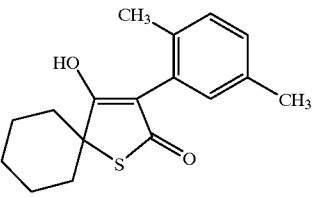

19 g of the compound of Example (IV-1) in 86 ml of toluene and 43 ml of trifluoroacetic acid are heated under reflux overnight. Excess trifluoroacetic acid is removed under reduced pressure, the residue is taken up in 400 ml of water and 120 ml of MTBE and the pH is adjusted to a value of 14 by adding NaOH. The mixture is extracted twice with MTBE and the aqueous phase is acidified with HCl and extracted 3 times with MTBE. The organic phase is dried and evaporated.

Yield: 7.8 g (63% of theory); m.p.: 185–187° C.

Example (I-3-b-1)

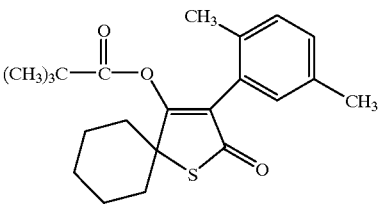

1.5 g of the compound of Example (I-3-a-1) in 20 ml of methylene chloride are admixed with 1.08 ml of triethylamine. Cooling with ice, a solution of 0.96 ml of pivaloyl chloride in 3 ml of methylene chloride is added dropwise, and stirring is continued at room temperature for a further 2 hours. The mixture is washed twice with 10% strength citric acid and extracted with methylene chloride. The combined organic phases are washed twice with 1N NaOH, and the aqueous alkaline phases are extracted with methylene chloride. The combined organic phases are dried and concentrated.

Yield: 1.90 g (98% of theory); m.p.: 79–83° C.

Example (I-3-b-2)

Similar to Example (I-3-b-1), when using isobutyryl chloride instead of pivaloyl chloride the following compound of m.p.: 149–152° C. is obtained in quantitative yield:

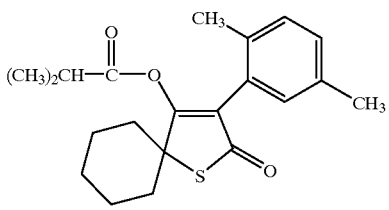

Example (I-3-c-1)

Similar to Example (I-3-b-1), when using isobutyl chloroformate instead of pivaloyl chloride the following compound of m.p.: 101–103° C. is obtained in a yield of 98% of theory:

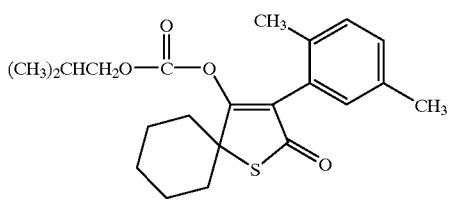

Example (IV-1)

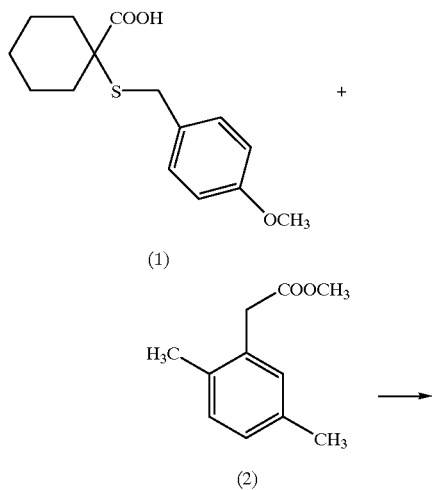

A: 10 g of the compound (1) in 40 ml of toluene are admixed with 1 drop of DMF and 6.4 g of thionyl chloride and stirred for 5 minutes at room temperature and then at 100° C. until the formation of gas ceases.

Excess thionyl chloride is removed (high vacuum) and the acid chloride is dissolved in 20 ml of THF (tetrahydrofuran): Solution A.

B: At 0° C., 10.7 g of the compound (2) in 20 ml of THF are added dropwise to 32 ml of a solution of lithium diisopropylamide (LDA) (65.8 mmol) in 50 ml of THF, and the mixture is stirred at 0° C. for 30 minutes. The solution A is then added dropwise at this temperature, and the mixture is stirred for a further 1 hour without cooling.

The mixture is admixed with 175 ml of MTBE and a few drops of water. The mixture is then washed twice with 10% strength aqueous ammonium chloride solution and the organic phase is dried and concentrated. Yield: 19 g (oil).

$^1$H NMR (400 MHz, CDCl$_3$): 1.2–2.0 (m, 10H, CH$_2$); 2.32, 2.38 (2s, 2×3H; CH$_3$), 3.22 (dd, 2H, CH$_2$); 3.71, 3.76 (2s, 2×3H, OCH$_3$); 6.7–7.4 (m, 7H, Phenyl-H).

Example (I-4-a-1)

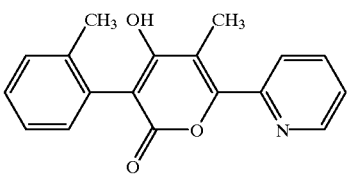

1.9 g (10 mmol) of 2-(2-methyl-phenyl)-chlorocarbonylketene were precharged in 20 ml of anhydrous toluene. After the addition of 1.4 g (10 mmol) of ethyl 2-pyridyl ketone, the mixture is heated under reflux for 8 h. After cooling, the precipitate is filtered off with suction and washed twice with cyclohexane.

Yield: 2.1 g (71% of theory); m.p.: 105–107° C.

In a similar manner and/or according to the general preparation instructions, the following compounds of the formula (I-4-a) are obtained:

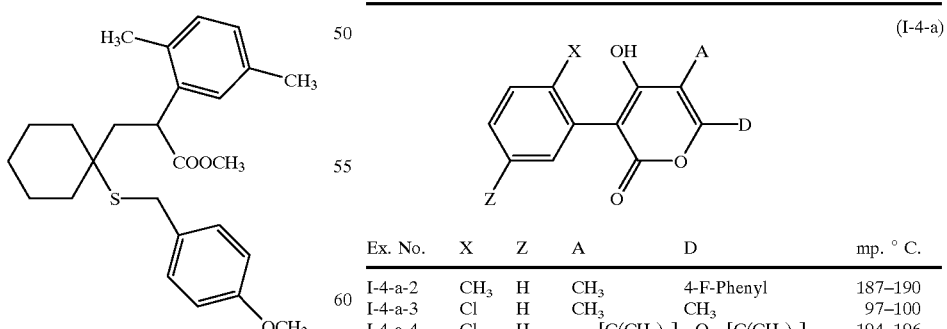

| Ex. No. | X | Z | A | D | mp. ° C. |
|---|---|---|---|---|---|
| I-4-a-2 | CH$_3$ | H | CH$_3$ | 4-F-Phenyl | 187–190 |
| I-4-a-3 | Cl | H | CH$_3$ | CH$_3$ | 97–100 |
| I-4-a-4 | Cl | H | —[C(CH$_3$)$_2$]—O—[C(CH$_3$)$_2$]— | | 194–196 |
| I-4-a-5 | CH$_3$ | CH$_3$ | —[C(CH$_3$)$_2$]—O—[C(CH$_3$)$_2$]— | | 174–175 |
| I-4-a-6 | CH$_3$ | CH$_3$ | —(CH$_2$)$_4$— | | 198–200 |
| I-4-a-7 | CH$_3$ | CH$_3$ | CH$_3$ | 2-Pyridyl | 99–102 |
| I-4-a-8 | CH$_3$ | CH$_3$ | CH$_3$ | 4-Pyridyl | 273–275 |
| I-4-a-9 | CH$_3$ | CH$_3$ | CH$_3$ | CH$_3$ | 57–59 |

Example (I-4-b-1)

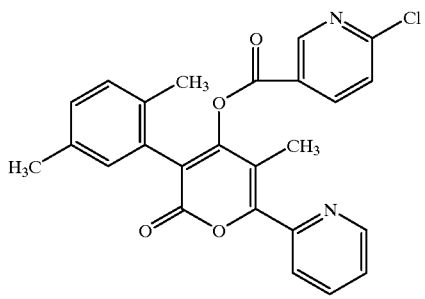

1.2 g (4 mmol) of the compound of Example (I-4-a-7) in 10 ml of ethyl acetate are admixed with 0.4 g (4 mmol) of triethylamine, and at 0° C. 0.7 g (4 mmol) of 6-chloropyrid-3-yl-carbonyl chloride dissolved in 4 ml of ethyl acetate are added dropwise. The mixture is kept for 20 hours at room temperature and the precipitate is filtered off with suction and washed with ethyl acetate. The organic phase is washed twice with 20 ml of half concentrated aqueous NaCl solution each time, dried and concentrated.

Yield: 2 g (91% of theory), m.p.: 70 to 73° C.

Similar to Example (I-4-b-1) and/or according to the general preparation instructions, the following compounds of the formula (I-4-b) are obtained:

(I-4-b)

| Ex. No. | X | Z | A | D | R$^1$ | mp. ° C. |
|---|---|---|---|---|---|---|
| I-4-b-2 | CH$_3$ | CH$_3$ | CH$_3$ | 2-Pyridyl | 4-Cl-Phenyl | 73–75 |
| I-4-b-3 | CH$_3$ | CH$_3$ | CH$_3$ | 2-Pyridyl | CH$_3$ | 119–120 |
| I-4-b-4 | CH$_3$ | CH$_3$ | CH$_3$ | 2-Pyridyl | cyclopropyl-Cl | 120–121 |
| I-4-b-5 | CH$_3$ | CH$_3$ | CH$_3$ | 2-Pyridyl | (CH$_3$O—CH$_2$)$_2$C(CH$_3$)— | 119–121 |
| I-4-b-6 | CH$_3$ | CH$_3$ | CH$_3$ | 2-Pyridyl | dioxane-CH$_3$ | 120–122 |

Example (I-4-c-1)

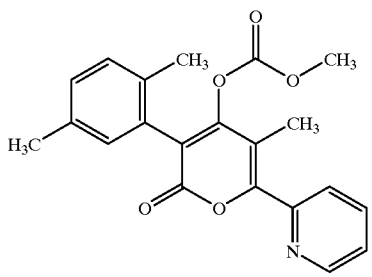

1.5 g (5 mmol) of the compound of Example (I-4-a-7) in 20 ml of ethyl acetate are admixed with 0.5 g (5 mmol) of triethylamine, and at 0° C. 0.47 g (5 mmol) of methyl chloroformate in 5 ml of ethyl acetate are added dropwise. The mixture is stirred for 20 hours at room temperature and the precipitate is separated off and washed with ethyl acetate. The organic phase is washed twice with 25 ml of half concentrated aqueous NaCl solution each time, dried and concentrated.

Yield: 1.7 g (93% of theory); m.p.: 136–137° C.

Example (XXXII-1)

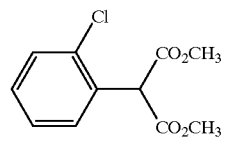

236 g (2.8 mol) of dimethyl carbonate are precharged in 814 ml of anhydrous toluene, and 27.3 g (0.91 mol) of sodium hydride (80%) are added. At 80° C., 133 g (0.7 mol) of methyl 2-chlorophenylacetate are added dropwise, and the mixture is stirred at 80–90° C. for 16 h. The mixture is poured into 2 l of ice water and acidified with half-concentrated HCl to pH 4, the organic phase is separated off and the aqueous phase is extracted with 150 ml of toluene. The combined organic phases are dried, the solvent is distilled off and the residue is distilled using high vacuum.

Yield: 122.9 g (72% of theory) bp$_{0.6-0.7\ mbar}$ 129–131° C.

In a similar manner and/or according to the general preparation instructions, the following compounds of the formula (XXXII) are obtained:

(XXXII)

| Ex. No. | X | Z | R$^8$ | bp. |
|---|---|---|---|---|
| XXXII-2 | CH$_3$ | H | CH$_3$ | used as crude product |
| XXXII-3 | CH$_3$ | CH$_3$ | CH$_3$ | $^1$H NMR(400 MHz, CDCl$_3$): δ=2.25(s, 3H, CH$_3$); 1.28(3H, s, CH$_3$); 3.78(s, 6-H, 2 x CO$_2$CH$_3$); 4.88(s, 1H, CH). |

Example (XXXI-1)

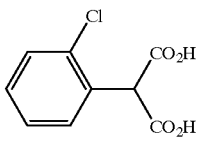

93.3 g (1.67 mol) of potassium hydroxide are dissolved in 125 ml of water and admixed with 250 ml of methanol. 121.3 g (0.5 mol) of the compound of Example (XXXII-1) are then added dropwise. After 5 h at reflux, the mixture is evaporated and the residue is dissolved in ethyl acetate and, at 0° C., carefully acidified with concentrated hydrochloric acid. The precipitate is filtered off with suction and dried over calcium chloride under reduced pressure.

Yield: 29.2 g (27% of theory); m.p.: 135–136° C. (decomposition).

In a similar manner and/or according to the general preparation instructions, the following compounds of the formula (XXXI) are obtained:

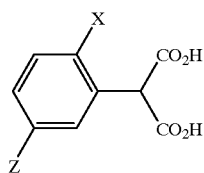
(XXXI)

| Ex. No. | X | Z | mp. ° C. |
|---|---|---|---|
| XXXI-2 | $CH_3$ | H | 149–150 (Decomp.) |
| XXXI-3 | $CH_3$ | $CH_3$ | 150 |

Example (VI-1)

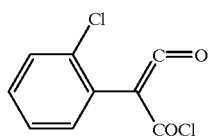
(VI-1)

27.9 g (0.13 mol) of 2-(2-chloro-phenyl)-malonic acid are precharged in 32 ml of anhydrous toluene, 59 g (0.391 mol) of thionyl chloride are added dropwise and the mixture is heated under reflux for 5 hours. After concentration and distillation, 20.7 g (74% of theory) of 2-(2-chlorophenyl)-2-chlorocarbonylketene of $bp._{1\ mbar}$ 102° C. are obtained.

In a similar manner and/or according to the general preparation instructions, the following compounds of the formula (VI) are obtained:

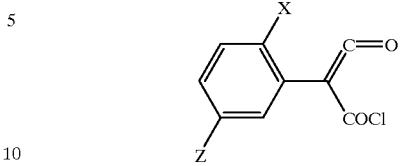
(VI)

| Ex. No. | X | Y | bp. ° C. |
|---|---|---|---|
| VI-2 | $CH_3$ | H | 92–94 (0.6 mbar) |
| VI-3 | $CH_3$ | $CH_3$ | $^1$H NMR(400 MHz, $CDCl_3$) δ=2.20, 2.21(2s, 6H, 2$CH_3$); 7.05(m, 3H, Ph—H). |

Example (XXII-1)

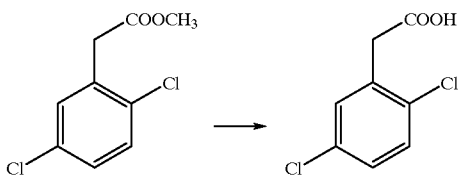

A solution of 5.10 g of 98% strength lithium hydroxide in 220 ml of water is added dropwise to 55 g of the carboxylic acid ester of Example (XXIII-1) shown above in 220 ml of THF, and the mixture is stirred at room temperature overnight. The mixture is then evaporated, the residue is admixed with water and extracted with MTBE, the aqueous phase is acidified with concentrated hydrochloric acid and the precipitated acid is filtered off with suction.

Similar to Example (XXII-1) and/or according to the general preparation instructions, the following compounds of the formula (XXII) are obtained:

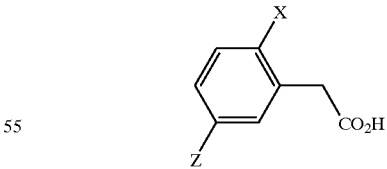
(XXII)

| Ex. No. | X | Z | mp. ° C. |
|---|---|---|---|
| XXII-2 | $OCH_3$ | Cl | 128–130 |
| XXII-3 | Cl | $CH_3$ | 116–120 |
| XXII-4 | F | $CH_3$ | 89 |
| XXII-5 | Br | Br | 95 |
| XXII-6 | F | F | 118 |
| XXII-7 | Cl | Br | 115 |
| XXII-8 | Cl | $CF_3$ | 110 |
| XXII-9 | Br | $CH_3$ | 117 |

Example (XXIII-1)

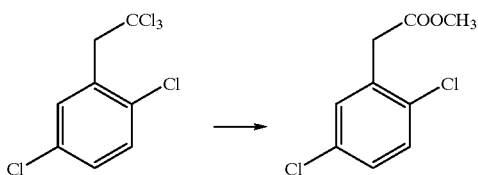

With cooling, 1020 ml of a 30% strength aqueous NaOCH₃ solution (5.67 mol) are added dropwise to 653 g (1.26 mol) (68% pure) of the compound of Example (XXIV-1) in 220 ml of methanol, and the mixture is stirred at reflux for 5 hours. With cooling, 200 ml of concentrated sulphuric acid are then added dropwise, and the mixture is stirred under reflux for a further 1 hour.

The mixture is concentrated, admixed with water and extracted with methylene chloride. The extract is dried and concentrated.

Crude yield: 355 g (81% pure).

Similar to Example (XXIII-1) and/or according to the general preparation instructions, the following compounds of the formula (XXIII) are obtained:

(XXIII)

| Ex. No. | X | Z | R⁸ | bp$_{mbar}$ °C. |
|---|---|---|---|---|
| XXIII-2 | OCH₃ | Cl | CH₃ | 120 0.09 |
| XXII-3 | Cl | CH₃ | CH₃ | 125 0.1 |
| XXIII-4 | F | CH₃ | CH₃ | 60 0.05 |
| XXIII-5 | Br | Br | CH₃ | GC/MS 308(M⁺, 4%) 249(42%) 227(77%) |
| XXIII-6 | F | F | CH₃ | 100 0.03 |
| XXIII-7 | Cl | Br | CH₃ | 101° C./0.25 mbar |
| XXIII-8 | Cl | CF₃ | CH₃ | Kp: 110° C./0.35 mbar |
| XXIII-9 | Br | CH₃ | CH₃ | GC/MS 183(29%) 163(100%) |

Example (XXIV-1)

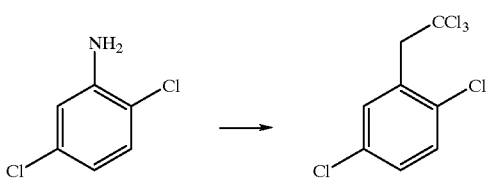

Under argon, 202.9 g of anhydrous copper(II) chloride and then 1890 g of 1,1-dichloroethane are added to 229 g of isopentyl nitrite in 750 ml of anhydrous acetonitrile. Below 30° C., 204 g of 2,5-dichloroaniline are added a little at a time, and the mixture is stirred at room temperature overnight until the formation of gas ceases. The mixture is poured into 3600 ml of ice-cold 20% strength hydrochloric acid, stirred for 10 minutes and extracted repeatedly with MTBE. The organic phase is washed with 20% strength HCl, dried and concentrated.

MS in accordance with the structure.

Similar to example (XXIV-1) and/or according to the general preparation instructions, the following compounds of the formula (XXIV) are obtained:

(XXIV)

| Ex. No. | X | Z | GC/MS |
|---|---|---|---|
| XXIV-2 | OCH₃ | Cl | 274(12%, M⁺) 155(100%) |
| XXIV-3 | Cl | CH₃ | 256(5%, M⁺) 185(7%) 139(100%) |
| XXIV-4 | F | CH₃ | 242(7%, M⁺) 123(100%) |
| XXIV-5 | Br | Br | 366(13%, M⁺) 249(100%) |
| XXIV-6 | F | F | 246(5%, M⁺) 127(100%) |
| XXIV-7 | Cl | Br | M⁺322(17%) 205(100%) |
| XXIV-8 | Cl | CF₃ | M⁺312(4%) 193(100%) |
| XXIV-9 | Br | CH₃ | M⁺302(22%) 185(100%) |

Example (XXVIII-1)

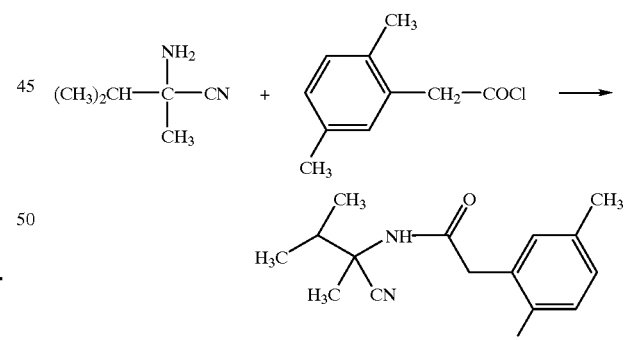

At 0 to 10° C., 14.9 g of 2,5-dimethylphenylacetyl chloride in 20 ml of THF are added dropwise to 9 g (0.08 mol) of the aminonitrile shown above in 160 ml of THF and 12.3 ml of triethylamine.

After the reaction has ended, the mixture is concentrated, the residue is taken up in 0.5N HCl/methylene chloride and the organic phase is dried and concentrated. The residue is chromatographed over silica gel using n-hexane/ethyl acetate.

Yield: 16.70 g (80% of theory); m.p.: 89° C.

Example (XXVIII-2)

In a similar manner, the compound of the formula

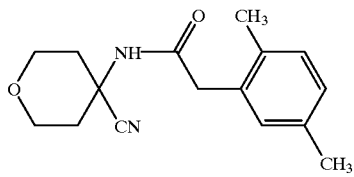

is obtained in quantitative yield: m.p.: 198° C.

Use Examples

Example A

Phaedon Larvae Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*) while the leaves are still moist.

After the specified period of time, the destruction in % is determined. 100% means that all the beetle larvae have been killed; 0% means that none of the beetle larvae have been killed.

In this test, for example the compounds of Preparation Examples (I-1-a-1) and (I-4-a-1) at an exemplary active compound concentration of 0.1% caused a destruction of in each case 100% after 7 days.

Example B

Plutella Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (*Plutella maculipennis*) while the leaves are still moist.

After the specified period of time, the destruction in % is determined. 100% means that all the caterpillars have been killed; 0% means that none of the caterpillars have been killed.

In this test, for example the compounds of preparation examples (I-4-a-1) and (I-4-a-2) at an exemplary active compound concentration of 0.1% caused a destruction of in each case 100% after 7 days.

Example C

Spodoptera Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with caterpillars of the owlet moth (*Spodoptera frugiperda*) as long as the leaves are still moist.

After the specified period of time, the destruction in % is determined. 100% means that all the caterpillars have been killed; 0% means that none of the caterpillars have been killed.

In this test, for example the compounds of preparation examples (I-1-a-1) and (I-4-a-1) at an exemplary active compound concentration of 0.1% caused a destruction of in each case 85% after 7 days.

Example D

Myzus Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) which have been heavily infested with the peach aphid (*Myzus persicae*) are treated by being dipped into the preparation of the active compound of the desired concentration.

After the specified period of time, the destruction in % is determined. 100% means that all the aphids have been killed; 0% means that none of the aphids have been killed.

In this test, for example the compounds of preparation examples (I-2-a-1), (I-2-b-1), (I-2-b-2), (I-1-a-1) and (I-4-a-1) at an exemplary active compound concentration of 0.1% caused a destruction of in each case at least 90% after 6 days.

Example E

Nephotettix Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Rice seedlings (*Oryzae sativa*) are treated by being dipped into the preparation of the active compound of the desired concentration and are infested with larvae of the green rice leaf hopper (*Nephotettix cincticeps*) while the seedlings are still moist.

After the specified period of time, the destruction in % is determined. 100% means that all the larvae have been killed; 0% means that none of the larvae have been killed.

In this test, for example the compounds of preparation examples (I-2-a-2), (I-2-b-3), (I-1-a-1), (I-4-a-1) and (I-4-a-2) at an exemplary active compound concentration of 0.1% caused a destruction of in each case 100% after 6 days.

Example F

Tetranychus Test (OP Resistant)

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) heavily infested by all stages of the common spider mite (*Tetranychus urticae*) are dipped into a preparation of the active compound of the desired concentration.

After the specified period of time, the destruction in % is determined. 100% means that all the spider mites have been killed; 0% means that none of the spider mites have been killed.

In this test, for example the compounds of preparation examples (I-2-a-1), (I-2-a-2), (I-2-b-1) and (I-2-b-2) at an exemplary active compound concentration of 0.1% had an efficacy of in each case at least 98% after 9 days.

Example G
Tetranychus Test (OP Resistant/Dip Treatment)
Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) heavily infested by all stages of the common spider mite (*Tetranychus urticae*) are dipped into a preparation of the active compound of the desired concentration.

After the specified period of time, the destruction in % is determined. 100% means that all the spider mites have been killed; 0% means that none of the spider mites have been killed.

In this test, for example the compounds of preparation examples (I-2-a-1), (I-2-a-2), (I-2-b-1) and (I-2-b-2) at an exemplary active compound concentration of 0.01% had an efficacy of in each case at least 95% after 13 days.

Example H
Panonychus Test
Solvent: 3 parts by weight of dimethylformamide
Emulsifier: 1 part by weight of alkylaryl polyglycol ether To prepare a suitable preparation of active compound, 1 part by weight of active compound is mixed with the stated amount of solvent and the stated amount of emulsifier, and the concentrate is diluted with water to the desired concentration.

Plum trees (*Prunus domestica*) approximately 30 cm in height which are severely infested by all stages of the fruit tree spider mite (*Panonychus ulmi*) are sprayed with an active compound preparation of the desired concentration.

After the specified period of time, the destruction in % is determined. 100% means that all the spider mites have been killed; 0% means that none of the spider mites have been killed.

In this test, for example the compounds of preparation examples (I-2-b-1) and (I-2-b-2) at an exemplary active compound concentration of 0.004% had an efficacy of in each case 100% after 7 days.

Example I
Test With Fly Larvae/Development-inhibitory Action
Test animals:
All larval stages of *Lucilia cuprina* (OP resistant) [pupae and adults (without contact with the active compound)]
Solvent:
35 parts by weight of ethylene glycol monomethyl ether
35 parts by weight of nonylphenol polyglycol ether To produce a suitable preparation, 3 parts by weight of active compound are mixed with 7 parts of the abovementioned solvent-emulsifier mixture, and the resulting emulsion concentrate is diluted with water to the desired concentration in each case.

For each individual concentration, 30 to 50 larvae are introduced into a test tube which contains 1 cm³ of horse meat. 500 µl of the dilution to be tested are pipetted onto this horse meat. The test tubes are placed in plastic beakers whose bottom is covered with sea sand, and kept in a climatized room (26° C. ±1.5° C., 70% ±10% relative humidity). The activity is examined (larvicidal action) after 24 hours and again after 48 hours. After emergence of the larvae (about 72 h), the test tubes are removed and perforated plastic lids are fitted to the beakers. After 1.5 times the development time (hatching of the control flies), the hatched flies and the pupae/coccoons are counted.

The activity criterion is the incidence of death in the treated larvae after 48 h (larvicidal effect), or the inhibition of the hatching of adults from pupae or the inhibition of pupa formation. The criterion for the in vitro activity of a substance is the inhibition of the development of the flies, or a development standstill before the adult stage. 100% larvicidal action means that all the larvae have been killed after 48 hours. 100% development-inhibitory action means that no adult flies have hatched.

In this test, a development-inhibitory action of 100% was shown, for example, by the compound of Preparation Example (I-2-b-3) at an exemplary active compound concentration of 1000 ppm.

Example K
Test With *Boophilus Microplus* Resistant/SP Resistant Parkhurst Strain Test animals: adult females which have sucked themselves full Solvent: dimethyl sulphoxide 20 mg of active substance are dissolved in 1 ml of dimethyl sulphoxide, and lesser concentrations are prepared by dilution with the same solvent.

The test is carried out in 5 replications. 1 µl of the solutions is injected into the abdomen, and the animals are transferred into dishes and kept in a controlled-environment cabinet. The activity is determined via the inhibition of oviposition. 100% means that no tick has deposited eggs.

In this test, an activity of 100% was shown, for example, by the compound of Preparation Example (I-1-a-2) at an exemplary active compound concentration of 20 µg/animal.

What is claimed is:

1. A compound having the formula (II)

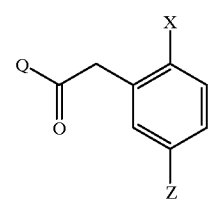

(II)

in which

Q represents

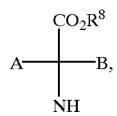

A represents a respectively optionally substituted radical from the group consisting of alkyl, alkenyl, alkoxyalkyl, polyalkoxyalkyl and alkylthioalkyl, represents respectively saturated or unsaturated and optionally substituted cycloalkyl or heterocyclyl or represents respectively optionally halogen-, alkyl-, halogenoalkyl-, alkoxy-, halogenoalkoxy-, cyano- or nitro-substituted aryl, arylalkyl or hetaryl, B represents alkyl or alkoxyalkyl or A and B together with the carbon atom that they are attached to represent a saturated or unsaturated, optionally substituted carbocycle or heterocycle, X represents halogen, alkyl, alkenyl, alkynyl, alkoxy, benzyloxy, halogenoalkyl, halogenoalkoxy, cyano or nitro, Z represents hydrogen, amino, halogen, alkyl, alkoxy, halogenoalkyl, halogenoalkoxy, hydroxyl, cyano, nitro or respectively optionally substituted phenoxy, phenylthio, 5- or 6-membered hetaryloxy, 5- or 6-membered hetarylthio, phenylalkyloxy or phenylalkylthio, and $R^8$ represents alkyl.

2. The compound of claim 1 having the formula

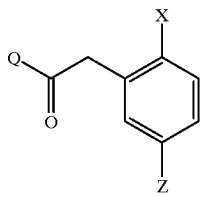

(III)

wherein

Q represents

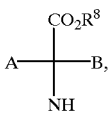

A represents a respectively optionally substituted radical from the group consisting of alkyl, alkenyl, alkoxyalkyl, polyalkoxyalkyl and alkylthioalkyl, represents respectively saturated or unsaturated and optionally substituted cycloalkyl or heterocyclyl or represents respectively optionally halogen-, alkyl-, halogenoalkyl-, alkoxy-, halogenoalkoxy-, cyano- or nitro-substituted aryl, arylalkyl or hetaryl, B represents alkyl or alkoxyalkyl or A and B together with the carbon atom that they are attached to represent a saturated or unsaturated, optionally substituted carbocycle or heterocycle, X represents halogen, alkyl, alkenyl, alkynyl, alkoxy, benzyloxy, halogenoalkyl, halogenoalkoxy, cyano or nitro, Z represents hydrogen, amino, halogen, alkyl, alkoxy, halogenoalkyl, halogenoalkoxy, hydroxyl, cyano, nitro or respectively optionally substituted phenoxy, phenylthio, 5- or 6-membered hetaryloxy, 5- or 6-membered hetarylthio, phenylalkyloxy or phenylalkylthio, and $R^8$ represents alkyl.

* * * * *

UNITED STATES PATENT AND TRADEMARK OFFICE
CERTIFICATE OF CORRECTION

PATENT NO. : 6,255,342 B1
DATED : July 3, 2001
INVENTOR(S) : Ulrike Wachendorff-Neumann et al.

It is certified that error appears in the above-identified patent and that said Letters Patent is hereby corrected as shown below:

Column 86,
Lines 5-9, delete the formula and insert the following:

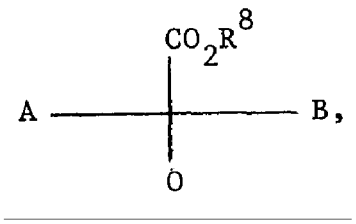

Signed and Sealed this

Seventeenth Day of August, 2004

JON W. DUDAS
*Acting Director of the United States Patent and Trademark Office*